(12) United States Patent
Gardner

(10) Patent No.: US 11,371,088 B2
(45) Date of Patent: Jun. 28, 2022

(54) METHOD FOR REMOVING AND/OR DETECTING NUCLEIC ACIDS HAVING MISMATCHED NUCLEOTIDES

(71) Applicant: New England Biolabs, Inc., Ipswich, MA (US)

(72) Inventor: Andrew F. Gardner, Manchester, MA (US)

(73) Assignee: New England Biolabs, Inc., Ipswich, MA (US)

( * ) Notice: Subject to any disclaimer, the term of this patent is extended or adjusted under 35 U.S.C. 154(b) by 330 days.

(21) Appl. No.: 16/616,631

(22) PCT Filed: Jun. 11, 2018

(86) PCT No.: PCT/US2018/036875
§ 371 (c)(1),
(2) Date: Nov. 25, 2019

(87) PCT Pub. No.: WO2019/005463
PCT Pub. Date: Jan. 3, 2019

(65) Prior Publication Data
US 2021/0164030 A1 Jun. 3, 2021

Related U.S. Application Data

(60) Provisional application No. 62/525,803, filed on Jun. 28, 2017.

(51) Int. Cl.
*C12Q 1/6855* (2018.01)
*C12N 9/22* (2006.01)
*C12N 9/00* (2006.01)
*C12Q 1/6874* (2018.01)

(52) U.S. Cl.
CPC ............. *C12Q 1/6855* (2013.01); *C12N 9/22* (2013.01); *C12N 9/93* (2013.01); *C12Q 1/6874* (2013.01)

(58) Field of Classification Search
None
See application file for complete search history.

(56) References Cited

U.S. PATENT DOCUMENTS

2013/0330778 A1* 12/2013 Zeiner et al. ...... C12N 15/1096
435/91.51
2014/0356867 A1    12/2014 Peter et al.
2017/0253909 A1*   9/2017 Uemori et al. .......... C12N 9/22

FOREIGN PATENT DOCUMENTS

WO         2013188037 A2     12/2013
WO    WO-2016039377 A1 *    3/2016    ............... C12Q 1/68

OTHER PUBLICATIONS

Ishino, et al., Nucleic Acids Research, 44, 7, 2977-2986, 2016.
(Continued)

*Primary Examiner* — Kaijiang Zhang
(74) *Attorney, Agent, or Firm* — New England Biolabs, Inc

(57) ABSTRACT

Provided herein, among other things, are various in vitro methods that involve cleaving dsDNA molecules that comprise a mismatched nucleotide using EndoMS. In some embodiments, the method may comprise ligating a T-tailed double-stranded adapter to A-tailed double-stranded fragments of nucleic acid to produce ligation products that comprise adapter-ligated fragments and double-stranded adapter dimers that comprise a T:T mismatch at the ligation junction and cleaving both strands of the adapter dimers using EndoMS.

9 Claims, 23 Drawing Sheets

Specification includes a Sequence Listing.

(56) References Cited

OTHER PUBLICATIONS

Head, et al., Biotechniques, 2014, 56, 61-68.
Shore, et al., PLoS One, 2016, 11, e0167009.
Kawano, et al., Biotechniques, 2010, 49, 751-755.
Shore, et al., Methods in Molecular Biology, 2018, vol. 1712, pp. 145-161.
Margulies, et al., Nature, 2005, 437:376-80.
Ronaghi, et al., Analytical Biochemistry, 1996, 242:84-9.
Shendure, Science, 2005, 309:1728.
Melfort, et al., Brief Bioinform. 2009, 10:609-18.
Fox, et al., Methods Mol Biol. 2009, 553:79-108.
Appleby, et al., Methods Mol Biol. 2009, 513:19-39.
English, PLoS One. 2012 7:e47768.
Morozova, Genomics, 2008, 92:255-64.

\* cited by examiner

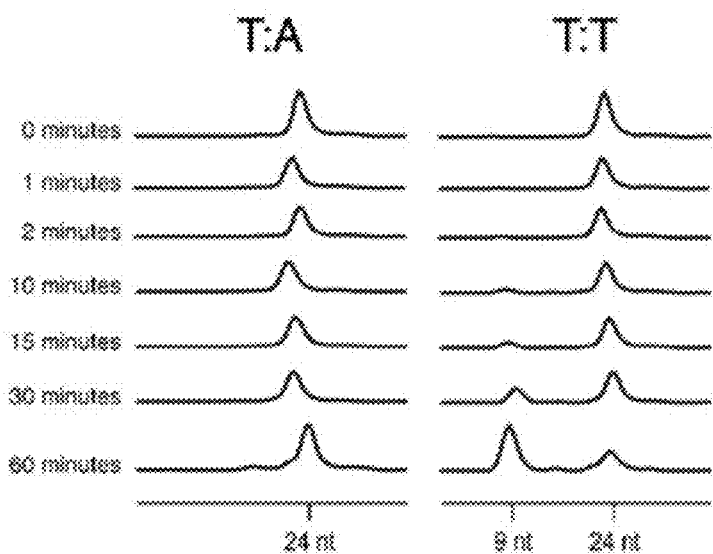

```
                1         10         20         30         40         50         60
                |          |          |          |          |          |          |
SEQ ID NO:1     MKYKILENPNCEDAYGLIEEALRKRATITIYACCKVNYEGRALSELNW-GERIILIKPDG
SEQ ID NO:2     MKYKILENPNCEDAYGLIEEALRKRATITIYACCKVNYEGRALSELNW-GERIILIKPDG
SEQ ID NO:3     MKYKILENPNCEDAYGLIVEEALRKKATITIYACCKVTYEGRALSELNW-GERIILIKPDG
SEQ ID NO:4     MKYKILENPNCEDAYGLIVEEALRKKATITIYACCKVTYEGRALSELNW-GERIILIKPDG
SEQ ID NO:5     MKYKILENPNCEDAYGLIVEEALRKKATITIIFACCKVNYEGRALSELNW-GERIILIKPDG
SEQ ID NO:6     MKYRILERPSCEGYDLVEEALRKKATILIFACCKVNYEGRALSQLNW-GERIILIKPDG
SEQ ID NO:7     MKYKILEKPSCEDGYDLVQEALRKKATILIFACCKVSYEGRALSELNW-GERIIMIKPDG
SEQ ID NO:8     MKYKILEKPSCEDGYDLVQEALRKKTTILIFACCKVSYEGRALSQLNW-GERIIMIKPDG
SEQ ID NO:9     MKYKILEKPDCEKAYELVEEAMRKRATITLFACCKVEYEGRALSQLNW-GERIILIKPDG
SEQ ID NO:10    MKYKILEKPNCEDAYELVQDALRKKATIIIFACCKVNYEGRALSQLNW-GERIIMIKPDG
SEQ ID NO:11    MKYRILERPSCEEGYDLIVEEALRKKATIIIFACCKVNYEGRALSQLNW-GERIILIKPDG
SEQ ID NO:12    MKYKILENPNIEEMYDLIEEGLRKKAMINVFCCCKVIYEGRALSQLDF-GERMILLKPDG
SEQ ID NO:13    MKFKGKEDPNIDESFDLIDEGLRKKATIVIFACCKVIYEGRAISQLDF-GERIILIKPDG
SEQ ID NO:14    MKYKILENPNYEETYDLIEEGLKKKATILLFACCRVSYEGRSISELDY-GERIIMMKPDG
SEQ ID NO:15    MKYKILENPNYKEAYELIEEGLVKKATMLLFACCKVSYEGRALSELDY-GERIIMIKPDG
SEQ ID NO:16    MNYKTIEEPNTEETYDLIEAGLRKKAMITLFTYCKVFYEGRALSQLGY-GERMILIKPDG
SEQ ID NO:17    MKYKLLENPDIEEAYDLIDSGIRKKAVINIFAYCKVLYEGRALSQLDW-GERFIMLKPDG
SEQ ID NO:18    MKYKLLENPDIEETYDLIDSGIRKKAVINIFAYCKVLYEGRALSQLDWGGERFIMLKPDG
SEQ ID NO:19    MKYKLLENPDIEETYDLIDSGIRKKAVINIFAYCKVLYEGRALSQLDW-GERFIMLKPDG
SEQ ID NO:20    MNYKNIEKPNINESYNFIEEGLRKKATISLYTYCKVEYEGRALSQLNY-GERLIIIKPDG
SEQ ID NO:21    MKCQVFENPSPKKAYRVIEEGIRKVLIVILACCSASYEGRARSRLEP-GERLIVIKPDG
SEQ ID NO:22    MRFISLENPTSEESCRIIKEGLRKKAMIIIFSCCKVRYGRAKSRLGP-GERLIIKPDG
SEQ ID NO:23    MKCKVSENPSIKEAYRLIEDGIPKRALVILACCSASYEGRARSRLDA-GERLIVIKPDG
SEQ ID NO:24    MKCCKVSENPSIKEAYRLIEDGIRKRALVVILACCSASYEGRARSRLDA-GERLIVIKPDG
SEQ ID NO:25    MKCRVSENPSRNEAYQLLEEGIRKRSLIVILACCSASYEGRARSSLGA-GERLIVIKPDG
SEQ ID NO:26    -RFKTIENPSPKESHELISEGLRKKAMILFACCKVQYHGRAKSRLGT-GERLIIIKPDG
SEQ ID NO:27    MKCRVSENPSRSEAYRLLEEGIRKRSLIVILACCSASYEGRARSSLGA-GERLIVIKPDG
SEQ ID NO:28    MIIKLDENPGTEEVFDFINEAISKRAFIIIVACCRIKYRGRATSRLGS-GDRTIIIKTDG
SEQ ID NO:29    MKFLSEKNPDIKRTYEIINEGISKRAVIVIMACCSVLYEGRARIKYRGRATSRLAD-GDRMVMIKTDG
SEQ ID NO:30    MIIKLDENPGTEEVFDFINEAISKRAFIIIVACCRIKYRGRATSRLGS-GDRTIIIKTDG
SEQ ID NO:31    MKLRALENPSAEELESIISEGLSSEAIITIFARCRVYYDGRAKSELGE-GDRVILIKPDG
SEQ ID NO:32    -----KNPDTQRVLEIINEGLSKRAVITIMACCRVDYNGRAVSRLGL-GDRIIIKADG
```

FIG. 7

| | 1 | 10 | 20 | 30 | 40 | 50 | 60 |
|---|---|---|---|---|---|---|---|
| SEQ ID NO:33 | ------IKENPSEEEIKELLDLAEKHGGVVTIFARCKVHYEGRAKSELGE-GDRIIIKPDG | | | | | | |
| SEQ ID NO:34 | MKFLSEKNPDIHRTYEIINEGISKRAFVVLMACCKVLYQGRAKSRLGS-GDRFIIIKPDG | | | | | | |
| SEQ ID NO:35 | MKFLSEKNPDQQRTFEIINEGLSKKRAVIVLMVCCRVIYEGRARSKLAS-GDRMIIIKSDG | | | | | | |
| SEQ ID NO:36 | ------NPDTELVLEIITEGISKRAFITIMASCRVYYEGRATSRLEL-GDRMIILIKSDG | | | | | | |
| SEQ ID NO:37 | ------IKENPSEEEIKELLDLAEKHGGVVTIFARCKVHYEGRAKSELGE-GDRIIILIKKDG | | | | | | |
| SEQ ID NO:38 | MKFKTIENPENNDAYTLLQEGFDKKAMIIVLAECHVEYEGRARSRLDI-GDRLILIKKDG | | | | | | |
| SEQ ID NO:39 | VKFKVEENPSIEKTNELLKDGLKNKAIIITTACCRVFYEGRAKSNLEL-GDRVIIIKPDG | | | | | | |
| SEQ ID NO:40 | VKFKVEENPDIEKTNEILKDGLKNKAIIIITACCRVFYEGRAKSNLEL-GDRVIIIKPDG | | | | | | |
| SEQ ID NO:41 | MKYKTIENPSTQEAYELIKDGFNKKSMIILAQCHVEYEGRARSRLDK-GDRLILIKKDG | | | | | | |
| SEQ ID NO:42 | MKFLSEENPDHQRTFEIINEGLSKKAVVVVACCTVNYDGRARSKLGA-GDRMVMIKSDG | | | | | | |
| SEQ ID NO:43 | MLIEIKHNPSNLESMEIINEALSKRAFLIIVLCCKVNYEGRARSKLGL-GERTVLIKGDG | | | | | | |
| SEQ ID NO:44 | MLLKIEHNPTNLEATELINEAISKRAFMILVVCCKVNYEGRATSKLGF-GERTVLIKGDG | | | | | | |
| SEQ ID NO:45 | MKVKSKENPSVEEVVEILSEGLSNEAIITLFAHCSVFYDGRAKSELGA-GDRVIMIKPDG | | | | | | |
| SEQ ID NO:46 | ------NPDTPRVLEIINEGLSKRAVITIMACCRVDYDGRAVSRLGL-GDRILILIKSDG | | | | | | |
| SEQ ID NO:47 | -KIVVRENPTVEDVKELLEFAEKHNGMVTIFARCRVYYEGRAKSELGE-GDRIIIIKPDG | | | | | | |
| SEQ ID NO:48 | -KVELRENPSPEEIKLLVDSAVSSEGILTIFARCRVHYDGRAKSELGP-GDRVIVKPDG | | | | | | |
| SEQ ID NO:49 | -KVELRENPSPEEIKLLVDSAVSSEGVLTIFARCRVHYDGRAKSELGP-GDRVIIVKPDG | | | | | | |
| SEQ ID NO:50 | -KVELRENPSPEEIKLLVDSAVSSEGVLTIFARCRVHYDGRAKSELGP-GDRVIIVKPDG | | | | | | |
| SEQ ID NO:51 | -KVELRENPSPEEIKLLVDLAISSEGVLTIFARCRVHYDGRAKSELGP-GDRVIIVKPDG | | | | | | |
| SEQ ID NO:52 | -KVELRENPSPEEIKLLVDSAVSSEGVLTIFARCRVHYDGRAKSELGP-GDRVIIVKPDG | | | | | | |
| SEQ ID NO:53 | -KVNYLVNPKAEDIVELLASGIVNDSILVFFAFCRVRYDGRAKSELEP-GDRIIIIKPDG | | | | | | |
| SEQ ID NO:54 | MKVEAKVEPSHEEIIEILDKALSVEAIITLFAYCRVFYEGRAKSELGP-GDRVIIIKPDG | | | | | | |
| SEQ ID NO:55 | MKVEAKVGPSHEEIVEILNKALSVEAIITLFAYCRVFYEGRAKSELGP-GDRIIMIKSDG | | | | | | |
| SEQ ID NO:56 | ------NPDTQRVLDIINEGLSKRAVITIMASCRVYYDGRAVSRLEL-GDRIIMIKPDG | | | | | | |
| SEQ ID NO:57 | -KAEVRMEPTPKELAELFDLARKLEGMLIFARCRVFYDGRAKSELGP-GDRVILIKPDG | | | | | | |
| SEQ ID NO:58 | MKVEAKLNFTYEEIVDIFPNRALSKEAIVNIFAHCRVFYDGRAKSELGP-GDRVIILIKPDG | | | | | | |
| SEQ ID NO:59 | MKVEAKLNPTYEEIVDIFNRALSKEAIVNIFAHCRVFYDGRAKSELGP-GDRIVIKPDG | | | | | | |
| SEQ ID NO:60 | ------ENPTVEEVKELLDIAEKHGGVVTIFARCKVYYEGRAKSELGE-GDRIVIKPDG | | | | | | |
| SEQ ID NO:61 | -KVEAVQNPSRDELMRWVDSALSAEAMLTIFARCKHNGVTIFARCRVYYEGRAKSELGS-GDRIIIIKPDG | | | | | | |
| SEQ ID NO:62 | -VREKPTVEDVKELLEFAEKHNGMVTIFARCRVYYEGRAKSELGE-GDRIIIIKPDG | | | | | | |
| SEQ ID NO:63 | -IKEKPTADEIKELLLDIAEKYGGVITIFARCKVYYEGRAKSELGE-GDRIILIKPDG | | | | | | |
| SEQ ID NO:64 | ------IKEKPTADEIKELLLDIAEKYGGVITIFAKCKVYYEGRAKSELGE-GDRIIIIKPDG | | | | | | |

FIG. 7 (continued)

| | 1 | 10 | 20 | 30 | 40 | 50 | 60 |
|---|---|---|---|---|---|---|---|
| SEQ ID NO:65 | -KVEAVTNPSREELLGIIDSALSKEAMLTIFARCKVHYDGRAKSELGS--GDRVILVKPDG |
| SEQ ID NO:66 | -------NPETQRVLEIINEGLSKRAVITIMASCRVNYDGRAVSRLGV--GDRIILIKSDG |
| SEQ ID NO:67 | MKVEAKLNPSKEEIIDLFSKGLSKEAILTIFAHCKVSYNGRAKSELGP--GDRVIIIKPDG |
| SEQ ID NO:68 | MKVEAKLNPSKEEIIDLFSKGLSKEAIVTIFAHCKVSYNGRAKSELGP--GDRVIIIKPDG |
| SEQ ID NO:69 | MKVEVKLNPSKEEVIDLFSRGLISTEAIVTIFARCNVSYDGRAKSELGL--GDRVIIVKPDG |
| SEQ ID NO:70 | -------NPSPEEIKLLVDSAISSEALLTIFAHCRVYYDGRAKSELGS--GDRVIIVKPDG |
| SEQ ID NO:71 | -KVTVITSPSTEELVSLVNSALLEEAMLTIFARCKVHYDGRAKSELGS--GDRVIIVKPDG |
| SEQ ID NO:72 | -KVTVITSPSTEELVSLVNSALLEEAMLTIFARCKVHYDGRAKSELGS--GDRVIIVKPDG |
| SEQ ID NO:73 | --------PSHEEIIEILDKALSVEAIITLFAYCRVFYEGRAKSQLEE--GDRVIIIKPDG |
| SEQ ID NO:74 | --------LTNPTTKDLENFIDMYVFKY-ILILLARCKVFYEGRAKSELGP--GDRVIIIKPDG |
| SEQ ID NO:75 | --------LTNPTTKDLENFIDMYVFKY-ILILLARCKVFYEGRAKSELEE--GDRIIMIKPDG |
| SEQ ID NO:76 | MKVHFLHKPDIKNLVNFIKEHI-YDSVIILLSRCSVIYDGRAKSTLNE--GDRIIMIKPDG |
| SEQ ID NO:77 | MKVEAKVDPSHEEMVEILDKALSTDAIITLFAYCRVFYEGRAKSELGP--GDRVIIIKPDG |
| SEQ ID NO:78 | MKVEAKVDPSHEEMVEILDKALSTDAIITLFAYCRVFLFGRCRVDYDGRATSTLGP--GDRHVMLKPDG |
| SEQ ID NO:79 | -------ETLSDPDFDAAGDIVERGIDAGALVTLFGRCRVDYDGRATSTLGP--GDRHVMLKPDG |
| SEQ ID NO:80 | -------LSDPDFDAAGDIVERGIDAGALVTLFGRCRVDYDGRATSTLGP--GDRHVMLKPDG |
| SEQ ID NO:81 | -------ETLTYPDPADALDLASRNADRGALVTLVGTCTVEYEGRAASSLGL--GDRHVMLKPDG |
| SEQ ID NO:82 | -------ENPRIEEIKELLEVAESREGLLTIFARCTVYYEGRAKSELGE--GDRIIIIKPDG |
| SEQ ID NO:83 | -------ENPRIEEIKELLEVAESREGLLTIFARCTVYYEGRAKSELGE--GDRIIIIKPDG |
| SEQ ID NO:84 | -------ENPRIEEIKELLEVAESREGLLTIFARCTVYYEGRAKSELGE--GDRIIIIKPDG |
| SEQ ID NO:85 | -------ENPRIEEIKELLEVAESREGLLTIFARCTVYYEGRAKSELGE--GDRIIIIKPDG |
| SEQ ID NO:86 | -------ENPRIEEIKELLEVAESREGLLTIFARCTVFGRCSVEYDGRASSQLDA--GDRHVMCKPDG |
| SEQ ID NO:87 | -------LERPAVETACETVADGIDRDALVTVFGRCSVEYDGRASSQLDA--GDRIITVKPDG |
| SEQ ID NO:88 | --------ITLFAYCRVFVFARCKVVYYEGRAKSELGP--GDRIITVKPDG |
| SEQ ID NO:89 | -------FEKPSIEEVKELFKMAEKHGGVTVFARCKVVYYEGRAKSELGP--GDRIITVKPDG |
| SEQ ID NO:90 | --------LTIFARCRVHYDGRAKSELGS--GDRVILVKPDG |
| SEQ ID NO:91 | --------ITLFAHCSVFYDGRAKSELGA--GDRVIMKPDG |
| SEQ ID NO:92 | --------IILLAQCHVEYEGRARSRLDK--GDRLILIKKDG |
| SEQ ID NO:93 | --------LILLARCRVFYEGRAKSQLEE--GDRVIIIKPDG |
| SEQ ID NO:94 | --------VNIFAHCRVFYDGRAKSELGP--GDRVIIIKPDG |
| SEQ ID NO:95 | --------VTIFARCNVSYDGRAKSELGL--GDRVILVKPDG |
| SEQ ID NO:96 | --------LTIFARCKVHYDGRAKSELGS--GDRVILIKPDG |
| SEQ ID NO:96 | --------VNIFAHCRVFYDGRAKSELGP--GDRVILIKPDG |

FIG. 7 (continued)

```
                     1          10         20         30         40         50         60
                     |          |          |          |          |          |          |
SEQ ID NO:97         ------------------------------------LTIFARCKVHYDGRAKSELGS-GDRVIIIKPDG
SEQ ID NO:98         ------------------------------------VNIFAHCRVFYDGRAKSELGP-GDRVILIKPDG
SEQ ID NO:99         ------------------------------------LTIFARCKVHYDGRAKSELGS-GDRVILVKPDG
SEQ ID NO:100        ------------------------------------LTIFARCKVHYDGRAKSELGS-GDRVIIIKPDG
SEQ ID NO:101        ------------------------------------VTIFAHCKVFYDGRAKSELGP-GDRVIIIKPDG
SEQ ID NO:102        ------------------------------------LTIFARCKVHYDGRAKSELGS-GDRVIIIKPDG
SEQ ID NO:103        ------------------------------------LTIFARCKVHYDGRAKSELGS-GDRVIIIKPDG
SEQ ID NO:104        ------------------------------------LTIFARCKVHYDGRAKSELGS-GDRVIIVKPDG 61         70         80         90         100        110        120
                     |          |          |          |          |          |          |
SEQ ID NO:1          SFLIHQEKKVEPVNWQPPKSKTRGYIQDNNLILESHRRTPKELLTVEIRKVQYITTYANIE
SEQ ID NO:2          SFLIHQEKKVEPVNWQPPKSKTRGYIQDNNLILESHRRTPKELLTVEIRKVQYITYANIE
SEQ ID NO:3          SFLIHQEKKVEPVNWQPPKSKTRGYIQDNNLILESHRRTPKELLTVEIRKVQYITYANIE
SEQ ID NO:4          SFLIHQEKKVEPVNWQPPKSKTRGYIQDNNLILESHRRTPKELLTVEIRKVQYITYANIE
SEQ ID NO:5          SFLIHQEKKVDPVNWQPPKSKTRGYIQDNNLILESHRRTPKELLTVEIRKVQYITYANIE
SEQ ID NO:6          SFLIHQEKKVDPVNWQPPKSRTRSFIRNDKLILESHRRVPKELLSVEIRKIQFINYANVE
SEQ ID NO:7          TFLIHQEKKVEPVNWQPPKSRTRSYIKNDNLFLESHRRTPKELLTVEIRKIQFINYANIE
SEQ ID NO:8          TFLIHQEKKVEPVNWQPPKSRTRSYIKNDNLFLESHRRTPKELLTVEIRKIQFINYANIE
SEQ ID NO:9          SFLIHQDKKVEPVNWQPPKSRTRSYLSGERLILESHRRTPKELLTVEVRQIQFISYANME
SEQ ID NO:10         AFLIHQEKKVEPVNWQPPKSRTRSFIRNDKLILESHRRVPKELLSVEIRKIQFINYANVE
SEQ ID NO:11         SFLIHQERKVDPVNWQPPKSRTRSFIRNDKLILESHRRVPKELLSVEIRKIQFINYANVE
SEQ ID NO:12         SFLIHQERKVDPVNWQPPKSRTRTFIKDNTLFLESHRRSPKERLEVEIKKTHFVNYVLVE
SEQ ID NO:13         SFLIHQDKKVDPVNWQPPKSRSRVLIRNERKLFLESFRRTPREHLEVEIRKIHFLNYALIE
SEQ ID NO:14         CFLIHQDNKVDPVNWQPPKSRPRAYIKDEILFLESHRRSPFFERIEVEIKKVHYANYNLIE
SEQ ID NO:15         CFLIHQDNKVDPVNWQPPKSKTKALIKDETLYLESHRRKPPELLEVEVKKIHYARYNLIE
SEQ ID NO:16         SFLVHQDRKVDPVNWQPPKSRHRALIKENNLILESHRRTPKEKLEVLIEKTFIGTYAVVE
SEQ ID NO:17         SFLVHQERKIDPVNWQPPKSRHRALIKENNLILESHRRTPKEKLEVEIEKVHFASFALAE
SEQ ID NO:18         SFLVHQERKIDPVNWQPPKSRHRALIKENNLILESHRRTPKEKLEVEIEKVHFASFALAE
SEQ ID NO:19         SFLVHQERKIDPVNWQPPKSRHRALIKENNLILESHRRTPKEKLEVEIEKVHFASFALAE
SEQ ID NO:20         SFLIHQNKKVEPVNWQPPKSRTKVYIKNNKLFLESNRKTPRERLEVEINNIETGTYAILE
SEQ ID NO:21         TFMIHQDRKVDPVNWQPPRSRCRSYMKGGKLYLESIRRSPEERLEVEIHEAHLVSCYTAR
```

```
              61          70         80         90        100        110        120
SEQ ID NO:54  SFLIHQKNKREPVNWQPPGSVVSIVLEDGRIMLRSVRRKPKETLEVELIKTYLIVSYFQAE
SEQ ID NO:55  SFLIHQKNKREPVNWQPPGSVVSIVLGDGRIMLRSVRRKPKETLEVELIKTYLIVSYFQAE
SEQ ID NO:56  SFLIHQDRNLEPVNWQPPGPKTKVTVDTHQGMVKIRGVRRSPSESLEVEILQTHLVSYFIGE
SEQ ID NO:57  SFLIHQKKKREPVNWQPPGSKVRLELRNVPTIV-SVRRKPREILEVELLETYMVSAFFAE
SEQ ID NO:58  SFLIHQKEKREPVNWQPPGSSVGLEVKEDKIFLRSIRRKPKEILEVELLNVYLISYFQAE
SEQ ID NO:59  SFLIHQKEKREPVNWQPPGSSVGLEVKEGRIFLRSIRRKPREILEVELLHVYLISYFQAE
SEQ ID NO:60  SFLIHQNKKREPVNWQPPGSKVS--MRENSII--SIRRKPHERLEVELMEVYAVTVFLAE
SEQ ID NO:61  AFLIHQSRKREPVNWQPPGSFVMMEERDGIIVLRSVRRKPKEILEVELEEVYLISLFKAE
SEQ ID NO:62  SFLIHQNKKREPVNWQPPGSVVRVEGNK----VISIRRKPREKLEVELIESYAITVFLAE
SEQ ID NO:63  SFLIHQNKKREPVNWQPPGSSVVRI---SIRRKPREKLEVEVLEAYSGIVFFAE
SEQ ID NO:64  SFLIHQSKKREPVNWQPPGSSVRI---EGNTII-SIRRKPREKLEVEVLEAYSGIVFFAE
SEQ ID NO:65  AFLIHQSKKREPVNWQPPGSFVTVEERDGIIVLRSVRRKPKEILEVELEEVYLASLFKAE
SEQ ID NO:66  SFLIHQDRNLEPVNWQPPGPKTKVTVETYQGMVKIRGVRRNPSESLEVELLQTHLASYFIGE
SEQ ID NO:67  SFLIHQKEKREPVNWQPPGSSPSLSAGEDKLILKSVRRKPKETLEVELIDVYLFSYFQAE
SEQ ID NO:68  SFLIHQKEKREPVNWQPPGSSPSLSAGEDKLILKSVRRKPKETLEVELIDVYLFSYFQAE
SEQ ID NO:69  SFLIHQKEKREPVNWQPPGSSVSLKIGEDKLILRSVRRKPKEILEVGLIDVYLLSYFQAE
SEQ ID NO:70  SFLIHQSKKREPVNWQPPGSVVHVELREKPVLV-SVRRKPPETLEVELEEVLITVFHAE
SEQ ID NO:71  SFLIHQSKKREPVNWQPPGSRVRLELRENPVLV-SIRRKPRETLEVELEEVYMVSVFRAE
SEQ ID NO:72  SFLIHQSKKREPVNWQPPGSRVRLELRENPVLV-SIRRKPRETLEVELEEVYMVSVFRAE
SEQ ID NO:73  SFLIHQKNKREPVNWQPPGSVVSIVLEDGRIMLRSVRRKPKETLEVELIKTYLVSYFQAE
SEQ ID NO:74  AFLIHKDKKREPVNWQPSGSSIIWEVEDNEFILKSIRRKPKEELKVVISEVYHACAFNCE
SEQ ID NO:75  AFLIHKDKKREPVNWQPSGSSIIWEVEDNFFILKSIRRKPKEELKVVISEVYHACAFNCE
SEQ ID NO:76  SLLIHKNKKREPVNWQPSGSSISYKIENKQFIIRSIRRKPREVLEIIVYEVYHACAFKCE
SEQ ID NO:77  SFLIHQKNKREPVNWQPPGSAVSIVLEDGKIMLRSVRRKPKETLEVELIKTYLVSYFQAE
SEQ ID NO:78  SFLIHQKNKREPVNWQPPGSAVSIVLEDGKIMLRSVRRKPKETLEVELIKTYLIVSYFQAE
SEQ ID NO:79  AALVHTDEGQQPVNWQPPGCEHAVRVVDGEFVVESERSSPDELLSIAFESLSHVGVFDVT
SEQ ID NO:80  AALVHTDEGQQPVNWQPPGCEHAVRVVDGEFVVESERSSPDELLSIAFESLAHVGVFDVT
SEQ ID NO:81  AALVHTDEGQQPVNWQPPGCEHSISVDDGSLVVRSTSTPEELLEVTFETVAHAAAFDVT
SEQ ID NO:82  SFLIHQKKKREPVNWQPPGSKVKMEGNS----LISIRRNPKETLKVDIIEAYAAVLFMAE
SEQ ID NO:83  SFLIHQKKKREPVNWQPPGSKVKMEGNS----LISIRRNPKETLKVDIIEAYAAVLFMAE
SEQ ID NO:84  SFLIHQKKKREPVNWQPPGSKVKMEGNS----LISIRRNPKETLKVDIIEAYAAVLFMAE
SEQ ID NO:85  SFLIHQKKKREPVNWQPPGSKVKMEGNS----LISIRRNPKETLKVDIIEAYAAVLFMAE
```

FIG. 7 (continued)

```
                   61         70         80         90        100        110        120
                    |          |          |          |          |          |          |
SEQ ID NO:86   TTLVHTDEGQQPVNWQPPGCTHEVFCDDGALFLESHRSTPQERLLIGFERVVHVSVFPVS
SEQ ID NO:87   SFLIHQKNKREPVNWQPPGSVVSIVLGDGRIMLRSVRRKPKETLEVELIKTYLVSYFQAE
SEQ ID NO:88   TFLIVHQNKKREPVNWQPPGSIVSIEGNS----IISIRRKPREKLEVELIDVYAVVVFLAE
SEQ ID NO:89   AFLIVHQSKKREPVNWQPPGSFVTVEVREGLVVLRSVRRKPKEILEVELEEVYLASLFNAE
SEQ ID NO:90   TFLIHQEKERVPVNWQPPGSIVSFQIEEGKIKLRSVRRKPKEILEVELLKVYLISYFQAE
SEQ ID NO:91   TFTIHQELNLDPVNWQAPGCKNKVSLKENQIILQSIKTKPDEEITVYLDTVYCATYYNCV
SEQ ID NO:92   TFLIHKDDKKREPVNWQPPGSNIIWKVEDNYFILKSIRRKPKEELKVVISEVYHTCAFNCE
SEQ ID NO:93   SFLIHQKEKREPVNWQPPGSSVGLEINDGKLFLRSVRRKPREILEVELLNVYLLISYFQAE
SEQ ID NO:94   SFLIHQKEKREPVNWQPPGSVVSLKIGEDKLILRSVRRKPKEILEVGLIDVYLLSYFQAE
SEQ ID NO:95   AFLIHQKEKREPVNWQPPGSFVTVEERDGIIVLRSVRRKPKEILEVELEEVYLASLFKAE
SEQ ID NO:96   SFLIHQKEKREPVNWQPPGSSVGLEVKEGRIFLRSIRRKPREILEVELLHVYLISYFQAE
SEQ ID NO:97   AFLIHQKEKREPVNWQPPGSFVMMEERDGILVLRSVRRKPKEILEVELEEVYLLISYFKAE
SEQ ID NO:98   SFLIHQKEKREPVNWQPPGSSVGLEVKEDKIFLRSIRRKPKEILEVELLNVYLLISYFQAE
SEQ ID NO:99   AFLIHQSKKREPVNWQPPGSFVTVEERDGIIILRSVRRKPKEILEVELEEVYLVSLFKAE
SEQ ID NO:100  AFLIHQSKKREPVNWQPPGSFVTVEERDGIIILRSVRRKPKEILEVELIDVYLFSYFQAE
SEQ ID NO:101  SFLIHQKEKREPVNWQPPGSSVSLDVKEDKLILRSVRRKPKEILEVELEEVYLVSLFKAE
SEQ ID NO:102  AFLIHQSKKREPVNWQPPGSFVTIEERDGIIILRSVRRKPKEILEVELEEVYLVSLFKAE
SEQ ID NO:103  SFLIHQSKKREPVNWQPPGSRVRLELRENPVLV-SIRRKPRETLEVELEEVYMVSVFRAE
SEQ ID NO:104  SFLIHQSKKREPVNWQPPGSRVRLELRENPVLV-SIRRKPKETLEVELEEVYMVSVFRAE 121        130        140        150        160        170        180
                    |          |          |          |          |          |          |
SEQ ID NO:1    DFEELELEQAGYEKDMGDMIM-EKPHMIEEGFKPTAREYSVEHGFIDILGKDCDNNLMILEL
SEQ ID NO:2    DFEELEQAGYEKDMGDMIM-EKPHMIEEGFKPTAREYSVEHGFIDILGKDCDNNLMILEL
SEQ ID NO:3    DFEELEQAGYEKDMGDMIM-EKPHMIEEGFKPTAREYSVEHGFIDILGKDRDNNLMILEL
SEQ ID NO:4    DFEELEQAGYEKDMGDMIM-KKPHMIEEGFKPTAREYSVEHGFIDILGKDRDNNLMILEL
SEQ ID NO:5    DFEELEQAGYEKDMGDMIM-EKPHMIEEGFKPTAREYSVEHGFIDILGKDRDNNLMILEL
SEQ ID NO:6    DFEELEQAGYEKDMGDMIM-DKPHLIEEGFTPTAREYSVEHGFIDILGKDRDNNLMILEL
SEQ ID NO:7    DFEELEQAGYEKDMGDMIM-EKPHMIEEGFTPTAREYSVEHGFIDILGKDRDNNLMILEL
SEQ ID NO:8    DFEELEQAGYEKDMGDMIM-EKPHMIEEGFTPTAREYSVEHGFIDILGKDSDNNLMVLEL
SEQ ID NO:9    DFEELEQAGYEKDMSDMIM-ERPHLIEEGFTPKTREYSVEHGFIDILGKDNDGNLMVLEL
SEQ ID NO:10   DFEELEQAGYEKDMSDMIM-EKPHLIEEGFTPTTREYSVEHGFIDILGKDSDNNLMVLEL
```

```
              130       140       150       160       170       180
      121      |         |         |         |         |         |
SEQ ID NO:43   DTKDIELAGYEEDMRHMIM-NNPDLIEKGFRPTSKEYQTPQGFIDIYGKDANGKIVIEL
SEQ ID NO:44   DTKDIELAGYEEDMRQMIM-DNPELIEKGFRPTSKEYQTPQGFIDILGKDDAGKIVVLEL
SEQ ID NO:45   DYEALNLMGSEAEMADLIL-QNPSIIEEGFKALQKEKPIKHGIIDIYGVDRDGNIVILEL
SEQ ID NO:46   DSESLELAGYEANMGDLIF-KDPEVFEKGFRPTSREYHTPQGFTDILGKDQDGNITILEL
SEQ ID NO:47   DYEELSLTGSEAEMAKLIF-EKPEVIEEGFKPMFKEKPIKHGIVDILGVDREGNVVVLEL
SEQ ID NO:48   DYEELALTGSEAEMAELIF-ENPEVIEFGFKPLYREKPIKHGIVDILGVDREGNIVVLEL
SEQ ID NO:49   DYEELALTGSEAEMAELIF-ENPEVIEPGFKPLYREKPIKHGIVDVLGVDRDGNLVVLEL
SEQ ID NO:50   DYEELALTGSEAEMAELIF-ENPEVIEPGFKPLYREKPIKHGIVDVLGVDKDGNLVVLEL
SEQ ID NO:51   DYEELALTGSEAEMAELIF-ENPEVIELGFKPLYREKPIRHGIVDVLGVDRDGNLVVLEL
SEQ ID NO:52   DYEELALTGSEAEMAELIF-ENPEVIEPGFKPLFKEKQINHGIIDILGKDKSGRWVIEL
SEQ ID NO:53   DYEELSLTGSEAEMADLIF-ENPSLIEDGFKPLFKEKPIKHGIVDVLGKDKHGNLVVLEL
SEQ ID NO:54   DYEELTLTGSEAEMADLIF-ENPSLIEEGFKPLFKEKPIKHGIVDVLGKDKHGNLVVLEL
SEQ ID NO:55   DYEEITLTGSEAEMADLIF-ENPSLIEEGFKPLFKEKPIKHGIVDVLGKDKHGNLVVLEL
SEQ ID NO:56   DYEELAGYEANMGDLIF-KDPEVIEKGFRPTSREYHTPQGFIDVLGKDQNGNITILEL
SEQ ID NO:57   DYEALKLSGSEAEMAALIF-SNPDVIEPGFKPLFREKPVRHGIVDVLGVDKEGNLVVLEL
SEQ ID NO:58   DYEELALTGSEAEMADLIF-ENPSLIEDGFKPLFKEKPIKHGIVDVLGVDKEGNIVILEL
SEQ ID NO:59   DYEELALTGSEAEMADLIF-ENPSVIEDGFKPLFKEKPIKHGIVDVLGVDKEGNIVVLEL
SEQ ID NO:60   DYEELALTGSEAEMAELIF-ENPNVIEEGFKPMFREKQIKHGIVDIMGLDKDGNIVVLEL
SEQ ID NO:61   DYEELALTGSEAEMAEMVF-RNPELIEEGFKPLFREKQIGHGIVDILGRDRDGNLVVLEL
SEQ ID NO:62   DYEELSLTGSEAEMAKLIF-EKPEVIEEGFKPMFKEKPIKHGIVDILGIDREGNVVVLEL
SEQ ID NO:63   DYEELALTGSEAEMAELIF-QNPDIIEKGFKPLFREKPIKHGIVDILGVDKEGNIVVLEL
SEQ ID NO:64   DYEELALTGSEAEMAELIF-QNPDIIEKGFKPLFREKPIKHGIVDILGVDKEGNIVVLEL
SEQ ID NO:65   DYEELALTGSEAEMAEMIF-KNPELIEEGFKPLFREKSIGHGIVDVLGVDREGNLVVLEL
SEQ ID NO:66   DVESLELAGYEANMGDLIF-KDPEVVERGFRPTSREYHTPQGFIDILGKDQNGNITILEL
SEQ ID NO:67   DYETTLALMGSEAEMADLIF-ENPELIEDGFKPLFKEKSIRHGIVDILGKDKNGNIVVLEF
SEQ ID NO:68   DYETLALMGSEAEMADLVF-ENPELIEDGFKPLFKEKSIKHGIVDILGKDKNGNIVVLEF
SEQ ID NO:69   DYEELALTGSEAEMAELIF-ENPELIEPGFKPIFKEKSIRHGIIDILGKDKDGNIVVLEL
SEQ ID NO:70   DYEELALTGSEAEMADLIF-EQPEVIEPGFKPLYREKPVKHGIVDVLGVDREGNLVVLEL
SEQ ID NO:71   DYEELALTGSEAEMAELIF-ENPEVIEPGFKPLFREKAIGTGIVAVLGRDSDGNLVVLEL
SEQ ID NO:72   DYEELTLTGSEAEMADLIF-ENPSLIEEGFKPLFKEKPIKHGIVDVLGKDKHGNLVVLEL
SEQ ID NO:73   DYEEINLRGSESEMAEMIF-RNPDLIEEGFKPISREYQIPTGIVDILGKDKENKWVILEL
```

FIG. 7 (continued)

```
                    121                 130                 140                 150                 160                 170                 180
                      |                   |                   |                   |                   |                   |                   |
SEQ ID NO:75    DYEEINLRGSESEMAEMIF-RNPDLIEEGFKPISREYQIPTGIVDILGKDKENKWVILEL
SEQ ID NO:76    DYEELNLTGSEGDMVDMIF-RNPKLIEEGFKPLSKEYQIPTGIIDILGKDENNNWVILEL
SEQ ID NO:77    DYEELALTGSEAEMADLIF-ENPSLIEEGFKPLFKEKPIKHGIVDKDKHGNLVVLEL
SEQ ID NO:78    DYEELALTGSEAEMADLIF-ENPSLIEEGFKPLFKEKPIKHGIVDVLGRDKHGNLVVLEL
SEQ ID NO:79    DATDLSLTGTEEDLRERIL-DDPDLLEPAFTPLATERSTPAGAIDIYGEDADGRTVVEL
SEQ ID NO:80    DATDLSLTGTEADLRERIL-DDPDLLEPAFTPLATERSTPAGAIDIYGEDADGRTVVVEL
SEQ ID NO:81    DSKDLALTGTEADLKDRIL-DEPGLVESGFTPLATERETPAGAVDIYGEDADGRTTILEL
SEQ ID NO:82    DYEELTLTGSEAEMAELIF-QNPNVIEEGFKPMFREKPIKHGIVDVLGVDREGNIVVLEL
SEQ ID NO:83    DYEELTLTGSEAEMAELIF-QNPNVIEEGFKPMFREKPIKHGIVDVLGVDREGNIVVLEL
SEQ ID NO:84    DYEELALTGSEAEMADLIF-QNPNVIEEGFKPMFREKPIKHGIVDVLGVDREGNIVVLEL
SEQ ID NO:85    DYEELALTGSEAEMAELIF-QNPNVIEEGFKPMFREKPIKHGIVDVLGVDREGNIVVLEL
SEQ ID NO:86    DSSELTLVGTEEDLRQRIL-EDPGLLEPGFRPLATERDTPAGAIDIYGEDSVGRAVVVEL
SEQ ID NO:87    DYEELTLTGSEAEMADLIF-ENPSLIEEGFKPLFKEKPIKHGIVDVLGKDKHGNLVVLEL
SEQ ID NO:88    DYEELALTGSEAEMAKLIF-ENPEVIEEGFKPMFREKPIKHGIVDIMGVDKNGNIVILEL
SEQ ID NO:89    DYEELALTGSEAEMADLIL-ENPSLIEEGFKPLFREKQIGHGIVDILGKDGRGNIVVLEL
SEQ ID NO:90    DYEALNLMGSEAEMAELIF-QNPSIIEEGFKALQKEKPIKHGIIDIYGVDRDGNIVVLEL
SEQ ID NO:91    DTKNLEIRGYEKHMVDLAW-EKPELIEKGFRPTRREYQTENGFIDLMGTDKDEKLMILEF
SEQ ID NO:92    DYEELNLTGSESEMAEMIF-RNPNLIEEGFKPLSREYQIPTGIIDILGKDKDERWVILEL
SEQ ID NO:93    DYEELALTGSEAEMADLIF-EDPSLIEAGFKPLFREKPIKHGIVDVLGVDKEGNIVILEL
SEQ ID NO:94    DYESLALMGSEAEMADLVF-ENPELIEPGFKPLFREKSIRHGIGHGIVDILGKDREGNIVILEL
SEQ ID NO:95    DYEELALTGSEAEMAEMIF-KNPELIEPGFKPLFREKSIGHGIVDILGRDREGNLVVLEL
SEQ ID NO:96    DYEELALTGSEAEMAEMIF-RNPELIEPSVIEDGFKPIKHGIVDVLGVDKEGNIVILEL
SEQ ID NO:97    DYEELALTGSEAEMAEMVF-RNPELIEPGFKPLFREKQIGHGIVDILGRDRDGNLVVLEL
SEQ ID NO:98    DYEELALTGSEAEMADLVF-ENPSLIEDGFKPLFKEKPIKHGIVDVLGVDKEGNIVILEF
SEQ ID NO:99    DYEELALTGSEAEMAEMIF-KNPELIEPGNPELIEPGFKPLFREKQIGHGIVDILGRDKNGNLVVLEL
SEQ ID NO:100   DYEELALTGSEAEMAEMIF-GNPELIEPGFKPLFREKQIGHGIVDILGRDKNGNLVVLEL
SEQ ID NO:101   DYEALALVGSEAEMADLVF-ENPELIEDGFKPLFKEKSIRHGIVDLLGKDGNIVILEF
SEQ ID NO:102   DYEELALTGSEAEMAELIF-RNPELIEPGFKPLFREKPIKHGIVDILGRDGDGNLVVLEL
SEQ ID NO:103   DYEELALTGSEAEMAELIF-ENPEVIEPGFKPLFREKAIGTGIVDILGRDSDGNIVVLEL
SEQ ID NO:104   DYEELTLTGSEAEMAELIF-ENPEVIEPGFKPLFREKTIKSGIVDILGRDSNGNIVVLEL
```

FIG. 7 (continued)

```
          181       190       200       210       220       230       240
            |         |         |         |         |         |         |
SEQ ID NO:1   KARKAGVSAVKQLKRYLTDFEDDDNDYLKECLVQKKIRGLLVAPSLGEDAKELIEKEGI
SEQ ID NO:2   KARKAGVSAVKQLKRYLTDFEDGDNDYLKECLVQKKIRGLLVAPSLGEDAKELIEKEGI
SEQ ID NO:3   KARKAGVSAVKQLKRYLTDFEDDDNDYLKECRVQKKIRGLLVAPSLGNDAELLEKEGI
SEQ ID NO:4   KARKAGVSAVKQLKRYLTDFEDDDNDYLKECRVQKKIRGLLVAPSLGNDAEELLEKEGI
SEQ ID NO:5   KARKAGVSAVKQLKRYLTDFEDDDNDYLKECRVQKKIRGLLVAPSLGNDAEELLEKEGI
SEQ ID NO:6   KARKAGVSAVKQLKRYLSDFENTENDYLKECASKKRIRGLLVAPSLGEDAKEMIEDEGI
SEQ ID NO:7   KARKAGITAVKQLRRYLQDLENTDNDYLKECESQKKKIRGLLVAPSIMDDALELLENEGI
SEQ ID NO:8   KARKAGITAVKQLRRYLQDLENTDNDYLKECESQKKKIRGLLVAPSIMDDALELLENEGI
SEQ ID NO:9   KARKAGVSAVKQIRRYLQDLENTENDYLKECKAQKKIRGILVAPSIMEDAREMIEEEGI
SEQ ID NO:10  KARKAGVAAVKQLRRYLQDLENTDNDYLKECKAQKKIRGLLVAPSIMDDALELIEEEGI
SEQ ID NO:11  KARKAGVSAVKQLKRYLSDFENTENDYLKECKASKKRIRGLLVAPSLGEDAKEMIEDEGI
SEQ ID NO:12  KCRKAGINAVKQIRRYLTDFKEEENSNLENTGNEKKKVRGLLVAPSLGEDARELLEERNI
SEQ ID NO:13  KSRKIGVNAVKQIRRYLSDFEDERNSYLKDLGVEKKKIRGLLVAPKIDEDAKEMIEEEGI
SEQ ID NO:14  KSRKAGITAVKQIRRYLTDFENKENSEIKAKNGQKQKIRGLLVAPSIGDDALELLEEEGI
SEQ ID NO:15  KARKAGITAVKQIRRYLTDFENRENKEIRHEE-EKQKVRGLLVAPSIGDDALELLEEEGI
SEQ ID NO:16  KSRKIGISAVKQIKRYIDDLITNTENRSLR-LGVEKKKIRGLLVGPKIDEDAKEMIEEGI
SEQ ID NO:17  KCRKAGTNAVKQIRRYLKDFEENDNDYLKEIKSKKKKIRGLLVAPDINEDAKELLEEEGI
SEQ ID NO:18  KCRKAGTNAVKQIRRYLKDFEENDNDYLKEIKSKKKKIRGLLVAPDINEDAKELLEEEGI
SEQ ID NO:19  KCRKAGINAVKQIRRYLKDFEENDNDYLKEVKSKKKKIRGLLVAPDINEDAKEMIEEEGI
SEQ ID NO:20  KSRKIGVSAVKQIRRYVEDLKNTENKEFE-TDNNKKRIRGILVAPKIDNDAKEMIEEENF
SEQ ID NO:21  KSRKAGVSAVKQLKRYLDEFRDDR-------RGVRGMLVAPSITHDAMEMLEDEGL
SEQ ID NO:22  KSRRAGVSAVRQLKRYLEDFKDDK-------HGVRGVLVAPSITHDARELLEAEGL
SEQ ID NO:23  KSRKAGVSAVKQLKRYVDEFREDR-------VGVRGVLVAPSITHDAMEMLEEEGL
SEQ ID NO:24  KSRKAGVSAVKQLKRYVDEFREDR-------VGVRGVLVAPSITHDAMEMLEEEGL
SEQ ID NO:25  KSRKAGVSAVKQLKRYVDEFRDDR-------VGVRGILVAPSITHDALEMLEDEGL
SEQ ID NO:26  KSRRAGLNAVKQLRRYLKDFKDDK-------HGVRGVLVAPSITHDAKELLEKEGL
SEQ ID NO:27  KSRKAGLNAVKQLRRYVDEFRDDQ-------VGVRGILVAPSITHDALEMLEDEGL
SEQ ID NO:28  KSRRAGINAVKQLRRYLKDFKDDK-------DFVRGLLVAPSITEDAQELLEKYQL
SEQ ID NO:29  KSRQAGVNAVKQLKKYFEDFTDHK-------QFVRGLLVAPSVTEDAQELLEKYQL
SEQ ID NO:30  KSRRADLHAVSQLKRYVEDMREEY-------DFVRGLLVAPSVTDDASDLLKEYKL
SEQ ID NO:31  KRRRADLHAVSQLKRYVEDMREEY-------ENVRGILVAPSLFSGAKKLLEKEGL
SEQ ID NO:32  KSRKAGVNAVKQLRRYLDCFSDHK-------EKVRGVLVAPSATDDALELLEKQGM

FIG. 7 (continued)
```

```
              181       190       200       210       220       230       240
SEQ ID NO:33  KRRKADLHAVSQLKRYVDSLKEEYG---------------ENVRGILVAPSLTEGAKKLLEKEGL
SEQ ID NO:34  KSRRAGVNAVKQLKKYLDCFTDHK---------------EFVRGVLVAPSVTDDAMELLKEYQL
SEQ ID NO:35  KSRRAGINAVKQLKKYLDCFSDHK---------------EFVRGILVAPSITGDAEELLEEYKL
SEQ ID NO:36  KSRKAGTNAVKQLRRYVDCFCDHK---------------EKVRGVLVAPSATDDALEMLEEQGM
SEQ ID NO:37  KRRKADLHAVSQLKRYVDSLKEEYG---------------ENVRGILVAPSLTEGAKKLLEKEGL
SEQ ID NO:38  KSRKAGTNAVKQLKGYIDCFKDNK---------------EFVRGILVAPDITDNARELLESLQM
SEQ ID NO:39  KRVRGSLGAVSQLKRYVDNLKEEN---------------EGLRGMLVAPSITDSAMKLLKEYGL
SEQ ID NO:40  KRVRGSLGAVSQLKRYVDNLKEEN---------------EGLRGMLVAPSITDSAMKLLKEYGL
SEQ ID NO:41  KSRKAGTNAVKQLKGYVECFMDNK---------------EFVRGILVAPDITDNALELLKSLQM
SEQ ID NO:42  KSRRAGINAVKQLKRYLDDFSDHK---------------EFVRGILVAPSVTDDAAELLEGFKL
SEQ ID NO:43  KSRKAGINAVKQLKRYINCFLDNK---------------EFVRGILVAPSITDDARELLENNKM
SEQ ID NO:44  KSRKAGVNAVKQLLRYVDCFSDNK---------------EFVRGILVSPSITEEAKEILNEYQM
SEQ ID NO:45  KRRRADLHAVSQLKRYVDALKEEH---------------GSVRGILVAPSLTSGAEKLLKDLGL
SEQ ID NO:46  KSRKAGTNAVKQLRRYVDCFSDHK---------------EKVRGVLVAPSATDDALELLEEQGM
SEQ ID NO:47  KRRRADLHAVSQLKRYVDSLKEEYG--------------DKVRGILVAPSLTEGARKLLEKEGL
SEQ ID NO:48  KRRRADLHAVSQLKRYVETLREEH---------------ENVRGILVAPSLTSGAKKLLEKEGL
SEQ ID NO:49  KRRRADLHAVSQLKRYVETLREEH---------------ENVRGILVAPSLTSGAKKLLEKEGL
SEQ ID NO:50  KRRRADLHAVSQLKRYVETLREEH---------------ENVRGILVAPSLTSGAKKLLEKEGL
SEQ ID NO:51  KRRRADLHAVSQLKRYVETLREEH---------------ENVRGILVAPSLTSGAKKLLEKEGL
SEQ ID NO:52  KRRRADLHAVSQLKRYVETLREKH---------------ENVRGILVAPSLTSGARKLLEKEGL
SEQ ID NO:53  KRRRADLQAVSQLKRYVECLKYEYGE-------------GNIRGILVAPSLTSGAKKLLEEENL
SEQ ID NO:54  KRRRADLHAVSQLKRYVDSLREEH---------------KNVRGILVAPSLTAGAKKLLEKEGL
SEQ ID NO:55  KSRKAGVNAVQLRRYVDCFSDHK----------------KNVRGILVAPSLTAGAKKLLEKEGL
SEQ ID NO:56  KRRRADLHAVSQLKRYVDCFSDHK---------------DTVRGVLVAPSITDDARELLEEQKM
SEQ ID NO:57  KSRKAGVNAVQLRRYVEALREENPG--------------KIVRGILVAPSITAGAQRLLEKEGL
SEQ ID NO:58  KRRRADLHAVSQLKRYVEAMREEH---------------EKVRGILVAPSLTSGAKKLLEKEGL
SEQ ID NO:59  KRRRADLHAVSQLKRYVEAMKEEH---------------EKVRGILVAPSLTSGAKKLLEKEGL
SEQ ID NO:60  KRRRADLHAVSQLKRYVDSLKEEYG--------------EKVRGILVAPSLTEGAKKLLEKEGL
SEQ ID NO:61  KRRKADLHAVSQLKRYVEALKREH---------------ETVRGILVAPSLTAGAKKLLEKEGL
SEQ ID NO:62  KRRRADLHAVSQLKRYVDALKEEYG--------------ERVRGILVAPSLTEGARKLLEKEGL
SEQ ID NO:63  KRRRADLHAVSQLKRYVESLKEEY---------------KRKVRGILVAPSLTEGARKLLEKEGL
SEQ ID NO:64  KRRRADLHAVSQLKRYVESLKEEY---------------KRKVRGILVAPSLTEGARKLLEKEGL
```

FIG. 7 (continued)

```
              181       190       200       210       220       230       240
                |         |         |         |         |         |         |
SEQ ID NO:65    KRRRADLHAVSQLKRYVEALRAEH---------------------PAVRGILVAPSLTSGAKKLLEKEGL
SEQ ID NO:66    KSRRKAGINAVKQLKRYVDCFSDHK-------------------EAVRGVLVAPSITDDARQLLEEQKM
SEQ ID NO:67    KRRRADLHAVSQLKRYVETIKEEY--------------------KNVRGILVAPSLTSGAKRLLEKEGL
SEQ ID NO:68    KRRRADLHAVSQLKRYVETIKEEY--------------------KNVRGILVAPSLTSGAKRLLEKEGL
SEQ ID NO:69    KRRRADLHAVSQLKRYVETMREEY--------------------KNVRGILVAPSLTSGAKRLLEKEGL
SEQ ID NO:70    KRRRADLHAVSQLKRYVETLKEEH--------------------GNVRGILVAPSLTSGARKLLEKEGL
SEQ ID NO:71    KRRRAELHAVRQLKSYVEILREEYG-------------------DKVRGILVAPSLTSGAKRLLEKEGL
SEQ ID NO:72    KRRRAELHAVRQLKSYVEILREEYG-------------------DKVRGILVAPSLTSGAKRLLEKEGL
SEQ ID NO:73    KRRRADLHAVSQLKRYVDSLREEH--------------------KNVRGILVAPSLTAGAKKLLEKEGL
SEQ ID NO:74    KRRRADLQAVSQLKRYVEYFKNKYGE------------------DKVRGILVSPSLTTGAEKLLKEENL
SEQ ID NO:75    KRRRADLQAVSQLKRYVEYFKNKYGE------------------DKVRGILVSPSLTTGAEKLLKEENL
SEQ ID NO:76    KRRRADLQSVSQLKRYVEYFKSKYGE------------------KRVRGILVAPSLTTGALNLLKSENL
SEQ ID NO:77    KRRRADLHAVSQLKRYVDALREEH--------------------KNVRGILVAPSITAGAKKLLEKEGL
SEQ ID NO:78    KRRRADLHAVSQLKRYVDALREEH--------------------KNVRGILVAPSLTAGAKKLLEKEGL
SEQ ID NO:79    KRRRVGPDAVGQLDRYVQALGRDLHD------------------EAEIRGLIVAPSVTDRARELLAQKGL
SEQ ID NO:80    KRRRVGPDAVGQLDRYVQALGRDLHD------------------EAEIRGLIVAPSVTDRARELLAQKGL
SEQ ID NO:81    KRRRVGPDAVGQLGRYVDALERDLHA------------------DTEVRGILVAPSVTDRARQLLAEKGL
SEQ ID NO:82    KRRRADLHAVSQLKRYVDALKEEHG-------------------NKVRGILVAPSLTEGAKKLLEKLGL
SEQ ID NO:83    KRRRADLHAVSQLKRYVDALKEEHG-------------------NKVRGILVAPSLTEGAKKLLEKLGL
SEQ ID NO:84    KRRRADLHAVSQLKRYVDALKEEHG-------------------NKVRGILVAPSLTEGAKKLLEKLGL
SEQ ID NO:85    KRRRADLHAVSQLKRYVDALKEEHG-------------------NKVRGILVAPSLTEGAKKLLEKLGL
SEQ ID NO:86    KRRRADLHAVSQLRRYVDSLREEH--------------------DASIRGILVAPSVTDRASGLIGEHGL
SEQ ID NO:87    KRRKADLHAVSQLKRYVDALKEEYG-------------------KNVRGILVAPSLTSGAKKLLEKEGL
SEQ ID NO:88    KRRKADLHAVSQLKRYVEALEREH--------------------ERVRGILVAPSLTEGAKKLLEKEGL
SEQ ID NO:89    KRRRADLHAVSQLKRYVDALKEEH--------------------GKVRGILVAPSLTSGAKKLLEKEGL
SEQ ID NO:90    KRRRADLHAVSQLKRYVDALKEEH--------------------GSVRGILVAPSLTSGAEKLLKDLGL
SEQ ID NO:91    KSRKAGTNAVKQLKGYVECFMDNK--------------------EFVRGIIVAPDITDNALELLKSLQM
SEQ ID NO:92    KRRRADLQAVSQLRRYVEYFKSKYG-------------------RDRVRGILVAPSLTVGAERLLKEENL
SEQ ID NO:93    KRRRADLHAVSQLKRYVEAMREEH--------------------EKVRGILVAPSLTSGAKKLLEKEGL
SEQ ID NO:94    KRRRADLHAVSQLKRYVETMREEY--------------------KNVRGILVAPSLTSGAKRLLEKEGL
SEQ ID NO:95    KRRRADLHAVSQLKRYVEALRAEH---------------------PAVRGILVAPSLTSGAKKLLEKEGL
SEQ ID NO:96    KRRRADLHAVSQLKRYVEAMKEEH--------------------EKVRGILVAPSLTSGAKKLLEKEGL
```

FIG. 7 (continued)

```
              181       190       200       210       220       230       240
               |         |         |         |         |         |         |
SEQ ID NO:97   KRRRKADLHAVSQLKRYVEALKREH--------------ETVRGILVAPSLTAGAKKLLEKEGL
SEQ ID NO:98   KRRRADLHAVSQLKRYVEAMREEH--------------EKVRGILVAPSLTSGAKKLLEKEGL
SEQ ID NO:99   KRRRADLHAVSQLKRYVEALRAEH--------------PAVRGILVAPSLTSGAKKLLEKEGL
SEQ ID NO:100  KRRRKADLHAVSQLKRYVEGLSKEH--------------EGVRGILVAPSLTSGAKKLLEKEGL
SEQ ID NO:101  KRRRKADLHAVSQLKRYVETMREEY--------------EKVRGILVAPSLTSGARRLLEKEGL
SEQ ID NO:102  KRRRKADLHAVSQLKRYVEALSREH--------------ESVRGILVAPSLTSGAKRLLEKEGL
SEQ ID NO:103  KRRRAELHAVRQLKSYVEILREEYG--------------DKVRGILVAPSLTSGAKRLLEKEGL
SEQ ID NO:104  KRRRAELHAVRQLKSYVEILKEEYG--------------DKVRGILVAPSLTSGAKRLLEKEGL 241       250       260       270       280       290       300
               |         |         |         |         |         |         |
SEQ ID NO:1    EFVAVNPPK--ELKRD-KKVTLDAF
SEQ ID NO:2    EFVAVNPPK--ELKRD-KKVTLDAF
SEQ ID NO:3    EFVAVEPPK--ELKRD-KKVTLDIF
SEQ ID NO:4    EFVAVEPPK--ELKRD-KKVTLDAF
SEQ ID NO:5    EFVAVEPPK--ELKRD-KKVTLDAF
SEQ ID NO:6    EFVSIEPPK--ELKRD-KKVTLDAF
SEQ ID NO:7    EFVSIEPPK--ELKRD-KKTTLDAF
SEQ ID NO:8    EFVSIEPPR--ELKRD-KKVTLDAF
SEQ ID NO:9    EFVSIEPPR--ELKRD-KKVTLDAF
SEQ ID NO:10   EFVSVEPPR--ELKRD-KKVTLDAF
SEQ ID NO:11   EFVSIEPPK--ELRRDKK-------
SEQ ID NO:12   EFKSIDPPK--ELKND-KKVTLDIF
SEQ ID NO:13   EFVSLEPPK--ELKRD-KLVTLDSF
SEQ ID NO:14   EFVSVEPPK--ELKKD-KRVTLDSF
SEQ ID NO:15   EFVSVEPPR--ELKRD-KKTTLDSF
SEQ ID NO:16   EFVECEPPK--ELKRD-KKTTLDSF
SEQ ID NO:17   EFKAVDPPK--ELKSD-KKVTLDIF
SEQ ID NO:18   EFKAVDPPK--ELKSD-KKVTLDIF
SEQ ID NO:19   EFKAVDPPK--ELRSD-KKVTLDIF
SEQ ID NO:20   EFVACEPPK--ELKKD-KKVTLDLF
SEQ ID NO:21   EFRSLEPLR--ELRSA-RGVTLDNF
```

FIG. 7 (continued)

```
          241       250       260       270       280       290       300
           |         |         |         |         |         |         |
SEQ ID NO:22  EFKSLEPPR---ELKKGYK-MTLDKF
SEQ ID NO:23  EFREIEPPR---ELRSN-RGVTLDNF
SEQ ID NO:24  EFREIEPPR---ELRSN-RGVTLDNF
SEQ ID NO:25  EFREIEPPR---ELKSN-RGVTLDNF
SEQ ID NO:26  EFKSLKPPQ---ELKKDHK-ITLDKF
SEQ ID NO:27  EFREIEPPR---ELKSN-RGVTLDNF
SEQ ID NO:28  EFKALEPPK---ELKSA-KSVTLDFF
SEQ ID NO:29  EFKELEPPM---EFDGD-KNLTLDFF
SEQ ID NO:30  EFKALEPPK---ELKSA-KSVTLDFF
SEQ ID NO:31  EFRKVKPPKGERKKG--KQKTLDSF
SEQ ID NO:32  EFKALEPPR---ELNNE-KVVTLENF
SEQ ID NO:33  EFRKLEPPKKGNEKRS-KQKTLDFF
SEQ ID NO:34  EFKELHPPM--ELGGG-KNLTLDFF
SEQ ID NO:35  EYKSLEPPR---EFGND-KNLTLDFF
SEQ ID NO:36  EFKALEAPR---ELKNN-KIVTLESF
SEQ ID NO:37  EFRKLEPFKKGNEKRS-KQKTLDFF
SEQ ID NO:38  EFISMNPPL--DLLKQ-KASTLDSF
SEQ ID NO:39  EFKELHPPK---KLKKE-DIIKLDFF
SEQ ID NO:40  EFKELHPPK---KLKKE-DIIKLDFF
SEQ ID NO:41  EFIPLNPPKDLLTK----KASTLDSF
SEQ ID NO:42  EFRKPLDPPR--EFGAD-KNLTLDFF
SEQ ID NO:43  EYISLDPPKELKTKT---TTTLDYF
SEQ ID NO:44  EHISLSPPKELKVKSS---TTLDYF
SEQ ID NO:45  EFKKLNPPKREKARKG-KQKTLDML
SEQ ID NO:46  EFKALEPPR---ELGTD-KVVTLENF
SEQ ID NO:47  EFRKLEPPKRESRKKS-KQKTLDFF
SEQ ID NO:48  EFRKLEPPKRDRKSRGKQLKLF---
SEQ ID NO:49  EFRKLEPPKRDRKSRGKQLKLF---
SEQ ID NO:50  EFRKLEPPKRGRKSRGKQLKLF---
SEQ ID NO:51  EFRKLEPPKRDGKSRGKQLRLF---
SEQ ID NO:52  EFRKLEPPKRGRKSKGPQLKLF---
SEQ ID NO:53  EFRELKPFKKERLKEN-KQTTLDFY
```

FIG. 7 (continued)

```
           241              250              260              270              280              290              300
SEQ ID NO:54    EFKKLNPPKREKRKKG--KQKTLD----
SEQ ID NO:55    EFKKLNPPKREKRKKG--KQKTLD----
SEQ ID NO:56    EFKELEPPR--ELGTD-KVVTLEKF
SEQ ID NO:57    EFRRMEPPKRKEKRKS--RQKTLD----
SEQ ID NO:58    EFRKLTPPKRGKSKRGRQKTL-----
SEQ ID NO:59    EFRKLTPPKRGKSKRGRQKTL-----
SEQ ID NO:60    EFRRKLEPPKNNDNKREVKQKTLDFF
SEQ ID NO:61    EFRRVQPPKREKFGRGRQKTL-----
SEQ ID NO:62    EFKKLEPPKRESRKKS-KQRTLDFF
SEQ ID NO:63    EFKRLEPPKRKDKKSRGKQKTLDFF
SEQ ID NO:64    EFKRLEPPKRKDKKSRGKQKTLDFF
SEQ ID NO:65    EFRRVQPPKRESVTKGRQTTL-----
SEQ ID NO:66    EFKALEPPR--ELGTD-KVVTLENF
SEQ ID NO:67    EFKKLTPPKKEKSKK----------
SEQ ID NO:68    EFKKLTPPKKEKSKK----------
SEQ ID NO:69    EFKRLTPPKKEKSRK----------
SEQ ID NO:70    EFRKLQPPKGGKKSRGKQLRLF---
SEQ ID NO:71    EFRKLEPPKRDSK------------
SEQ ID NO:72    EFRKLEPPKRDSK------------
SEQ ID NO:73    EFKKLNPPKREKRKKG--KQKTLD-
SEQ ID NO:74    EFKRLNPPKGSKRDLK---------
SEQ ID NO:75    EFKRLNPPKGSKRDLK---------
SEQ ID NO:76    EFKKLTPPKK---------------
SEQ ID NO:77    EFKKLNPP-----------------
SEQ ID NO:78    EFKKLNPP-----------------
SEQ ID NO:79    EFVSLAPPEE---------------
SEQ ID NO:80    EFVSLAPPEE---------------
SEQ ID NO:81    EFVSLEPP-----------------
SEQ ID NO:82    EFRKLEPP-----------------
SEQ ID NO:83    EFRKLEPP-----------------
SEQ ID NO:84    EFRKLEPP-----------------
SEQ ID NO:85    EFRKLEPP-----------------
```

FIG. 7 (continued)

```
              241       250       260       270       280       290       300
               |         |         |         |         |         |         |
SEQ ID NO:86   EFVSLEP-------------------------------
SEQ ID NO:87   EFKKLNPPKREKRKKG-KQKTLD--------------
SEQ ID NO:88   EF--------------------KQKTLD---------
SEQ ID NO:89   EFRKVEPPKKEKLGRGRQKTL----------------
SEQ ID NO:90   EFKKLNPPKREKARKG-KQKTLDML------------
SEQ ID NO:91   EFTPLNPPKDLLTK----KASTLDSF-----------
SEQ ID NO:92   EFKKLNPPKGSKRDLKQNMKS----------------
SEQ ID NO:93   EFRKLTPPKRGKSKRGRQKTL----------------
SEQ ID NO:94   EFKKLTPPKKEKSRK----------------------
SEQ ID NO:95   EFRRVQPPKRESVAKGRQTTL----------------
SEQ ID NO:96   EFRRLTPPKRGKSKRGRQKTL----------------
SEQ ID NO:97   EFRRVQPPKREKFGRGRQKTL----------------
SEQ ID NO:98   EFRRLTPPKRGKSKRGRQKTL----------------
SEQ ID NO:99   EFRRVQPPKRESVTKGRQTTL----------------
SEQ ID NO:100  EFRKVQPPKRREKLGK---------------------
SEQ ID NO:101  EFKKLKPPKQEKSRK----------------------
SEQ ID NO:102  EFRKVQPPKREKLGK----------------------
SEQ ID NO:103  EFRKLEPPKRDSK------------------------
SEQ ID NO:104  EFRKLEPP-----------------------------
```

FIG. 7 (continued)

SEQUENCE LISTING

<160> NUMBER OF SEQ ID NOS: 109

<210> SEQ ID NO 1
<211> LENGTH: 260
<212> TYPE: PRT
<213> ORGANISM: Methanobrevibacter

<400> SEQUENCE: 1

```
Met Lys Tyr Lys Ile Leu Glu Asn Pro Asn Cys Glu Asp Ala Tyr Gly
1               5                   10                  15

Leu Ile Glu Glu Ala Leu Arg Lys Arg Ala Thr Ile Thr Ile Tyr Ala
            20                  25                  30

Cys Cys Lys Val Asn Tyr Glu Gly Arg Ala Leu Ser Glu Leu Asn Trp
        35                  40                  45

Gly Glu Arg Ile Ile Leu Ile Lys Pro Asp Gly Ser Phe Leu Ile His
    50                  55                  60

Gln Glu Lys Lys Val Glu Pro Val Asn Trp Gln Pro Pro Lys Ser Lys
65                  70                  75                  80

Thr Arg Gly Tyr Ile Gln Asp Asn Asn Leu Ile Leu Glu Ser His Arg
                85                  90                  95

Arg Thr Pro Lys Glu Leu Leu Thr Val Glu Ile Arg Lys Val Gln Tyr
            100                 105                 110

Ile Thr Tyr Ala Asn Ile Glu Asp Phe Glu Glu Leu Glu Gln Ala Gly
        115                 120                 125

Tyr Glu Lys Asp Met Gly Asp Met Ile Met Glu Lys Pro His Met Ile
    130                 135                 140

Glu Glu Gly Phe Lys Pro Thr Ala Arg Glu Tyr Ser Val Glu His Gly
145                 150                 155                 160

Phe Ile Asp Ile Leu Gly Lys Asp Cys Asp Asn Asn Leu Met Ile Leu
                165                 170                 175

Glu Leu Lys Ala Arg Lys Ala Gly Val Ser Ala Val Lys Gln Leu Lys
            180                 185                 190

Arg Tyr Leu Thr Asp Phe Glu Asp Asp Asn Asp Tyr Leu Lys Glu
        195                 200                 205

Cys Leu Val Gln Lys Lys Ile Arg Gly Leu Leu Val Ala Pro Ser
    210                 215                 220

Leu Gly Glu Asp Ala Lys Glu Leu Ile Glu Lys Glu Gly Ile Glu Phe
225                 230                 235                 240

Val Ala Val Asn Pro Pro Lys Glu Leu Lys Arg Asp Lys Lys Val Thr
                245                 250                 255

Leu Asp Ala Phe
            260
```

```
<210> SEQ ID NO 2
<211> LENGTH: 260
<212> TYPE: PRT
<213> ORGANISM: Methanobrevibacter smithii

<400> SEQUENCE: 2

Met Lys Tyr Lys Ile Leu Glu Asn Pro Asn Cys Glu Asp Ala Tyr Gly
1               5                   10                  15

Leu Ile Glu Glu Ala Leu Arg Lys Arg Ala Thr Ile Thr Ile Tyr Ala
                20                  25                  30

Cys Cys Lys Val Asn Tyr Glu Gly Arg Ala Leu Ser Glu Leu Asn Trp
            35                  40                  45

Gly Glu Arg Ile Ile Leu Ile Lys Pro Asp Gly Ser Phe Leu Ile His
        50                  55                  60

Gln Glu Lys Lys Val Glu Pro Val Asn Trp Gln Pro Pro Lys Ser Lys
65                  70                  75                  80

Thr Arg Gly Tyr Ile Gln Asp Asn Asn Leu Ile Leu Glu Ser His Arg
                85                  90                  95

Arg Thr Pro Lys Glu Leu Leu Thr Val Glu Ile Arg Lys Val Gln Tyr
            100                 105                 110

Ile Thr Tyr Ala Asn Ile Glu Asp Phe Glu Glu Leu Glu Gln Ala Gly
        115                 120                 125

Tyr Glu Lys Asp Met Gly Asp Met Ile Met Glu Lys Pro His Met Ile
130                 135                 140

Glu Gly Phe Lys Pro Thr Ala Arg Glu Tyr Ser Val Glu His Gly
145                 150                 155                 160

Phe Ile Asp Ile Leu Gly Lys Asp Cys Asp Asn Asn Leu Met Ile Leu
                165                 170                 175

Glu Leu Lys Ala Arg Lys Ala Gly Val Ser Ala Val Lys Gln Leu Lys
            180                 185                 190

Arg Tyr Leu Thr Asp Phe Glu Asp Gly Asp Asn Asp Tyr Leu Lys Glu
        195                 200                 205

Cys Leu Val Gln Lys Lys Ile Arg Gly Leu Leu Val Ala Pro Ser
210                 215                 220

Leu Gly Glu Asp Ala Lys Glu Leu Ile Glu Lys Glu Gly Ile Glu Phe
225                 230                 235                 240

Val Ala Val Asn Pro Pro Lys Glu Leu Lys Arg Asp Lys Lys Val Thr
                245                 250                 255

Leu Asp Ala Phe
            260

<210> SEQ ID NO 3
<211> LENGTH: 260
<212> TYPE: PRT
<213> ORGANISM: Methanobrevibacter smithii

<400> SEQUENCE: 3

Met Lys Tyr Lys Ile Leu Glu Asn Pro Asn Cys Glu Asp Ala Tyr Gly
1               5                   10                  15

Leu Val Glu Glu Ala Leu Arg Lys Lys Ala Thr Ile Thr Ile Tyr Ala
                20                  25                  30

Cys Cys Lys Val Thr Tyr Glu Gly Arg Ala Leu Ser Glu Leu Asn Trp
            35                  40                  45

Gly Glu Arg Ile Ile Leu Ile Lys Pro Asp Gly Ser Phe Leu Ile His
        50                  55                  60

Gln Glu Lys Lys Val Glu Pro Val Asn Trp Gln Pro Pro Lys Ser Lys
```

```
                65                  70                  75                  80
Thr Arg Gly Tyr Ile Gln Asp Asp Asn Leu Ile Leu Glu Ser His Arg
                    85                  90                  95

Arg Thr Pro Lys Glu Leu Leu Ile Val Glu Ile Arg Lys Val Gln Tyr
                100                 105                 110

Ile Thr Tyr Ala Asn Ile Glu Asp Phe Glu Glu Leu Glu Gln Ala Gly
                115                 120                 125

Tyr Glu Lys Asp Met Gly Asp Met Ile Met Lys Pro His Met Ile
130                 135                 140

Glu Glu Gly Phe Lys Pro Thr Ala Arg Glu Tyr Ser Val Glu His Gly
145                 150                 155                 160

Phe Ile Asp Ile Leu Gly Lys Asp Arg Asp Asn Asn Leu Met Ile Leu
                165                 170                 175

Glu Leu Lys Ala Arg Lys Ala Gly Val Ser Ala Val Lys Gln Leu Lys
                180                 185                 190

Arg Tyr Leu Thr Asp Phe Glu Asp Asp Asn Asp Tyr Leu Lys Glu
                195                 200                 205

Cys Arg Val Gln Lys Lys Ile Arg Gly Leu Leu Val Ala Pro Ser
    210                 215                 220

Leu Gly Asn Asp Ala Glu Glu Leu Leu Glu Lys Gly Ile Glu Phe
225                 230                 235                 240

Val Ala Val Glu Pro Pro Lys Glu Leu Lys Arg Asp Lys Lys Val Thr
                245                 250                 255

Leu Asp Ala Phe
            260

<210> SEQ ID NO 4
<211> LENGTH: 260
<212> TYPE: PRT
<213> ORGANISM: Methanobrevibacter smithii

<400> SEQUENCE: 4

Met Lys Tyr Lys Ile Leu Glu Asn Pro Asn Cys Glu Asp Ala Tyr Gly
1               5                   10                  15

Leu Val Glu Glu Ala Leu Arg Lys Lys Ala Thr Ile Thr Ile Tyr Ala
                20                  25                  30

Cys Cys Lys Val Thr Tyr Glu Gly Arg Ala Leu Ser Glu Leu Asn Trp
            35                  40                  45

Gly Glu Arg Ile Ile Leu Ile Lys Pro Asp Gly Ser Phe Leu Ile His
        50                  55                  60

Gln Glu Lys Lys Val Glu Pro Val Asn Trp Gln Pro Pro Lys Ser Lys
65                  70                  75                  80

Thr Arg Gly Tyr Ile Gln Asp Asp Asn Leu Ile Leu Glu Ser His Arg
                    85                  90                  95

Arg Thr Pro Lys Glu Leu Leu Ile Val Glu Ile Arg Lys Val Gln Tyr
                100                 105                 110

Ile Thr Tyr Ala Asn Ile Glu Asp Phe Glu Glu Leu Glu Gln Ala Gly
                115                 120                 125

Tyr Glu Lys Asp Met Gly Asp Met Ile Met Lys Lys Pro His Met Ile
130                 135                 140

Glu Glu Gly Phe Lys Pro Thr Ala Arg Glu Tyr Ser Val Glu His Gly
145                 150                 155                 160

Phe Ile Asp Ile Leu Gly Lys Asp Arg Asp Asn Asn Leu Met Ile Leu
                165                 170                 175
```

```
Glu Leu Lys Ala Arg Lys Ala Gly Val Ser Ala Val Lys Gln Leu Lys
            180                 185                 190

Arg Tyr Leu Thr Asp Phe Glu Asp Asp Asn Asp Tyr Leu Lys Glu
            195                 200                 205

Cys Arg Val Gln Lys Lys Ile Arg Gly Leu Leu Val Ala Pro Ser
            210                 215                 220

Leu Gly Asn Asp Ala Glu Glu Leu Leu Glu Lys Glu Gly Ile Glu Phe
225                 230                 235                 240

Val Ala Val Glu Pro Pro Lys Glu Leu Lys Arg Asp Lys Lys Val Thr
            245                 250                 255

Leu Asp Ala Phe
            260

<210> SEQ ID NO 5
<211> LENGTH: 260
<212> TYPE: PRT
<213> ORGANISM: Methanobrevibacter smithii

<400> SEQUENCE: 5

Met Lys Tyr Lys Ile Leu Glu Asn Pro Asn Cys Glu Asp Ala Tyr Gly
1               5                   10                  15

Leu Val Glu Glu Ala Leu Arg Lys Lys Ala Thr Ile Thr Ile Tyr Ala
            20                  25                  30

Cys Cys Lys Val Thr Tyr Glu Gly Arg Ala Leu Ser Glu Leu Asn Trp
        35                  40                  45

Gly Glu Arg Ile Ile Leu Ile Lys Pro Asp Gly Ser Phe Leu Ile His
    50                  55                  60

Gln Glu Lys Lys Val Glu Pro Val Asn Trp Gln Pro Pro Lys Ser Lys
65                  70                  75                  80

Thr Arg Gly Tyr Ile Gln Asp Asp Asn Leu Ile Leu Glu Ser His Arg
                85                  90                  95

Arg Thr Pro Lys Glu Leu Leu Ile Val Glu Ile Arg Lys Val Gln Tyr
            100                 105                 110

Ile Thr Tyr Ala Asn Ile Glu Asp Phe Glu Glu Leu Glu Gln Ala Gly
        115                 120                 125

Tyr Glu Lys Asp Met Gly Asp Met Ile Met Glu Lys Pro His Met Ile
    130                 135                 140

Glu Glu Gly Phe Lys Pro Thr Ala Arg Glu Tyr Ser Val Glu His Gly
145                 150                 155                 160

Phe Ile Asp Ile Leu Gly Lys Asp Arg Asn Asn Asn Leu Met Ile Leu
                165                 170                 175

Glu Leu Lys Ala Arg Lys Ala Gly Val Ser Ala Val Lys Gln Leu Lys
            180                 185                 190

Arg Tyr Leu Thr Asp Phe Glu Asp Asp Asn Asp Tyr Leu Lys Glu
            195                 200                 205

Cys Arg Val Gln Lys Lys Ile Arg Gly Leu Leu Val Ala Pro Ser
            210                 215                 220

Leu Gly Asn Asp Ala Glu Glu Leu Leu Glu Lys Glu Gly Ile Glu Phe
225                 230                 235                 240

Val Ala Val Glu Pro Pro Lys Glu Leu Lys Arg Asp Lys Lys Val Thr
            245                 250                 255

Leu Asp Ala Phe
            260

<210> SEQ ID NO 6
```

```
<211> LENGTH: 260
<212> TYPE: PRT
<213> ORGANISM: Methanobrevibacter oralis

<400> SEQUENCE: 6

Met Lys Tyr Arg Ile Leu Glu Arg Pro Ser Cys Glu Glu Gly Tyr Asp
1               5                   10                  15

Leu Val Glu Glu Ala Leu Arg Lys Lys Ala Thr Ile Ile Ile Phe Ala
            20                  25                  30

Cys Cys Lys Val Asn Tyr Glu Gly Arg Ala Leu Ser Gln Leu Asn Trp
        35                  40                  45

Gly Glu Arg Ile Ile Leu Ile Lys Pro Asp Gly Ser Phe Leu Ile His
    50                  55                  60

Gln Glu Arg Lys Val Asp Pro Val Asn Trp Gln Pro Pro Lys Ser Arg
65                  70                  75                  80

Thr Arg Ser Phe Ile Arg Asn Asp Lys Leu Ile Leu Glu Ser His Arg
                85                  90                  95

Arg Val Pro Lys Glu Leu Leu Ser Val Glu Ile Arg Lys Ile Gln Phe
            100                 105                 110

Ile Asn Tyr Ala Asn Val Glu Asp Phe Glu Glu Leu Glu Gln Ala Gly
        115                 120                 125

Tyr Glu Lys Asp Met Gly Asp Met Ile Met Asp Lys Pro His Leu Ile
    130                 135                 140

Glu Glu Gly Phe Thr Pro Thr Ala Arg Glu Tyr Ser Val Glu His Gly
145                 150                 155                 160

Phe Ile Asp Ile Leu Gly Lys Asp Asp Asp Asn Asn Leu Met Val Leu
                165                 170                 175

Glu Leu Lys Ala Arg Lys Ala Gly Val Ser Ala Val Lys Gln Leu Lys
            180                 185                 190

Arg Tyr Leu Ser Asp Phe Glu Asn Thr Glu Asn Asp Tyr Leu Lys Glu
        195                 200                 205

Cys Lys Ala Ser Lys Lys Arg Ile Arg Gly Leu Leu Val Ala Pro Ser
    210                 215                 220

Leu Gly Glu Asp Ala Lys Glu Met Ile Glu Asp Glu Gly Ile Glu Phe
225                 230                 235                 240

Val Ser Ile Glu Pro Pro Lys Glu Leu Arg Arg Asp Lys Lys Thr Thr
                245                 250                 255

Leu Asp Ala Phe
            260

<210> SEQ ID NO 7
<211> LENGTH: 260
<212> TYPE: PRT
<213> ORGANISM: Methanobrevibacter gottschalkii

<400> SEQUENCE: 7

Met Lys Tyr Lys Ile Leu Glu Lys Pro Ser Cys Glu Asp Gly Tyr Asp
1               5                   10                  15

Leu Val Gln Glu Ala Leu Arg Lys Lys Ala Thr Ile Leu Ile Phe Ala
            20                  25                  30

Cys Cys Lys Val Ser Tyr Glu Gly Arg Ala Leu Ser Glu Leu Asn Trp
        35                  40                  45

Gly Glu Arg Ile Ile Met Ile Lys Pro Asp Gly Thr Phe Leu Ile His
    50                  55                  60

Gln Glu Lys Lys Val Glu Pro Val Asn Trp Gln Pro Pro Lys Ser Arg
65                  70                  75                  80
```

```
Thr Arg Ser Tyr Ile Lys Asn Asp Asn Leu Phe Leu Glu Ser His Arg
                 85                  90                  95

Arg Thr Pro Lys Glu Leu Leu Thr Val Glu Ile Arg Lys Ile Gln Phe
            100                 105                 110

Ile Asn Tyr Ala Asn Ile Glu Asp Phe Glu Glu Leu Glu Gln Ala Gly
            115                 120                 125

Tyr Glu Lys Asp Met Gly Asp Met Ile Met Glu Lys Pro His Met Ile
            130                 135                 140

Glu Glu Gly Phe Thr Pro Thr Ala Arg Glu Tyr Ser Val Glu His Gly
145                 150                 155                 160

Phe Ile Asp Ile Leu Gly Lys Asp Arg Asp Asn Asn Leu Met Val Leu
                165                 170                 175

Glu Leu Lys Ala Arg Lys Ala Gly Ile Thr Ala Val Lys Gln Leu Arg
            180                 185                 190

Arg Tyr Leu Gln Asp Leu Glu Asn Thr Asp Asn Asp Tyr Leu Lys Glu
            195                 200                 205

Cys Glu Ser Gln Lys Lys Ile Arg Gly Leu Leu Val Ala Pro Ser
            210                 215                 220

Ile Met Asp Asp Ala Leu Glu Leu Leu Glu Asn Glu Gly Ile Glu Phe
225                 230                 235                 240

Val Ser Ile Glu Pro Pro Arg Glu Leu Lys Arg Asp Lys Lys Val Thr
                245                 250                 255

Leu Asp Ala Phe
            260

<210> SEQ ID NO 8
<211> LENGTH: 260
<212> TYPE: PRT
<213> ORGANISM: Methanobrevibacter

<400> SEQUENCE: 8

Met Lys Tyr Lys Ile Leu Glu Lys Pro Ser Cys Glu Asp Gly Tyr Asp
1               5                   10                  15

Leu Val Gln Glu Ala Leu Arg Lys Lys Thr Thr Ile Leu Ile Phe Ala
            20                  25                  30

Cys Cys Lys Val Ser Tyr Glu Gly Arg Ala Leu Ser Glu Leu Asn Trp
            35                  40                  45

Gly Glu Arg Ile Ile Met Ile Lys Pro Asp Gly Thr Phe Leu Ile His
        50                  55                  60

Gln Glu Lys Lys Val Glu Pro Val Asn Trp Gln Pro Pro Lys Ser Arg
65                  70                  75                  80

Thr Arg Ser Tyr Ile Lys Asn Asp Asn Leu Phe Leu Glu Ser His Arg
                85                  90                  95

Arg Thr Pro Lys Glu Leu Leu Thr Val Glu Ile Arg Lys Ile Gln Phe
            100                 105                 110

Ile Asn Tyr Ala Asn Ile Glu Asp Phe Glu Glu Leu Glu Gln Ala Gly
            115                 120                 125

Tyr Glu Lys Asp Met Gly Asp Met Ile Met Glu Lys Pro His Met Ile
            130                 135                 140

Glu Glu Gly Phe Thr Pro Thr Ala Arg Glu Tyr Ser Val Glu His Gly
145                 150                 155                 160

Phe Ile Asp Ile Leu Gly Lys Asp Ser Asp Asn Asn Leu Met Val Leu
                165                 170                 175

Glu Leu Lys Ala Arg Lys Ala Gly Ile Thr Ala Val Lys Gln Leu Arg
```

```
            180                 185                 190
Arg Tyr Leu Gln Asp Leu Glu Asn Thr Asp Asn Asp Tyr Leu Lys Glu
            195                 200                 205

Cys Glu Ser Gln Lys Lys Lys Ile Arg Gly Leu Leu Val Ala Pro Ser
        210                 215                 220

Ile Met Asp Asp Ala Leu Glu Leu Leu Glu Asn Glu Gly Ile Glu Phe
225                 230                 235                 240

Val Ser Ile Glu Pro Pro Arg Glu Leu Lys Arg Asp Lys Lys Val Thr
                245                 250                 255

Leu Asp Ala Phe
            260

<210> SEQ ID NO 9
<211> LENGTH: 260
<212> TYPE: PRT
<213> ORGANISM: Methanobrevibacter millerae

<400> SEQUENCE: 9

Met Lys Tyr Lys Ile Leu Glu Lys Pro Asp Cys Glu Lys Ala Tyr Glu
1               5                   10                  15

Leu Val Glu Glu Ala Met Arg Lys Arg Ala Thr Ile Thr Leu Phe Ala
            20                  25                  30

Cys Cys Lys Val Glu Tyr Glu Gly Arg Ala Leu Ser Gln Leu Asn Trp
        35                  40                  45

Gly Glu Arg Ile Ile Leu Ile Lys Pro Asp Gly Ser Phe Leu Ile His
    50                  55                  60

Gln Asp Lys Lys Val Glu Pro Val Asn Trp Gln Pro Lys Ser Lys
65                  70                  75                  80

Thr Arg Ser Tyr Leu Ser Gly Glu Arg Leu Ile Leu Glu Ser His Arg
                85                  90                  95

Arg Thr Pro Lys Glu Leu Leu Thr Val Glu Val Arg Gln Ile Gln Phe
            100                 105                 110

Ile Ser Tyr Ala Asn Met Glu Asp Phe Glu Glu Leu Glu Gln Ala Gly
        115                 120                 125

Tyr Glu Lys Asp Met Ser Asp Met Ile Met Glu Arg Pro His Leu Ile
    130                 135                 140

Glu Glu Gly Phe Thr Pro Lys Thr Arg Glu Tyr Ser Val Glu His Gly
145                 150                 155                 160

Phe Ile Asp Ile Leu Gly Lys Asp Asn Asp Gly Asn Leu Met Val Leu
                165                 170                 175

Glu Leu Lys Ala Arg Lys Ala Gly Val Ser Ala Val Lys Gln Ile Arg
            180                 185                 190

Arg Tyr Leu Gln Asp Leu Glu Asn Thr Glu Asn Asp Tyr Leu Lys Glu
        195                 200                 205

Cys Lys Ala Gln Lys Lys Lys Ile Arg Gly Ile Leu Val Ala Pro Ser
    210                 215                 220

Ile Met Glu Asp Ala Arg Glu Met Ile Glu Glu Gly Ile Glu Phe
225                 230                 235                 240

Val Ser Val Glu Pro Pro Arg Glu Leu Lys Arg Asp Lys Lys Val Thr
                245                 250                 255

Leu Asp Ala Phe
            260

<210> SEQ ID NO 10
<211> LENGTH: 260
```

```
<212> TYPE: PRT
<213> ORGANISM: Methanobrevibacter

<400> SEQUENCE: 10

Met Lys Tyr Lys Ile Leu Glu Lys Pro Asn Cys Glu Asp Ala Tyr Glu
1               5                   10                  15

Leu Val Gln Asp Ala Leu Arg Lys Lys Ala Thr Ile Ile Ile Phe Ala
            20                  25                  30

Cys Cys Lys Val Asn Tyr Glu Gly Arg Ala Leu Ser Glu Leu Asn Trp
        35                  40                  45

Gly Glu Arg Ile Ile Met Ile Lys Pro Asp Gly Ala Phe Leu Ile His
    50                  55                  60

Gln Glu Lys Lys Val Glu Pro Val Asn Trp Gln Pro Pro Lys Ser Arg
65                  70                  75                  80

Thr Arg Ser Tyr Ile Lys Asn Glu Asn Leu Phe Leu Glu Ser His Arg
                85                  90                  95

Arg Thr Pro Lys Glu Leu Leu Thr Ala Glu Ile Arg Gln Ile Gln Phe
            100                 105                 110

Ile Ser Tyr Ala Asn Ile Glu Asp Phe Glu Glu Leu Glu Gln Ala Gly
        115                 120                 125

Tyr Glu Lys Asp Met Ser Asp Met Ile Met Glu Lys Pro His Leu Ile
    130                 135                 140

Glu Glu Gly Phe Thr Pro Thr Thr Arg Glu Tyr Ser Val Glu His Gly
145                 150                 155                 160

Phe Ile Asp Ile Leu Gly Lys Asp Ser Asp Asn Asn Leu Met Val Leu
                165                 170                 175

Glu Leu Lys Ala Arg Lys Ala Gly Val Ala Ala Val Lys Gln Leu Arg
            180                 185                 190

Arg Tyr Leu Gln Asp Leu Glu Asn Thr Asp Asn Asp Tyr Leu Lys Glu
        195                 200                 205

Cys Lys Ala Gln Lys Lys Ile Arg Gly Leu Leu Val Ala Pro Ser
    210                 215                 220

Ile Met Asp Asp Ala Leu Glu Leu Ile Glu Glu Gly Ile Glu Phe
225                 230                 235                 240

Val Ser Ile Glu Pro Pro Arg Glu Leu Lys Arg Asp Lys Lys Val Thr
                245                 250                 255

Leu Asp Ala Phe
            260

<210> SEQ ID NO 11
<211> LENGTH: 254
<212> TYPE: PRT
<213> ORGANISM: Methanobrevibacter oralis

<400> SEQUENCE: 11

Met Lys Tyr Arg Ile Leu Glu Arg Pro Ser Cys Glu Glu Gly Tyr Asp
1               5                   10                  15

Leu Val Glu Glu Ala Leu Arg Lys Lys Ala Thr Ile Ile Ile Phe Ala
            20                  25                  30

Cys Cys Lys Val Asn Tyr Glu Gly Arg Ala Leu Ser Gln Leu Asn Trp
        35                  40                  45

Gly Glu Arg Ile Ile Leu Ile Lys Pro Asp Gly Ser Phe Leu Ile His
    50                  55                  60

Gln Glu Arg Lys Val Asp Pro Val Asn Trp Gln Pro Pro Lys Ser Arg
65                  70                  75                  80
```

```
Thr Arg Ser Phe Ile Arg Asn Asp Lys Leu Ile Leu Glu Ser His Arg
                85                  90                  95

Arg Val Pro Lys Glu Leu Leu Ser Val Glu Ile Arg Lys Ile Gln Phe
            100                 105                 110

Ile Asn Tyr Ala Asn Val Glu Asp Phe Glu Glu Leu Glu Gln Ala Gly
        115                 120                 125

Tyr Glu Lys Asp Met Gly Asp Met Ile Met Asp Lys Pro His Leu Ile
    130                 135                 140

Glu Glu Gly Phe Thr Pro Thr Ala Arg Glu Tyr Ser Val Glu His Gly
145                 150                 155                 160

Phe Ile Asp Ile Leu Gly Lys Asp Asp Asn Asn Leu Met Val Leu
                165                 170                 175

Glu Leu Lys Ala Arg Lys Ala Gly Val Ser Ala Val Lys Gln Leu Lys
            180                 185                 190

Arg Tyr Leu Ser Asp Phe Glu Asn Thr Glu Asn Asp Tyr Leu Lys Glu
        195                 200                 205

Cys Lys Ala Ser Lys Arg Ile Arg Gly Leu Leu Val Ala Pro Ser
    210                 215                 220

Leu Gly Glu Asp Ala Lys Glu Met Ile Glu Asp Glu Gly Ile Glu Phe
225                 230                 235                 240

Val Ser Ile Glu Pro Pro Lys Glu Leu Arg Arg Asp Lys Lys
                245                 250

<210> SEQ ID NO 12
<211> LENGTH: 260
<212> TYPE: PRT
<213> ORGANISM: Methanobrevibacter cuticularis

<400> SEQUENCE: 12

Met Lys Tyr Lys Leu Leu Glu Asn Pro Asn Ile Glu Glu Met Tyr Asp
1               5                   10                  15

Leu Ile Glu Glu Gly Leu Arg Lys Lys Ala Met Ile Asn Val Phe Cys
            20                  25                  30

Cys Cys Lys Val Ile Tyr Glu Gly Arg Ala Leu Ser Gln Leu Asp Phe
        35                  40                  45

Gly Glu Arg Met Ile Leu Leu Lys Pro Asp Gly Ser Phe Leu Ile His
    50                  55                  60

Gln Glu Arg Lys Val Asp Pro Val Asn Trp Gln Pro Pro Lys Ser Arg
65                  70                  75                  80

Thr Arg Thr Phe Ile Lys Asp Asn Thr Leu Phe Leu Glu Ser His Arg
                85                  90                  95

Arg Ser Pro Lys Glu Arg Leu Glu Val Glu Ile Lys Lys Thr His Phe
            100                 105                 110

Val Asn Tyr Val Leu Val Glu Asp Tyr Gln Glu Leu Glu Ile Ala Gly
        115                 120                 125

Tyr Glu Lys Asp Met Gly Asp Met Ile Met Lys His Pro His Met Ile
    130                 135                 140

Glu Glu Gly Phe Lys Pro Thr Asp Arg Glu Tyr Ser Thr Glu His Gly
145                 150                 155                 160

Phe Ile Asp Ile Leu Gly Lys Asp Lys Glu Gly Asn Leu Met Val Leu
                165                 170                 175

Glu Leu Lys Cys Arg Lys Ala Gly Ile Asn Ala Val Lys Gln Ile Arg
            180                 185                 190

Arg Tyr Leu Thr Asp Phe Lys Glu Glu Asn Ser Asn Leu Glu Asn
        195                 200                 205
```

```
Thr Gly Asn Glu Lys Lys Val Arg Gly Leu Leu Val Ala Pro Ser
    210                 215                 220

Ile Gly Glu Asp Ala Arg Glu Leu Leu Glu Glu Asn Ile Glu Phe
225                 230                 235                 240

Lys Ser Ile Asp Pro Pro Lys Glu Leu Lys Asn Asp Lys Lys Val Thr
                    245                 250                 255

Leu Asp Ile Phe
            260

<210> SEQ ID NO 13
<211> LENGTH: 260
<212> TYPE: PRT
<213> ORGANISM: Methanobrevibacter curvatus

<400> SEQUENCE: 13

Met Lys Phe Lys Gly Lys Glu Asp Pro Asn Ile Asp Glu Ser Phe Asp
1               5                   10                  15

Leu Ile Asp Glu Gly Leu Arg Lys Lys Ala Thr Ile Val Ile Phe Ala
                20                  25                  30

Cys Cys Lys Val Ile Tyr Glu Gly Arg Ala Ile Ser Gln Leu Asp Phe
            35                  40                  45

Gly Glu Arg Ile Ile Leu Ile Lys Pro Asp Gly Ser Phe Leu Ile His
        50                  55                  60

Gln Asp Lys Lys Val Asp Pro Val Asn Trp Gln Pro Pro Lys Ser Arg
65                  70                  75                  80

Ser Arg Val Leu Ile Arg Asn Glu Lys Leu Phe Leu Glu Ser Phe Arg
                85                  90                  95

Arg Thr Pro Arg Glu His Leu Glu Val Glu Ile Arg Lys Ile His Phe
                100                 105                 110

Leu Asn Tyr Ala Leu Ile Glu Asp Tyr Gln Glu Leu Glu Ile Ala Gly
            115                 120                 125

Tyr Glu Lys Asp Leu Gly Asp Leu Ile Ile Asp Lys Pro His Leu Ile
        130                 135                 140

Glu Glu Gly Phe Lys Pro Thr Asn Arg Glu Tyr Ser Thr Glu His Gly
145                 150                 155                 160

Phe Ile Asp Ile Leu Gly Asn Asp Lys Glu Gly Asn Leu Met Val Leu
                165                 170                 175

Glu Leu Lys Ser Arg Lys Ile Gly Val Asn Ala Val Lys Gln Ile Arg
            180                 185                 190

Arg Tyr Leu Ser Asp Phe Glu Asp Glu Lys Asn Ser Tyr Leu Lys Asp
        195                 200                 205

Leu Gly Val Glu Lys Lys Lys Ile Arg Gly Leu Leu Val Ala Pro Lys
    210                 215                 220

Ile Asp Glu Asp Ala Lys Glu Met Ile Glu Glu Gly Ile Glu Phe
225                 230                 235                 240

Val Ser Leu Glu Pro Pro Lys Glu Leu Lys Arg Asp Lys Leu Val Thr
                    245                 250                 255

Leu Asp Ser Phe
            260

<210> SEQ ID NO 14
<211> LENGTH: 260
<212> TYPE: PRT
<213> ORGANISM: Methanobrevibacter olleyae

<400> SEQUENCE: 14
```

```
Met Lys Tyr Lys Ile Leu Glu Asn Pro Asn Tyr Glu Glu Thr Tyr Asp
1               5                   10                  15

Leu Ile Glu Glu Gly Leu Lys Lys Ala Thr Ile Leu Leu Phe Ala
            20                  25                  30

Cys Cys Arg Val Ser Tyr Glu Gly Arg Ser Leu Ser Glu Leu Asp Tyr
            35                  40                  45

Gly Glu Arg Ile Ile Met Met Lys Pro Asp Gly Cys Phe Leu Ile His
50                  55                  60

Gln Asp Asn Lys Val Asp Pro Val Asn Trp Gln Pro Pro Lys Ser Arg
65                  70                  75                  80

Pro Arg Ala Tyr Ile Lys Asp Glu Ile Leu Phe Leu Glu Ser His Arg
                85                  90                  95

Arg Ser Pro Pro Glu Arg Ile Glu Val Glu Ile Lys Lys Val His Tyr
            100                 105                 110

Ala Asn Tyr Asn Leu Ile Glu Asp Tyr Glu Glu Leu Glu Arg Ala Gly
            115                 120                 125

Tyr Glu Lys Asp Met Gly Asp Met Ile Trp Asp Lys Pro His Ile Ile
130                 135                 140

Glu Glu Gly Phe Arg Pro Thr Val Arg Glu Tyr Ala Thr Glu His Gly
145                 150                 155                 160

Phe Ile Asp Ile Leu Gly Lys Asp Ser Lys Gly Asn Leu Met Val Leu
                165                 170                 175

Glu Leu Lys Ser Arg Lys Ala Gly Ile Thr Ala Val Lys Gln Ile Arg
            180                 185                 190

Arg Tyr Leu Thr Asp Phe Glu Asn Glu Asn Ser Glu Ile Lys Ala
            195                 200                 205

Lys Asn Gly Gln Lys Gln Lys Ile Arg Gly Leu Leu Val Ala Pro Ser
210                 215                 220

Ile Gly Asp Asp Ala Leu Glu Leu Leu Glu Glu Gly Ile Glu Phe
225                 230                 235                 240

Val Ser Val Glu Pro Pro Arg Glu Leu Lys Lys Asp Lys Arg Val Thr
                245                 250                 255

Leu Asp Ser Phe
            260

<210> SEQ ID NO 15
<211> LENGTH: 259
<212> TYPE: PRT
<213> ORGANISM: Methanobrevibacter ruminantium

<400> SEQUENCE: 15

Met Lys Tyr Lys Ile Leu Glu Asn Pro Asn Tyr Lys Glu Ala Tyr Glu
1               5                   10                  15

Leu Ile Glu Glu Gly Leu Val Lys Ala Thr Met Leu Leu Phe Ala
            20                  25                  30

Cys Cys Lys Val Ser Tyr Glu Gly Arg Ala Leu Ser Glu Leu Asp Tyr
            35                  40                  45

Gly Glu Arg Ile Ile Met Ile Lys Pro Asp Gly Cys Phe Leu Ile His
50                  55                  60

Gln Asp Asn Lys Val Asp Pro Val Asn Trp Gln Pro Pro Lys Ser Lys
65                  70                  75                  80

Thr Lys Ala Leu Ile Lys Asp Glu Thr Leu Tyr Leu Glu Ser His Arg
                85                  90                  95

Arg Lys Pro Pro Glu Leu Leu Glu Val Glu Val Lys Lys Ile His Tyr
```

```
                    100                 105                 110
Ala Arg Tyr Asn Leu Ile Glu Asp Tyr Glu Glu Leu Glu Arg Ala Gly
                115                 120                 125

Tyr Glu Lys Asp Met Gly Asp Met Ile Trp Asp Asn Pro His Ile Ile
            130                 135                 140

Glu Glu Gly Phe Arg Pro Thr Val Arg Glu Tyr Ala Thr Glu His Gly
145                 150                 155                 160

Phe Ile Asp Ile Leu Gly Lys Asp Ala Asp Gly Asn Leu Met Val Leu
                165                 170                 175

Glu Leu Lys Ala Arg Lys Ala Gly Ile Thr Ala Val Lys Gln Ile Arg
            180                 185                 190

Arg Tyr Leu Thr Asp Phe Glu Asn Arg Glu Asn Lys Glu Ile Arg His
                195                 200                 205

Glu Glu Glu Lys Gln Lys Val Arg Gly Leu Leu Val Ala Pro Ser Ile
            210                 215                 220

Gly Asp Asp Ala Leu Glu Leu Leu Glu Glu Gly Ile Glu Phe Val
225                 230                 235                 240

Ser Val Glu Pro Pro Arg Glu Leu Lys Lys Asp Lys Lys Val Thr Leu
                245                 250                 255

Asp Ala Phe

<210> SEQ ID NO 16
<211> LENGTH: 259
<212> TYPE: PRT
<213> ORGANISM: Methanobrevibacter

<400> SEQUENCE: 16

Met Asn Tyr Lys Thr Ile Glu Glu Pro Asn Thr Glu Glu Thr Tyr Asp
1               5                   10                  15

Leu Ile Glu Ala Gly Leu Arg Lys Lys Ala Met Ile Thr Leu Phe Thr
            20                  25                  30

Tyr Cys Lys Val Glu Tyr Glu Gly Arg Ala Leu Ser Gln Leu Gly Tyr
        35                  40                  45

Gly Glu Arg Met Ile Leu Ile Lys Pro Asp Gly Ser Phe Leu Val His
50                  55                  60

Gln Asp Arg Lys Val Glu Pro Val Asn Trp Gln Pro Pro Lys Ser Lys
65                  70                  75                  80

Thr Arg Val Phe Ile Arg Asp Gly Lys Val Ile Ile Glu Ser Asn Arg
                85                  90                  95

Arg Thr Pro Lys Glu Arg Leu Glu Val Leu Ile Glu Lys Thr Phe Ile
            100                 105                 110

Gly Thr Tyr Ala Val Val Glu Asp Tyr Glu Glu Leu Glu Gln Ala Gly
                115                 120                 125

Tyr Glu Lys Asp Met Gly Asp Met Ile Met Glu Asn Pro His Ile Ile
            130                 135                 140

Glu Glu Gly Phe Lys Pro Thr Asp Arg Glu Tyr Asn Val Glu His Gly
145                 150                 155                 160

Phe Ile Asp Ile Leu Gly Lys Asp Ser Asp Gly Asn Leu Met Ile Leu
                165                 170                 175

Glu Leu Lys Ser Arg Lys Ile Gly Ile Ser Ala Val Lys Gln Ile Lys
            180                 185                 190

Arg Tyr Ile Asp Asp Leu Thr Asn Thr Glu Asn Arg Ser Leu Arg Leu
                195                 200                 205

Gly Val Glu Lys Lys Lys Ile Arg Gly Leu Leu Val Gly Pro Lys Ile
```

Asp Glu Asp Ala Lys Glu Met Ile Glu Glu Gly Ile Glu Phe Val
225                 230                 235                 240

Glu Cys Glu Pro Pro Lys Glu Leu Lys Arg Asp Lys Lys Thr Thr Leu
            245                 250                 255

Asp Ser Phe

<210> SEQ ID NO 17
<211> LENGTH: 260
<212> TYPE: PRT
<213> ORGANISM: Methanobrevibacter arboriphilus

<400> SEQUENCE: 17

Met Lys Tyr Lys Leu Leu Glu Asn Pro Asp Ile Glu Glu Ala Tyr Asp
1               5                   10                  15

Leu Ile Asp Ser Gly Ile Arg Lys Lys Ala Val Ile Asn Ile Phe Ala
            20                  25                  30

Tyr Cys Lys Val Leu Tyr Glu Gly Arg Ala Leu Ser Gln Leu Asp Trp
        35                  40                  45

Gly Glu Arg Phe Ile Met Leu Lys Pro Asp Gly Ser Phe Leu Val His
50                  55                  60

Gln Glu Arg Lys Ile Asp Pro Val Asn Trp Gln Pro Pro Lys Ser Arg
65                  70                  75                  80

His Arg Ala Leu Ile Lys Glu Asn Asn Leu Ile Leu Glu Ser His Arg
                85                  90                  95

Arg Thr Pro Lys Glu Lys Leu Glu Val Glu Ile Glu Lys Val His Phe
            100                 105                 110

Ala Ser Phe Ala Leu Ala Glu Asp Tyr Gln Glu Leu Glu Leu Ala Gly
        115                 120                 125

Tyr Glu Lys Asp Met Gly Asp Met Ile Ile Lys His Pro Asn Met Ile
130                 135                 140

Glu Gln Gly Phe Thr Pro Thr Ala Arg Glu Tyr Asn Thr Glu His Gly
145                 150                 155                 160

Phe Ile Asp Ile Leu Gly Lys Asp Ile Glu Gly Asn Ile Val Val Val
                165                 170                 175

Glu Leu Lys Cys Arg Lys Ala Gly Thr Asn Ala Val Lys Gln Ile Arg
            180                 185                 190

Arg Tyr Leu Lys Asp Phe Glu Glu Asn Asp Asn Asp Tyr Leu Lys Glu
        195                 200                 205

Ile Lys Ser Lys Lys Lys Ile Arg Gly Leu Leu Val Ala Pro Asp
210                 215                 220

Ile Asn Glu Asp Ala Lys Glu Leu Leu Glu Glu Gly Ile Glu Phe
225                 230                 235                 240

Lys Ala Val Asp Pro Pro Lys Glu Leu Lys Ser Asp Lys Lys Val Thr
            245                 250                 255

Leu Asp Ile Phe
            260

<210> SEQ ID NO 18
<211> LENGTH: 261
<212> TYPE: PRT
<213> ORGANISM: Methanobrevibacter arboriphilus

<400> SEQUENCE: 18

Met Lys Tyr Lys Leu Leu Glu Asn Pro Asp Ile Glu Glu Thr Tyr Asp
1               5                   10                  15

```
Leu Ile Asp Ser Gly Ile Arg Lys Lys Ala Val Ile Asn Ile Phe Ala
            20                  25                  30

Tyr Cys Lys Val Leu Tyr Glu Gly Arg Ala Leu Ser Gln Leu Asp Trp
            35                  40                  45

Gly Gly Glu Arg Phe Ile Met Leu Lys Pro Asp Gly Ser Phe Leu Val
 50                  55                  60

His Gln Glu Arg Lys Ile Asp Pro Val Asn Trp Gln Pro Pro Lys Ser
65                  70                  75                  80

Arg His Arg Ala Leu Ile Lys Glu Asn Asn Leu Ile Leu Glu Ser His
                85                  90                  95

Arg Arg Thr Pro Lys Glu Lys Leu Glu Val Glu Ile Glu Lys Val His
            100                 105                 110

Phe Ala Ser Phe Ala Leu Ala Glu Asp Tyr Gln Glu Leu Glu Leu Ala
            115                 120                 125

Gly Tyr Glu Lys Asp Met Gly Asp Met Ile Ile Lys His Pro Asn Met
130                 135                 140

Ile Glu Gln Gly Phe Thr Pro Thr Ala Arg Glu Tyr Asn Thr Glu His
145                 150                 155                 160

Gly Phe Ile Asp Ile Leu Gly Lys Asp Ile Glu Gly Asn Ile Val Val
                165                 170                 175

Val Glu Leu Lys Cys Arg Lys Ala Gly Thr Asn Ala Val Lys Gln Ile
            180                 185                 190

Arg Arg Tyr Leu Lys Asp Phe Glu Glu Asn Asp Asn Asp Tyr Leu Lys
            195                 200                 205

Glu Ile Lys Ser Lys Lys Lys Ile Arg Gly Leu Leu Val Ala Pro
            210                 215                 220

Asp Ile Asn Glu Asp Ala Lys Glu Leu Leu Glu Glu Glu Gly Ile Glu
225                 230                 235                 240

Phe Lys Ala Val Asp Pro Pro Lys Glu Leu Lys Ser Asp Lys Lys Val
            245                 250                 255

Thr Leu Asp Ile Phe
            260

<210> SEQ ID NO 19
<211> LENGTH: 260
<212> TYPE: PRT
<213> ORGANISM: Methanobrevibacter arboriphilus

<400> SEQUENCE: 19

Met Lys Tyr Lys Leu Leu Glu Asn Pro Asp Ile Glu Glu Thr Tyr Asp
1               5                   10                  15

Leu Ile Asp Ser Gly Ile Arg Lys Lys Ala Val Ile Asn Ile Phe Ala
            20                  25                  30

Tyr Cys Lys Val Leu Tyr Glu Gly Arg Ala Leu Ser Gln Leu Asp Trp
            35                  40                  45

Gly Glu Arg Phe Ile Met Leu Lys Pro Asp Gly Ser Phe Leu Val His
 50                  55                  60

Gln Glu Arg Lys Ile Asp Pro Val Asn Trp Gln Pro Pro Lys Ser Arg
65                  70                  75                  80

His Arg Ala Leu Ile Lys Glu Asn Asn Leu Ile Leu Glu Ser His Arg
                85                  90                  95

Arg Thr Pro Lys Glu Lys Leu Glu Val Glu Ile Glu Lys Val His Phe
            100                 105                 110

Ala Ser Phe Ala Leu Ala Glu Asp Tyr Gln Glu Leu Glu Leu Ala Gly
```

```
            115                 120                 125
Tyr Glu Lys Asp Met Gly Asp Met Ile Ile Lys His Pro Asn Met Ile
    130                 135                 140

Glu Gln Gly Phe Thr Pro Thr Ala Arg Glu Tyr Asn Thr Glu His Gly
145                 150                 155                 160

Phe Ile Asp Ile Leu Gly Lys Asp Ile Glu Gly Asn Ile Val Val Val
                165                 170                 175

Glu Leu Lys Cys Arg Lys Ala Gly Ile Asn Ala Val Lys Gln Ile Arg
            180                 185                 190

Arg Tyr Leu Lys Asp Phe Glu Glu Asn Asp Asn Asp Tyr Leu Lys Glu
        195                 200                 205

Val Lys Ser Lys Lys Lys Ile Arg Gly Leu Leu Val Ala Pro Asp
    210                 215                 220

Ile Asn Glu Asp Ala Lys Glu Leu Leu Glu Glu Glu Gly Ile Glu Phe
225                 230                 235                 240

Lys Ala Val Asp Pro Pro Lys Glu Leu Arg Ser Asp Lys Lys Val Thr
                245                 250                 255

Leu Asp Ile Phe
            260

<210> SEQ ID NO 20
<211> LENGTH: 259
<212> TYPE: PRT
<213> ORGANISM: Methanobrevibacter wolinii

<400> SEQUENCE: 20

Met Asn Tyr Lys Asn Ile Glu Lys Pro Asn Ile Asn Glu Ser Tyr Asn
1               5                   10                  15

Phe Ile Glu Glu Gly Leu Arg Lys Arg Ala Thr Ile Ser Leu Tyr Thr
                20                  25                  30

Tyr Cys Lys Val Glu Tyr Glu Gly Arg Ala Leu Ser Gln Leu Asn Tyr
            35                  40                  45

Gly Glu Arg Leu Ile Ile Lys Pro Asp Gly Ser Phe Leu Ile His
    50                  55                  60

Gln Asn Lys Lys Val Glu Pro Val Asn Trp Gln Pro Pro Lys Ser Arg
65                  70                  75                  80

Thr Lys Val Tyr Ile Lys Asn Asn Lys Leu Phe Leu Glu Ser Asn Arg
                85                  90                  95

Lys Thr Pro Arg Glu Arg Leu Glu Val Glu Ile Asn Asn Ile Glu Thr
            100                 105                 110

Gly Thr Tyr Ala Ile Leu Glu Asp Tyr Glu Glu Leu Glu Gln Ala Gly
        115                 120                 125

Tyr Glu Lys Asp Met Gly Asp Met Ile Met Lys Asn Pro His Ile Ile
    130                 135                 140

Glu Glu Gly Phe Lys Pro Ser Ser Arg Glu Tyr Ser Val Asn Ser Gly
145                 150                 155                 160

Phe Ile Asp Ile Leu Gly Lys Asp Lys Asn Gly Asn Leu Met Val Leu
                165                 170                 175

Glu Leu Lys Ser Arg Lys Ile Gly Val Ser Ala Val Lys Gln Ile Arg
            180                 185                 190

Arg Tyr Val Glu Asp Leu Lys Asn Thr Glu Lys Glu Phe Glu Thr
        195                 200                 205

Asp Asn Asn Lys Lys Arg Ile Arg Gly Ile Leu Val Ala Pro Lys Ile
    210                 215                 220
```

```
Asp Asn Asp Ala Lys Glu Met Ile Glu Glu Asn Phe Glu Phe Val
225                 230                 235                 240

Ala Cys Glu Pro Pro Lys Glu Leu Lys Lys Asp Lys Val Thr Leu
            245                 250                 255

Asp Leu Phe

<210> SEQ ID NO 21
<211> LENGTH: 249
<212> TYPE: PRT
<213> ORGANISM: Methanothermobacter wolfeii

<400> SEQUENCE: 21

Met Lys Cys Gln Val Phe Glu Asn Pro Ser Pro Lys Lys Ala Tyr Arg
1               5                   10                  15

Val Ile Glu Glu Gly Ile Arg Lys Arg Val Leu Ile Val Ile Leu Ala
            20                  25                  30

Cys Cys Ser Ala Ser Tyr Glu Gly Arg Ala Arg Ser Arg Leu Glu Pro
        35                  40                  45

Gly Glu Arg Leu Ile Val Ile Lys Pro Asp Gly Thr Phe Met Ile His
    50                  55                  60

Gln Asp Arg Lys Val Asp Pro Val Asn Trp Gln Pro Pro Arg Ser Arg
65                  70                  75                  80

Cys Arg Ser Tyr Met Lys Gly Gly Lys Leu Tyr Leu Glu Ser Ile Arg
                85                  90                  95

Arg Ser Pro Glu Glu Arg Leu Glu Val Glu Ile His Glu Ala His Leu
            100                 105                 110

Val Ser Cys Tyr Thr Ala Arg Asp Arg His Glu Leu Glu Val Ala Gly
        115                 120                 125

His Glu Arg Asp Met Gly Asp Met Ile Met Glu His Pro His Leu Ile
    130                 135                 140

Glu Lys Gly Phe Arg Pro Val Ala Arg Glu Tyr Ser Thr Asp Ala Gly
145                 150                 155                 160

Phe Ile Asp Ile Leu Gly Lys Asp Glu Asn Gly Ser Leu Val Ile Ile
                165                 170                 175

Glu Leu Lys Ser Arg Lys Ala Gly Val Ser Ala Val Lys Gln Leu Lys
            180                 185                 190

Arg Tyr Leu Asp Glu Phe Arg Asp Asp Arg Gly Val Arg Gly Met
        195                 200                 205

Leu Val Ala Pro Ser Ile Thr His Asp Ala Met Glu Met Leu Glu Asp
    210                 215                 220

Glu Gly Leu Glu Phe Arg Ser Leu Glu Pro Leu Arg Glu Leu Arg Ser
225                 230                 235                 240

Ala Arg Gly Val Thr Leu Asp Asn Phe
                245

<210> SEQ ID NO 22
<211> LENGTH: 249
<212> TYPE: PRT
<213> ORGANISM: Methanobacteriaceae archaeon

<400> SEQUENCE: 22

Met Arg Phe Ile Ser Leu Glu Asn Pro Thr Ser Glu Glu Ser Cys Arg
1               5                   10                  15

Ile Ile Lys Glu Gly Leu Arg Lys Lys Ala Met Ile Ile Ile Phe Ser
            20                  25                  30

Cys Cys Lys Val Arg Tyr Tyr Gly Arg Ala Lys Ser Arg Leu Gly Pro
```

```
            35                  40                  45
Gly Glu Arg Leu Ile Ile Ile Lys Pro Asp Gly Ser Phe Leu Ile His
 50                  55                  60

Gln Asp Arg Lys Val Glu Pro Val Asn Trp Gln Pro Pro Gly Ser Lys
 65                  70                  75                  80

Ala Lys Val Lys Ile Glu Asp Gly Lys Ile Leu Val Glu Ser Ile Arg
                 85                  90                  95

Arg Lys Pro Ala Glu Lys Leu Met Val Glu Met Glu Lys Val His Thr
             100                 105                 110

Leu Ser Tyr Tyr Leu Val Lys Asp Val His Glu Leu Glu Val Ala Gly
         115                 120                 125

His Glu Glu Asp Met Arg Arg Leu Ile Leu Glu Ser Pro Asp Ile Ile
     130                 135                 140

Glu Lys Gly Phe Arg Pro Ile Thr Arg Glu Tyr Gln Thr Ser Asn Gly
145                 150                 155                 160

Phe Ile Asp Ile Leu Gly Lys Asp Glu Asn Gly Ser Leu Met Val Leu
                 165                 170                 175

Glu Leu Lys Ser Arg Arg Ala Gly Val Ser Ala Val Arg Gln Leu Lys
             180                 185                 190

Arg Tyr Leu Glu Asp Phe Lys Asp Lys His Gly Val Arg Gly Val
         195                 200                 205

Leu Val Ala Pro Ser Ile Thr His Asp Ala Arg Glu Leu Leu Glu Ala
     210                 215                 220

Glu Gly Leu Glu Phe Lys Ser Leu Glu Pro Pro Arg Glu Leu Lys Lys
225                 230                 235                 240

Gly Tyr Lys Met Thr Leu Asp Lys Phe
                 245

<210> SEQ ID NO 23
<211> LENGTH: 249
<212> TYPE: PRT
<213> ORGANISM: Methanothermobacter thermautotrophicus

<400> SEQUENCE: 23

Met Lys Cys Lys Val Ser Glu Asn Pro Ser Ile Lys Glu Ala Tyr Arg
  1               5                  10                  15

Leu Ile Glu Asp Gly Ile Arg Lys Arg Ala Leu Val Val Ile Leu Ala
                 20                  25                  30

Cys Cys Ser Ala Ser Tyr Glu Gly Arg Ala Arg Ser Arg Leu Asp Ala
             35                  40                  45

Gly Glu Arg Leu Ile Val Ile Lys Pro Asp Gly Thr Phe Met Val His
 50                  55                  60

Gln Asp Arg Lys Val Asp Pro Val Asn Trp Gln Pro Pro Lys Ser Arg
 65                  70                  75                  80

Ser Arg Ala Tyr Ile Lys Arg Gly Ser Leu Tyr Leu Glu Ser Ile Arg
                 85                  90                  95

Arg Asp Pro Glu Glu Arg Leu Glu Val Glu Ile His Glu Ala His Leu
             100                 105                 110

Val Ser Tyr Tyr Leu Ala Arg Asp Val His Asp Leu Met Val Ala Gly
         115                 120                 125

His Glu Asn Asp Met Gly Asp Met Ile Met His Pro His Leu Ile
     130                 135                 140

Glu Lys Gly Phe Arg Pro Val Ala Arg Glu Tyr Ala Val Thr Ser Gly
145                 150                 155                 160
```

```
Phe Ile Asp Ile Leu Gly Lys Asp Glu Asn Gly Ser Leu Met Ile Ile
                165                 170                 175

Glu Leu Lys Ser Arg Lys Ala Gly Val Ser Ala Val Lys Gln Leu Lys
            180                 185                 190

Arg Tyr Val Asp Glu Phe Arg Glu Asp Arg Val Gly Val Arg Gly Val
        195                 200                 205

Leu Val Ala Pro Ser Ile Thr His Asp Ala Met Glu Met Leu Glu Glu
    210                 215                 220

Glu Gly Leu Glu Phe Arg Glu Ile Glu Pro Pro Arg Glu Leu Arg Ser
225                 230                 235                 240

Asn Arg Gly Val Thr Leu Asp Asn Phe
                245
```

<210> SEQ ID NO 24
<211> LENGTH: 249
<212> TYPE: PRT
<213> ORGANISM: Methanothermobacter thermautotrophicus str. Delta H

<400> SEQUENCE: 24

```
Met Lys Cys Lys Val Ser Glu Asn Pro Ser Ile Lys Glu Ala Tyr Arg
1               5                   10                  15

Leu Ile Glu Asp Gly Ile Arg Lys Arg Ala Leu Val Ile Leu Ala
            20                  25                  30

Cys Cys Ser Ala Ser Tyr Glu Gly Arg Ala Arg Ser Arg Leu Asp Ala
        35                  40                  45

Gly Glu Arg Leu Ile Val Ile Lys Pro Asp Gly Thr Phe Met Val His
    50                  55                  60

Gln Asp Arg Lys Val Asp Pro Val Asn Trp Gln Pro Pro Lys Ser Arg
65                  70                  75                  80

Ser Arg Ala Tyr Ile Lys Arg Gly Ser Leu Tyr Leu Glu Ser Ile Arg
                85                  90                  95

Arg Asp Pro Glu Glu Arg Leu Glu Val Glu Ile His Glu Ala His Leu
            100                 105                 110

Val Ser Tyr Tyr Leu Ala Arg Asp Val His Asp Leu Met Val Ala Gly
        115                 120                 125

His Glu Asn Asp Met Gly Asp Met Ile Ile Met His Pro His Leu Ile
    130                 135                 140

Glu Lys Gly Phe Arg Pro Val Ala Arg Glu Tyr Ala Val Thr Ser Gly
145                 150                 155                 160

Phe Ile Asp Ile Leu Gly Lys Asp Glu Asn Gly Ser Leu Met Ile Ile
                165                 170                 175

Glu Leu Lys Ser Arg Lys Ala Gly Val Ser Ala Val Lys Gln Leu Lys
            180                 185                 190

Arg Tyr Val Asp Glu Phe Arg Glu Asp Arg Val Gly Val Arg Gly Val
        195                 200                 205

Leu Val Ala Pro Ser Ile Thr His Asp Ala Met Glu Met Leu Glu Glu
    210                 215                 220

Glu Gly Leu Glu Phe Arg Glu Ile Glu Pro Pro Arg Glu Leu Arg Ser
225                 230                 235                 240

Asn Arg Gly Val Thr Leu Asp Asn Phe
                245
```

<210> SEQ ID NO 25
<211> LENGTH: 249
<212> TYPE: PRT
<213> ORGANISM: Methanothermobacter

<400> SEQUENCE: 25

```
Met Lys Cys Arg Val Ser Glu Asn Pro Ser Arg Asn Glu Ala Tyr Gln
1               5                   10                  15

Leu Leu Glu Glu Gly Ile Arg Lys Arg Ser Leu Ile Val Ile Leu Ala
            20                  25                  30

Cys Cys Ser Ala Ser Tyr Glu Gly Arg Ala Arg Ser Ser Leu Gly Ala
        35                  40                  45

Gly Glu Arg Leu Ile Val Ile Lys Pro Asp Gly Thr Phe Met Val His
    50                  55                  60

Gln Asp Arg Lys Val Asp Pro Val Asn Trp Gln Pro Pro Arg Ser Arg
65                  70                  75                  80

Cys Arg Val Tyr Met Lys Arg Gly Ser Leu Phe Leu Glu Ser Ile Arg
                85                  90                  95

Arg Ser Pro Glu Glu Arg Leu Glu Val Glu Leu His Glu Ile His Leu
            100                 105                 110

Ile Ser Ser Tyr Leu Pro Arg Asp Met His Glu Leu Thr Val Ser Gly
        115                 120                 125

His Glu Ser Asp Met Gly Asp Met Ile Ile Met His Pro His Leu Ile
    130                 135                 140

Glu Pro Gly Phe Arg Pro Val Ala Arg Glu Tyr Ala Thr Ser Ser Gly
145                 150                 155                 160

Phe Ile Asp Ile Leu Gly Lys Asp Glu Asn Gly Ser Leu Met Ile Ile
                165                 170                 175

Glu Leu Lys Ser Arg Lys Ala Gly Val Ser Ala Val Lys Gln Leu Arg
            180                 185                 190

Arg Tyr Val Asp Glu Phe Arg Asp Asp Arg Val Gly Val Arg Gly Ile
        195                 200                 205

Leu Val Ala Pro Ser Ile Thr His Asp Ala Leu Glu Met Leu Glu Asp
    210                 215                 220

Glu Gly Leu Glu Phe Arg Glu Ile Glu Pro Pro Arg Glu Leu Lys Ser
225                 230                 235                 240

Asn Arg Gly Val Thr Leu Asp Asn Phe
                245
```

<210> SEQ ID NO 26
<211> LENGTH: 248
<212> TYPE: PRT
<213> ORGANISM: Methanothermobacter

<400> SEQUENCE: 26

```
Arg Phe Lys Thr Ile Glu Asn Pro Ser Pro Lys Glu Ser His Glu Leu
1               5                   10                  15

Ile Ser Glu Gly Leu Arg Lys Lys Ala Met Ile Ile Leu Phe Ala Cys
            20                  25                  30

Cys Lys Val Gln Tyr His Gly Arg Ala Lys Ser Arg Leu Gly Thr Gly
        35                  40                  45

Glu Arg Leu Ile Ile Ile Lys Pro Asp Gly Ser Phe Leu Ile His Gln
    50                  55                  60

Asp Arg Lys Val Asp Pro Val Asn Trp Gln Pro Pro Gly Ser Lys Thr
65                  70                  75                  80

Lys Ile Lys Ile Glu Asn Gly Lys Ile Leu Leu Glu Ser Arg Arg Arg
                85                  90                  95

Lys Pro Pro Glu Lys Leu Thr Ala Glu Ile Lys Arg Ile His Ser Leu
            100                 105                 110
```

```
Ser Tyr His Leu Ala Arg Asp Ala His Glu Leu Gln Val Thr Gly His
        115                 120                 125

Glu Glu Asp Met Arg Gln Leu Ile Leu Glu Ser Pro Asp Ile Ile Glu
    130                 135                 140

Lys Gly Phe Arg Pro Thr Thr Ser Glu Tyr Pro Thr Ser Asn Gly Phe
145                 150                 155                 160

Ile Asp Ile Leu Gly Lys Asp Lys Asn Gly Ser Leu Met Ile Leu Glu
                165                 170                 175

Leu Lys Ser Arg Arg Ala Gly Leu Asn Ala Val Arg Gln Leu Lys Arg
            180                 185                 190

Tyr Leu Lys Asp Phe Lys Asp Lys His Gly Val Arg Gly Val Leu
        195                 200                 205

Val Ala Pro Ser Ile Thr His Asp Ala Lys Glu Leu Leu Glu Lys Glu
    210                 215                 220

Gly Leu Glu Phe Lys Ser Leu Lys Pro Pro Gln Glu Leu Lys Lys Asp
225                 230                 235                 240

His Lys Ile Thr Leu Asp Lys Phe
                245
```

<210> SEQ ID NO 27
<211> LENGTH: 249
<212> TYPE: PRT
<213> ORGANISM: Methanothermobacter marburgensis

<400> SEQUENCE: 27

```
Met Lys Cys Arg Val Ser Glu Asn Pro Ser Arg Ser Glu Ala Tyr Arg
1               5                   10                  15

Leu Leu Glu Glu Gly Ile Arg Lys Arg Ser Leu Ile Val Ile Leu Ala
            20                  25                  30

Cys Cys Ser Ala Ser Tyr Glu Gly Arg Ala Arg Ser Ser Leu Gly Ala
        35                  40                  45

Gly Glu Arg Leu Ile Val Ile Lys Pro Asp Gly Thr Phe Met Val His
    50                  55                  60

Gln Asp Arg Lys Val Asp Pro Val Asn Trp Gln Pro Pro Arg Ser Arg
65                  70                  75                  80

Cys Arg Val Tyr Met Lys Gln Lys Ser Leu Phe Leu Glu Ser Ile Arg
                85                  90                  95

Arg Ser Pro Glu Glu Arg Leu Glu Val Glu Leu His Glu Val His Leu
            100                 105                 110

Ile Ser Phe Tyr Leu Pro Arg Asp Met His Glu Leu Thr Val Ser Gly
        115                 120                 125

His Glu Ser Asp Met Gly Asp Met Ile Ile Met His Pro His Leu Ile
    130                 135                 140

Glu Pro Gly Phe Arg Pro Val Ala Arg Glu Tyr Ala Thr Ser Ser Gly
145                 150                 155                 160

Phe Ile Asp Ile Leu Gly Lys Asp Glu Asn Gly Ser Leu Met Ile Ile
                165                 170                 175

Glu Leu Lys Ser Arg Lys Ala Gly Val Ser Ala Val Lys Gln Leu Arg
            180                 185                 190

Arg Tyr Val Asp Glu Phe Arg Asp Gln Val Gly Val Arg Gly Ile
        195                 200                 205

Leu Val Ala Pro Ser Ile Thr His Asp Ala Leu Glu Met Leu Glu Asp
    210                 215                 220

Glu Gly Leu Glu Phe Arg Glu Ile Glu Pro Pro Arg Glu Leu Lys Ser
```

```
                225                 230                 235                 240

Asn Arg Gly Val Thr Leu Asp Asn Phe
                245

<210> SEQ ID NO 28
<211> LENGTH: 249
<212> TYPE: PRT
<213> ORGANISM: Methanobacterium

<400> SEQUENCE: 28

Met Ile Ile Lys Leu Asp Glu Asn Pro Gly Thr Glu Glu Val Phe Asp
1               5                   10                  15

Phe Ile Asn Glu Ala Ile Ser Lys Arg Ala Phe Ile Ile Val Ala
            20                  25                  30

Cys Cys Arg Ile Lys Tyr Arg Gly Arg Ala Thr Ser Arg Leu Gly Ser
        35                  40                  45

Gly Asp Arg Thr Ile Ile Lys Thr Asp Gly Ser Phe Leu Val His
    50                  55                  60

Gln Asp Tyr Asn Leu Glu Pro Val Asn Trp Gln Pro Asn Cys Lys
65                  70                  75                  80

Phe Lys Thr Arg Met Glu Asn Gly Arg Val Tyr Leu Cys Gly Val Arg
                85                  90                  95

Arg Asn Pro Pro Glu Ser Leu Glu Val Glu Ile Cys Lys Thr His Met
            100                 105                 110

Ile Ser Tyr His Ile Gly Lys Asp Ile Lys Lys Leu Glu Leu Ala Gly
        115                 120                 125

Tyr Glu Glu Asp Met Arg Ala Met Ile Met Glu Ser Pro Glu Leu Ile
    130                 135                 140

Glu Lys Gly Phe Arg Pro Thr Ser Lys Glu Tyr Pro Val Ser Thr Gly
145                 150                 155                 160

Phe Ile Asp Ile Leu Gly Lys Asp Lys Asn Gly Ser Leu Met Val Leu
                165                 170                 175

Glu Leu Lys Ser Arg Gln Ala Gly Ile Asn Ala Val Lys Gln Leu Lys
            180                 185                 190

Lys Tyr Phe Glu Asp Phe Thr Asp His Lys Asp Phe Val Arg Gly Leu
        195                 200                 205

Leu Val Ala Pro Ser Ile Thr Glu Asp Ala Gln Glu Leu Leu Glu Lys
    210                 215                 220

Tyr Gln Leu Glu Phe Lys Ala Leu Glu Pro Pro Lys Glu Leu Lys Ser
225                 230                 235                 240

Ala Lys Ser Val Thr Leu Asp Phe Phe
                245

<210> SEQ ID NO 29
<211> LENGTH: 249
<212> TYPE: PRT
<213> ORGANISM: Methanobacterium paludis

<400> SEQUENCE: 29

Met Lys Phe Leu Ser Glu Lys Asn Pro Asp Ile Lys Arg Thr Tyr Glu
1               5                   10                  15

Ile Ile Asn Glu Gly Ile Ser Lys Arg Ala Val Ile Val Ile Met Ala
            20                  25                  30

Cys Cys Ser Val Leu Tyr Glu Gly Arg Ala Arg Ser Arg Leu Ala Asp
        35                  40                  45

Gly Asp Arg Met Val Met Ile Lys Thr Asp Gly Ser Phe Leu Val His
```

```
                50                  55                  60
Gln Asp Arg Asn Leu Glu Pro Val Asn Trp Gln Pro Pro Lys Ser Gln
 65                  70                  75                  80

Cys Lys Ala Ser Leu Lys Glu Gly Leu Leu His Ile Glu Gly Ala Arg
                 85                  90                  95

Arg Asn Pro Pro Glu Arg Leu Glu Val Glu Ile His Ser Thr Tyr Met
                100                 105                 110

Ala Ser Tyr Phe Ile Gly Glu Asp Ser Lys Asp Leu Glu Leu Ala Gly
                115                 120                 125

Tyr Glu Ala Asp Met Val Asp Met Ala Phe Glu Ser Pro Glu Leu Ile
                130                 135                 140

Glu Lys Gly Phe Arg Pro Thr Ser Arg Glu Tyr Ser Thr Glu Asn Gly
145                 150                 155                 160

Phe Ile Asp Ile Leu Gly Lys Asp Gln Asp Gly Asn Leu Met Val Leu
                165                 170                 175

Glu Phe Lys Ser Arg Arg Ala Gly Ile Asn Ala Val Lys Gln Leu Lys
                180                 185                 190

Arg Tyr Leu Asp Cys Phe Ala Asp His Lys Gln Phe Val Arg Gly Leu
                195                 200                 205

Leu Val Ala Pro Ser Val Thr Asp Ala Ser Asp Leu Leu Lys Glu
                210                 215                 220

Tyr Lys Leu Glu Phe Lys Glu Leu Glu Pro Pro Met Glu Phe Asp Gly
225                 230                 235                 240

Asp Lys Asn Leu Thr Leu Asp Phe Phe
                245

<210> SEQ ID NO 30
<211> LENGTH: 249
<212> TYPE: PRT
<213> ORGANISM: Methanobacterium

<400> SEQUENCE: 30

Met Ile Ile Lys Leu Asp Glu Asn Pro Gly Thr Glu Glu Val Phe Asp
 1                   5                  10                  15

Phe Ile Asn Glu Ala Ile Ser Lys Arg Ala Phe Ile Ile Val Ala
                 20                  25                  30

Cys Cys Arg Ile Lys Tyr Arg Gly Arg Ala Thr Ser Arg Leu Gly Ser
                 35                  40                  45

Gly Asp Arg Thr Ile Ile Lys Thr Asp Gly Ser Phe Leu Val His
                 50                  55                  60

Gln Asp Tyr Asn Leu Glu Pro Val Asn Trp Gln Pro Pro Asn Cys Lys
 65                  70                  75                  80

Phe Lys Thr Arg Met Glu Asn Asp Arg Val Tyr Ile Cys Gly Val Arg
                 85                  90                  95

Arg Asn Pro Pro Glu Ser Leu Glu Val Glu Ile Cys Lys Thr His Met
                100                 105                 110

Ile Ser Tyr His Ile Gly Lys Asp Ile Lys Lys Leu Glu Leu Ala Gly
                115                 120                 125

Tyr Glu Glu Asp Leu Arg Thr Met Ile Met Glu Ser Pro Glu Leu Ile
                130                 135                 140

Glu Lys Gly Phe Arg Pro Thr Ser Lys Glu Tyr Gln Val Ser Thr Gly
145                 150                 155                 160

Phe Ile Asp Ile Leu Gly Lys Asp Lys Asn Gly Ser Leu Met Ile Leu
                165                 170                 175
```

```
Glu Leu Lys Ser Arg Gln Ala Gly Val Asn Ala Val Lys Gln Leu Lys
            180                 185                 190

Lys Tyr Phe Glu Asp Phe Thr Asp His Lys Asp Phe Val Arg Gly Leu
        195                 200                 205

Leu Val Ala Pro Ser Val Thr Glu Asp Ala Gln Glu Leu Leu Glu Lys
    210                 215                 220

Tyr Gln Leu Glu Phe Lys Ala Leu Glu Pro Pro Lys Glu Leu Lys Ser
225                 230                 235                 240

Ala Lys Ser Val Thr Leu Asp Phe Phe
                245

<210> SEQ ID NO 31
<211> LENGTH: 248
<212> TYPE: PRT
<213> ORGANISM: Palaeococcus ferrophilus

<400> SEQUENCE: 31

Met Lys Leu Arg Ala Leu Glu Asn Pro Ser Ala Glu Glu Leu Glu Ser
1               5                   10                  15

Ile Ile Ser Glu Gly Leu Ser Ser Glu Ala Ile Ile Thr Ile Phe Ala
            20                  25                  30

Arg Cys Arg Val Tyr Tyr Asp Gly Arg Ala Lys Ser Glu Leu Gly Glu
        35                  40                  45

Gly Asp Arg Val Ile Leu Ile Lys Pro Asp Gly Ser Phe Leu Ile His
    50                  55                  60

Gln Arg Asn Lys Arg Glu Pro Val Asn Trp Gln Pro Pro Gly Ser Ser
65                  70                  75                  80

Val Phe Phe Glu Arg Glu Lys Leu Arg Leu Val Ser Val Arg Arg Lys
                85                  90                  95

Pro Arg Glu Thr Leu Glu Val Glu Leu Leu Lys Val Tyr Leu Ala Thr
            100                 105                 110

Tyr Phe Gln Ala Glu Asp Ser Glu Glu Leu Thr Leu Ile Gly Ser Glu
        115                 120                 125

Ala Glu Met Arg Asp Tyr Ile Phe Asp His Pro Glu Val Ile Glu Glu
    130                 135                 140

Gly Phe Lys Pro Leu Phe Arg Glu Lys Pro Ile Lys His Gly Ile Val
145                 150                 155                 160

Asp Ile Phe Gly Arg Asp Arg Asp Gly Asn Ile Val Ile Leu Glu Leu
                165                 170                 175

Lys Arg Arg Arg Ala Asp Leu His Ala Val Ser Gln Leu Lys Arg Tyr
            180                 185                 190

Val Glu Asp Met Arg Glu Glu Tyr Glu Asn Val Arg Gly Ile Leu Val
        195                 200                 205

Ala Pro Ser Leu Thr Ser Gly Ala Lys Lys Leu Leu Glu Lys Glu Gly
    210                 215                 220

Leu Glu Phe Arg Lys Val Lys Pro Pro Lys Gly Glu Arg Lys Lys Gly
225                 230                 235                 240

Lys Gln Lys Thr Leu Asp Ser Phe
                245

<210> SEQ ID NO 32
<211> LENGTH: 243
<212> TYPE: PRT
<213> ORGANISM: Methanobacterium

<400> SEQUENCE: 32
```

```
Lys Asn Pro Asp Thr Gln Arg Val Leu Glu Ile Ile Asn Glu Gly Leu
1               5                   10                  15

Ser Lys Arg Ala Val Ile Thr Ile Met Ala Cys Cys Arg Val Asp Tyr
            20                  25                  30

Asn Gly Arg Ala Val Ser Arg Leu Gly Leu Gly Asp Arg Ile Ile Ile
            35                  40                  45

Ile Lys Ala Asp Gly Ser Phe Leu Ile His Gln Asp Arg Asn Leu Glu
50                  55                  60

Pro Val Asn Trp Gln Pro Pro Lys Thr Lys Val Ser Ala Asp Ile Tyr
65                  70                  75                  80

Gln Gly Met Val Lys Ile Lys Gly Val Arg Arg Asn Pro His Glu Ser
            85                  90                  95

Leu Glu Val Lys Ile Leu Gln Thr His Met Ile Ser Tyr Phe Ile Gly
            100                 105                 110

Glu Asp Ser Glu Asn Leu Glu Leu Ala Gly Tyr Glu Ala Asp Met Gly
            115                 120                 125

Asp Leu Ile Phe Lys Asp Pro Asp Val Phe Glu Lys Gly Phe Arg Pro
    130                 135                 140

Thr Ser Arg Glu Tyr His Thr Pro Gln Gly Phe Ile Asp Ile Leu Gly
145                 150                 155                 160

Lys Asp Gln Asp Gly Asn Ile Thr Ile Leu Glu Leu Lys Ser Arg Lys
                165                 170                 175

Ala Gly Val Asn Ala Val Lys Gln Leu Arg Arg Tyr Leu Asp Cys Phe
                180                 185                 190

Ser Asp His Lys Glu Lys Val Arg Gly Val Leu Val Ala Pro Ser Ala
                195                 200                 205

Thr Asp Asp Ala Leu Glu Leu Leu Glu Lys Gln Gly Met Glu Phe Lys
    210                 215                 220

Ala Leu Glu Pro Pro Arg Glu Leu Asn Asn Glu Lys Val Val Thr Leu
225                 230                 235                 240

Glu Asn Phe

<210> SEQ ID NO 33
<211> LENGTH: 244
<212> TYPE: PRT
<213> ORGANISM: Pyrococcus abyssi

<400> SEQUENCE: 33

Ile Lys Glu Asn Pro Ser Glu Glu Ile Lys Glu Leu Leu Asp Leu
1               5                   10                  15

Ala Glu Lys His Gly Gly Val Val Thr Ile Phe Ala Arg Cys Lys Val
            20                  25                  30

His Tyr Glu Gly Arg Ala Lys Ser Glu Leu Gly Glu Gly Asp Arg Ile
            35                  40                  45

Ile Ile Ile Lys Pro Asp Gly Ser Phe Leu Ile His Gln Asn Lys Lys
50                  55                  60

Arg Glu Pro Val Asn Trp Gln Pro Pro Gly Ser Lys Val Thr Phe Lys
65                  70                  75                  80

Glu Asn Ser Ile Ile Ser Ile Arg Arg Arg Pro Tyr Glu Arg Leu Glu
            85                  90                  95

Val Glu Ile Ile Glu Pro Tyr Ser Leu Val Val Phe Leu Ala Glu Asp
            100                 105                 110

Tyr Glu Glu Leu Ala Leu Thr Gly Ser Glu Ala Glu Met Ala Asn Leu
            115                 120                 125
```

Ile Phe Glu Asn Pro Arg Val Ile Glu Glu Gly Phe Lys Pro Ile Tyr
130                 135                 140

Arg Glu Lys Pro Ile Arg His Gly Ile Val Asp Val Met Gly Val Asp
145                 150                 155                 160

Lys Asp Gly Asn Ile Val Val Leu Glu Leu Lys Arg Arg Lys Ala Asp
            165                 170                 175

Leu His Ala Val Ser Gln Leu Lys Arg Tyr Val Asp Ser Leu Lys Glu
            180                 185                 190

Glu Tyr Gly Glu Asn Val Arg Gly Ile Leu Val Ala Pro Ser Leu Thr
            195                 200                 205

Glu Gly Ala Lys Lys Leu Leu Glu Lys Glu Gly Leu Glu Phe Arg Lys
210                 215                 220

Leu Glu Pro Pro Lys Lys Gly Asn Glu Lys Arg Ser Lys Gln Lys Thr
225                 230                 235                 240

Leu Asp Phe Phe

<210> SEQ ID NO 34
<211> LENGTH: 249
<212> TYPE: PRT
<213> ORGANISM: Methanobacterium congolense

<400> SEQUENCE: 34

Met Lys Phe Leu Ser Glu Lys Asn Pro Asp Ile His Arg Thr Tyr Glu
1               5                   10                  15

Ile Ile Asn Glu Gly Ile Ser Lys Arg Ala Phe Val Val Leu Met Ala
            20                  25                  30

Cys Cys Lys Val Leu Tyr Gln Gly Arg Ala Lys Ser Arg Leu Gly Ser
            35                  40                  45

Gly Asp Arg Phe Ile Ile Lys Pro Asp Gly Ser Phe Met Val His
50                  55                  60

Gln Asp Arg Asn Leu Glu Pro Val Asn Trp Gln Pro Pro Lys Ser Asn
65                  70                  75                  80

Cys Lys Ala Ser Leu Glu Asn Gly Ile Leu Gln Ile Thr Gly Ser Arg
            85                  90                  95

Arg Asn Pro Pro Glu Ser Leu Glu Val Glu Ile His Cys Thr Tyr Met
            100                 105                 110

Ala Ser Tyr Phe Ile Gly Glu Asp Ser Lys Glu Leu Glu Ile Ala Gly
            115                 120                 125

Tyr Glu Glu Asn Met Arg Glu Met Val Phe Glu Ser Pro Glu Leu Ile
130                 135                 140

Glu Glu Gly Phe Arg Pro Thr Ser Arg Glu Tyr Gln Thr Glu Asn Gly
145                 150                 155                 160

Phe Ile Asp Ile Leu Gly Lys Asp Lys Asn Gly Ala Leu Met Val Leu
            165                 170                 175

Glu Leu Lys Ser Arg Arg Ala Gly Val Asn Ala Val Lys Gln Leu Lys
            180                 185                 190

Lys Tyr Leu Asp Cys Phe Thr Asp His Lys Glu Phe Val Arg Gly Val
            195                 200                 205

Leu Val Ala Pro Ser Val Thr Asp Asp Ala Met Glu Leu Leu Lys Glu
210                 215                 220

Tyr Gln Leu Glu Phe Lys Glu Leu His Pro Pro Met Glu Leu Gly Gly
225                 230                 235                 240

Gly Lys Asn Leu Thr Leu Asp Phe Phe
            245

<210> SEQ ID NO 35
<211> LENGTH: 249
<212> TYPE: PRT
<213> ORGANISM: Methanobacterium

<400> SEQUENCE: 35

Met Lys Phe Leu Ser Glu Lys Asn Pro Asp Gln Gln Arg Thr Phe Glu
1               5                   10                  15

Ile Ile Asn Glu Gly Leu Ser Lys Lys Ala Val Ile Val Leu Met Val
            20                  25                  30

Cys Cys Arg Val Ile Tyr Glu Gly Arg Ala Arg Ser Lys Leu Ala Ser
        35                  40                  45

Gly Asp Arg Met Ile Ile Ile Lys Ser Asp Gly Ser Phe Met Ile His
    50                  55                  60

Gln Asp Arg Asn Leu Glu Pro Val Asn Trp Gln Pro Pro Lys Ser Gln
65                  70                  75                  80

Cys Lys Ala Ser Leu Lys Lys Gly Ile Met Tyr Ile Glu Gly Lys Arg
                85                  90                  95

Arg Asn Pro Pro Glu Arg Leu Glu Val Glu Ile His Asn Thr Tyr Ile
            100                 105                 110

Ala Ser Tyr Phe Asn Gly Glu Asp Ser Lys Asp Leu Glu Leu Thr Gly
        115                 120                 125

Tyr Glu Glu Asn Met Arg Glu Leu Val Phe Glu Asn Pro Glu Ile Ile
    130                 135                 140

Glu Glu Gly Phe Arg Pro Ser Asn Arg Glu Tyr Ser Thr Pro Asn Gly
145                 150                 155                 160

Phe Ile Asp Val Leu Gly Lys Asp Lys Asn Gly Asn Leu Met Val Ile
                165                 170                 175

Glu Leu Lys Ser Arg Arg Ala Gly Ile Asn Ala Val Lys Gln Leu Lys
            180                 185                 190

Lys Tyr Leu Asp Cys Phe Ser Asp His Lys Glu Phe Val Arg Gly Ile
        195                 200                 205

Leu Val Ala Pro Ser Ile Thr Gly Asp Ala Glu Glu Leu Leu Glu Glu
    210                 215                 220

Tyr Lys Leu Glu Tyr Lys Ser Leu Glu Pro Pro Arg Glu Phe Gly Asn
225                 230                 235                 240

Asp Lys Asn Leu Thr Leu Asp Phe Phe
                245

<210> SEQ ID NO 36
<211> LENGTH: 242
<212> TYPE: PRT
<213> ORGANISM: Methanobacterium

<400> SEQUENCE: 36

Asn Pro Asp Thr Glu Leu Val Leu Glu Ile Ile Thr Glu Gly Ile Ser
1               5                   10                  15

Lys Arg Ala Phe Ile Thr Ile Met Ala Ser Cys Arg Val Tyr Tyr Glu
            20                  25                  30

Gly Arg Ala Thr Ser Arg Leu Glu Leu Gly Asp Arg Ile Ile Leu Ile
        35                  40                  45

Lys Ser Asp Gly Ser Phe Ile Ile His Gln Asp Arg Asn Leu Glu Pro
    50                  55                  60

Val Asn Trp Gln Pro Pro Lys Thr Lys Val Thr Val Asn Ile His Gln
65                  70                  75                  80

```
Gly Met Val Lys Leu Lys Gly Val Arg Arg Ser Pro Ser Glu Ser Leu
                85                  90                  95

Glu Val Glu Ile Leu Gln Thr His Leu Ala Ser Tyr Phe Ile Gly Glu
            100                 105                 110

Asp Ser Glu Ser Leu Glu Leu Ala Gly Tyr Glu Ala Asp Met Gly Asp
            115                 120                 125

Leu Ile Phe Lys Asp Pro Glu Val Ile Glu Lys Gly Phe Arg Pro Thr
130                 135                 140

Ser Arg Glu Tyr His Thr Pro Gln Gly Phe Ile Asp Ile Met Gly Lys
145                 150                 155                 160

Asp His Glu Gly Asn Ile Thr Ile Leu Glu Leu Lys Ser Arg Lys Ala
                165                 170                 175

Gly Thr Asn Ala Val Lys Gln Leu Arg Arg Tyr Val Asp Cys Phe Cys
            180                 185                 190

Asp His Lys Glu Lys Val Arg Gly Val Leu Val Ala Pro Ser Ala Thr
            195                 200                 205

Asp Asp Ala Leu Glu Met Leu Glu Gln Gly Met Glu Phe Lys Ala
210                 215                 220

Leu Glu Ala Pro Arg Glu Leu Lys Asn Asn Lys Ile Val Thr Leu Glu
225                 230                 235                 240

Ser Phe

<210> SEQ ID NO 37
<211> LENGTH: 244
<212> TYPE: PRT
<213> ORGANISM: Pyrococcus Abyssi
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid

<400> SEQUENCE: 37

Ile Lys Glu Asn Pro Ser Glu Glu Ile Lys Glu Leu Leu Asp Leu
1               5                   10                  15

Ala Glu Lys His Gly Gly Val Val Thr Ile Phe Ala Arg Cys Lys Val
                20                  25                  30

His Tyr Glu Gly Arg Ala Lys Ser Glu Leu Gly Glu Gly Asp Arg Ile
            35                  40                  45

Ile Ile Ile Lys Pro Asp Gly Ser Phe Leu Ile His Gln Asn Lys Lys
50                  55                  60

Arg Glu Pro Val Asn Trp Gln Pro Pro Gly Ser Lys Val Thr Phe Lys
65                  70                  75                  80

Glu Asn Ser Xaa Ile Ser Ile Arg Arg Arg Pro Tyr Glu Arg Leu Glu
                85                  90                  95

Val Glu Ile Ile Glu Pro Tyr Ser Leu Val Val Phe Leu Ala Glu Asp
            100                 105                 110

Tyr Glu Glu Leu Ala Leu Thr Gly Ser Glu Ala Glu Xaa Ala Asn Leu
            115                 120                 125
```

Ile Phe Glu Asn Pro Arg Val Ile Glu Glu Gly Phe Lys Pro Ile Tyr
130                 135                 140

Arg Glu Lys Pro Ile Arg His Gly Ile Val Asp Val Xaa Gly Val Asp
145                 150                 155                 160

Lys Asp Gly Asn Ile Val Val Leu Glu Leu Lys Arg Arg Lys Ala Asp
                165                 170                 175

Leu His Ala Val Ser Gln Xaa Lys Arg Tyr Val Asp Ser Leu Lys Glu
                180                 185                 190

Glu Tyr Gly Glu Asn Val Arg Gly Ile Leu Val Ala Pro Ser Leu Thr
                195                 200                 205

Glu Gly Ala Lys Lys Leu Leu Glu Lys Glu Gly Leu Glu Phe Arg Lys
210                 215                 220

Leu Glu Pro Pro Lys Lys Gly Asn Glu Lys Arg Ser Lys Gln Lys Thr
225                 230                 235                 240

Leu Asp Phe Phe

<210> SEQ ID NO 38
<211> LENGTH: 249
<212> TYPE: PRT
<213> ORGANISM: Methanosphaera

<400> SEQUENCE: 38

Met Lys Phe Lys Thr Ile Glu Asn Pro Glu Asn Asn Asp Ala Tyr Thr
1               5                   10                  15

Leu Leu Gln Glu Gly Phe Asp Lys Lys Ala Met Ile Ile Val Leu Ala
                20                  25                  30

Glu Cys His Val Glu Tyr Glu Gly Arg Ala Arg Ser Arg Leu Asp Ile
                35                  40                  45

Gly Asp Arg Leu Ile Leu Ile Lys Lys Asp Gly Thr Phe Val Ile His
            50                  55                  60

Gln Glu Leu Asn Leu Asp Pro Val Asn Trp Gln Ala Pro Gly Cys Lys
65                  70                  75                  80

Asn Lys Val Lys Leu Glu Asp Asn His Val Met Leu Ile Ser Lys Lys
                85                  90                  95

Thr Lys Pro Thr Glu Glu Ile Lys Val Phe Leu Asp Thr Ile Tyr Asn
                100                 105                 110

Ile Thr Tyr Tyr Asn Cys Leu Asp Thr Lys Asn Leu Glu Ile Arg Gly
            115                 120                 125

Tyr Glu Lys His Met Val Asp Leu Ala Trp Glu Lys Pro Glu Leu Ile
            130                 135                 140

Glu Lys Gly Phe Arg Pro Thr Arg Arg Glu Tyr Gln Thr Glu Asn Gly
145                 150                 155                 160

Phe Ile Asp Leu Met Gly Thr Asp Ile Asp Glu Lys Leu Met Ile Leu
                165                 170                 175

Glu Phe Lys Ser Arg Lys Ala Gly Thr Asn Ala Val Lys Gln Leu Lys
                180                 185                 190

Gly Tyr Ile Asp Cys Phe Lys Asp Asn Lys Glu Phe Val Arg Gly Ile
            195                 200                 205

Ile Val Ala Pro Asp Ile Thr Asp Asn Ala Arg Glu Leu Leu Glu Ser
            210                 215                 220

Leu Gln Met Glu Phe Ile Ser Met Asn Pro Pro Leu Asp Leu Leu Lys
225                 230                 235                 240

Gln Lys Ala Ser Thr Leu Asp Ser Phe
                245

<210> SEQ ID NO 39
<211> LENGTH: 250
<212> TYPE: PRT
<213> ORGANISM: Methanobacterium

<400> SEQUENCE: 39

Val Lys Phe Lys Val Glu Glu Asn Pro Ser Ile Glu Lys Thr Asn Glu
1               5                   10                  15

Leu Leu Lys Asp Gly Leu Lys Asn Lys Ala Ile Ile Ile Thr Ala
            20                  25                  30

Cys Cys Arg Val Phe Tyr Glu Gly Arg Ala Lys Ser Asn Leu Glu Leu
        35                  40                  45

Gly Asp Arg Val Ile Ile Ile Lys Pro Asp Gly Ser Phe Leu Ile His
    50                  55                  60

Lys Ser Glu Lys Arg Asn Pro Val Asn Trp Gln Pro Pro Gly Cys Thr
65                  70                  75                  80

Val Lys Phe Lys Val Lys Asp Asp Leu Met Leu Ile Arg Ser Ile Arg
                85                  90                  95

Lys Asn Pro Lys Glu Ile Leu Asp Val Glu Ile Ser Lys Thr Tyr Met
            100                 105                 110

Ala Thr Tyr Phe Val Ala Lys Asp Tyr Glu Glu Leu Asp Leu Ile Gly
        115                 120                 125

Ser Glu Glu Asp Met Ala Asn Leu Ile Phe Tyr Glu Asn Pro Glu Val
    130                 135                 140

Ile Glu Glu Gly Phe Lys Pro Ile Ala Lys Glu Lys Ser Ile Ser Asn
145                 150                 155                 160

Gly Val Ile Asp Ile Leu Gly Lys Asp Lys Asn Gly Asn Ile Met Val
                165                 170                 175

Leu Glu Leu Lys Arg Val Arg Gly Ser Leu Gly Ala Val Ser Gln Leu
            180                 185                 190

Lys Arg Tyr Val Asp Asn Leu Lys Glu Glu Asn Glu Gly Leu Arg Gly
        195                 200                 205

Met Leu Val Ala Pro Ser Ile Thr Asp Ser Ala Met Lys Leu Leu Lys
    210                 215                 220

Glu Tyr Gly Leu Glu Phe Lys Glu Leu His Pro Pro Lys Lys Leu Lys
225                 230                 235                 240

Lys Glu Asp Ile Ile Lys Leu Asp Phe Phe
                245                 250

<210> SEQ ID NO 40
<211> LENGTH: 250
<212> TYPE: PRT
<213> ORGANISM: Methanobacterium

<400> SEQUENCE: 40

Val Lys Phe Lys Val Glu Glu Asn Pro Asp Ile Glu Lys Thr Asn Glu
1               5                   10                  15

Ile Leu Lys Asp Gly Leu Lys Asn Lys Ala Ile Ile Ile Thr Ala
            20                  25                  30

Cys Cys Arg Val Phe Tyr Glu Gly Arg Ala Lys Ser Asn Leu Glu Leu
        35                  40                  45

Gly Asp Arg Val Ile Ile Ile Lys Pro Asp Gly Ser Phe Leu Ile His
    50                  55                  60

Lys Ser Glu Lys Arg Asn Pro Val Asn Trp Gln Pro Pro Gly Cys Thr
65                  70                  75                  80

Val Lys Phe Lys Val Lys Asp Asp Leu Met Leu Ile Arg Ser Ile Arg
             85                  90                  95

Lys Asn Pro Lys Glu Ile Leu Asp Val Glu Ile Ser Lys Thr Tyr Met
            100                 105                 110

Ala Thr Tyr Phe Val Ala Lys Asp Tyr Glu Glu Leu Asp Leu Ile Gly
            115                 120                 125

Ser Glu Glu Asp Met Ala Asn Leu Ile Phe Tyr Glu Asn Pro Glu Val
            130                 135                 140

Ile Glu Glu Gly Phe Lys Pro Ile Ala Lys Glu Lys Ser Ile Ser Asn
145                 150                 155                 160

Gly Val Ile Asp Ile Leu Gly Lys Asp Lys Asn Gly Asn Ile Met Val
                165                 170                 175

Leu Glu Leu Lys Arg Val Arg Gly Ser Leu Gly Ala Val Ser Gln Leu
            180                 185                 190

Lys Arg Tyr Val Asp Asn Leu Lys Glu Glu Asn Glu Gly Leu Arg Gly
            195                 200                 205

Met Leu Val Ala Pro Ser Ile Thr Asp Ser Ala Met Lys Leu Leu Lys
            210                 215                 220

Glu Tyr Gly Leu Glu Phe Lys Glu Leu His Pro Pro Lys Lys Leu Lys
225                 230                 235                 240

Lys Glu Asp Ile Ile Lys Leu Asp Phe Phe
                245                 250

<210> SEQ ID NO 41
<211> LENGTH: 249
<212> TYPE: PRT
<213> ORGANISM: Methanosphaera

<400> SEQUENCE: 41

Met Lys Tyr Lys Thr Ile Glu Asn Pro Ser Thr Gln Glu Ala Tyr Glu
1               5                   10                  15

Leu Ile Lys Asp Gly Phe Asn Lys Lys Ser Met Ile Ile Ile Leu Ala
            20                  25                  30

Gln Cys His Val Glu Tyr Glu Gly Arg Ala Arg Ser Arg Leu Asp Lys
            35                  40                  45

Gly Asp Arg Leu Ile Leu Ile Lys Lys Asp Gly Thr Phe Thr Ile His
        50                  55                  60

Gln Glu Leu Asn Leu Asp Pro Val Asn Trp Gln Ala Pro Gly Cys Lys
65                  70                  75                  80

Asn Lys Val Ser Leu Lys Glu Asn Gln Ile Ile Leu Gln Ser Ile Lys
            85                  90                  95

Thr Lys Pro Asp Glu Glu Ile Thr Val Tyr Leu Asp Thr Val Tyr Cys
            100                 105                 110

Ala Thr Tyr Tyr Asn Cys Val Asp Thr Lys Asn Leu Glu Ile Arg Gly
            115                 120                 125

Tyr Glu Lys His Met Val Asp Leu Ala Trp Glu Lys Pro Glu Leu Ile
            130                 135                 140

Glu Lys Gly Phe Arg Pro Thr Arg Arg Glu Tyr Gln Thr Glu Asn Gly
145                 150                 155                 160

Phe Ile Asp Leu Met Gly Thr Asp Lys Asp Glu Lys Leu Met Ile Leu
                165                 170                 175

Glu Phe Lys Ser Arg Lys Ala Gly Thr Asn Ala Val Lys Gln Leu Lys
            180                 185                 190

Gly Tyr Val Glu Cys Phe Met Asp Asn Lys Glu Phe Val Arg Gly Ile

```
                195                 200                 205
Ile Val Ala Pro Asp Ile Thr Asp Asn Ala Leu Glu Leu Leu Lys Ser
            210                 215                 220

Leu Gln Met Glu Phe Ile Pro Leu Asn Pro Pro Lys Asp Leu Leu Thr
225                 230                 235                 240

Lys Lys Ala Ser Thr Leu Asp Ser Phe
                245
```

<210> SEQ ID NO 42
<211> LENGTH: 249
<212> TYPE: PRT
<213> ORGANISM: Methanobacterium lacus

<400> SEQUENCE: 42

```
Met Lys Phe Leu Ser Glu Glu Asn Pro Asp His Gln Arg Thr Phe Glu
1               5                   10                  15

Ile Ile Asn Glu Gly Leu Ser Lys Lys Ala Val Val Val Val Val Ala
            20                  25                  30

Cys Cys Thr Val Asn Tyr Asp Gly Arg Ala Arg Ser Lys Leu Gly Ala
        35                  40                  45

Gly Asp Arg Met Val Met Ile Lys Ser Asp Gly Ser Phe Met Val His
    50                  55                  60

Gln Asn Ile Asn Leu Glu Pro Val Asn Trp Gln Pro Pro Lys Ser Asn
65                  70                  75                  80

Cys Ser Ala Val Leu Lys Asp Gly Asn Ile Ile Leu Glu Gly Ser Arg
                85                  90                  95

Arg Ser Pro Pro Glu Arg Leu Gln Val Val Ile His Lys Thr Tyr Val
            100                 105                 110

Ala Ser Tyr Tyr Asn Gly Lys Asp Asn Lys Asp Leu Glu Leu Thr Gly
        115                 120                 125

Tyr Glu Glu Asn Met Arg Glu Met Ile Phe Lys Thr Pro Asp Ile Ile
    130                 135                 140

Glu Glu Gly Phe Arg Pro Ser Thr Lys Glu Tyr Pro Thr Ser Thr Gly
145                 150                 155                 160

Phe Ile Asp Val Leu Gly Lys Asp Lys Asn Gly Asn Val Val Val Leu
                165                 170                 175

Glu Leu Lys Ser Arg Arg Ala Gly Ile Asn Ala Val Lys Gln Leu Lys
            180                 185                 190

Arg Tyr Leu Asp Asp Phe Ser Asp His Lys Glu Phe Val Arg Gly Ile
        195                 200                 205

Leu Val Ala Pro Ser Val Thr Asp Ala Ala Glu Leu Leu Glu Gly
    210                 215                 220

Phe Lys Leu Glu Phe Lys Pro Leu Asp Pro Pro Arg Glu Phe Gly Ala
225                 230                 235                 240

Asp Lys Asn Leu Thr Leu Asp Phe Phe
                245
```

<210> SEQ ID NO 43
<211> LENGTH: 249
<212> TYPE: PRT
<213> ORGANISM: Methanobacterium

<400> SEQUENCE: 43

```
Met Leu Ile Glu Ile Lys His Asn Pro Ser Asn Leu Glu Ser Met Glu
1               5                   10                  15

Ile Ile Asn Glu Ala Leu Ser Lys Arg Ala Phe Leu Ile Leu Val Leu
```

```
                    20                  25                  30
Cys Cys Lys Val Asn Tyr Glu Gly Arg Ala Arg Ser Lys Leu Gly Leu
            35                  40                  45
Gly Glu Arg Thr Val Leu Ile Lys Gly Asp Gly Ser Phe Ile Ile His
        50                  55                  60
Gln Asp Arg Asn Leu Glu Pro Ile Asn Trp Gln Pro Pro Lys Thr Lys
65                  70                  75                  80
Leu Ser Val Lys Leu Glu Asn Asp Val Ile Lys Ile Val Gly Met Arg
                85                  90                  95
Arg Lys Pro Lys Glu Gln Leu Glu Leu Ile Ile Ser Thr Val His Leu
            100                 105                 110
Ile Ser Tyr Tyr Phe Gly Ser Asp Thr Lys Asp Ile Glu Leu Ala Gly
        115                 120                 125
Tyr Glu Glu Asp Met Arg His Met Ile Met Asn Asn Pro Asp Leu Ile
    130                 135                 140
Glu Lys Gly Phe Arg Pro Thr Ser Lys Glu Tyr Gln Thr Pro Gln Gly
145                 150                 155                 160
Phe Ile Asp Ile Tyr Gly Lys Asp Ala Asn Gly Lys Ile Val Ile Ile
                165                 170                 175
Glu Leu Lys Ser Arg Lys Ala Gly Ile Asn Ala Val Lys Gln Leu Lys
            180                 185                 190
Arg Tyr Ile Asn Cys Phe Leu Asp Asn Lys Glu Phe Val Arg Gly Ile
        195                 200                 205
Leu Val Ala Pro Ser Ile Thr Asp Asp Ala Arg Glu Leu Leu Glu Asn
    210                 215                 220
Asn Lys Met Glu Tyr Ile Ser Leu Asp Pro Pro Lys Glu Leu Lys Thr
225                 230                 235                 240
Lys Thr Thr Thr Thr Leu Asp Tyr Phe
                245

<210> SEQ ID NO 44
<211> LENGTH: 249
<212> TYPE: PRT
<213> ORGANISM: Methanobacterium

<400> SEQUENCE: 44

Met Leu Leu Lys Ile Glu His Asn Pro Thr Asn Leu Glu Ala Thr Glu
1               5                   10                  15
Leu Ile Asn Glu Ala Ile Ser Lys Arg Ala Phe Met Ile Leu Val Val
            20                  25                  30
Cys Cys Lys Val Asn Tyr Glu Gly Arg Ala Thr Ser Lys Leu Gly Phe
        35                  40                  45
Gly Glu Arg Thr Val Leu Ile Lys Gly Asp Gly Ser Phe Ile Ile His
    50                  55                  60
Gln Asp Arg Asn Leu Glu Pro Ile Asn Trp Gln Pro Pro Arg Thr Lys
65                  70                  75                  80
Ile Gly Val Lys Leu Glu Asp Asp Val Ile Lys Ile Met Gly Lys Arg
                85                  90                  95
Arg Lys Pro Lys Glu Gln Leu Glu Leu Val Ile Arg Asn Val His Leu
            100                 105                 110
Ile Ser Tyr His Leu Gly Ser Asp Thr Lys Asp Ile Glu Leu Ala Gly
        115                 120                 125
Tyr Glu Glu Asp Met Arg Gln Met Ile Met Asp Asn Pro Glu Leu Ile
    130                 135                 140
```

-continued

Glu Lys Gly Phe Arg Pro Thr Ser Lys Glu Tyr Gln Thr Pro Gln Gly
145                 150                 155                 160

Phe Ile Asp Ile Leu Gly Lys Asp Asp Ala Gly Lys Leu Val Val Leu
                165                 170                 175

Glu Leu Lys Ser Arg Lys Ala Gly Val Asn Ala Val Lys Gln Leu Leu
            180                 185                 190

Arg Tyr Val Asp Cys Phe Ser Asp Asn Lys Glu Phe Val Arg Gly Ile
        195                 200                 205

Leu Val Ser Pro Ser Ile Thr Glu Glu Ala Lys Glu Ile Leu Asn Glu
210                 215                 220

Tyr Gln Met Glu His Ile Ser Leu Ser Pro Pro Lys Glu Leu Lys Val
225                 230                 235                 240

Lys Ser Ser Thr Thr Leu Asp Tyr Phe
                245

<210> SEQ ID NO 45
<211> LENGTH: 251
<212> TYPE: PRT
<213> ORGANISM: Palaeococcus pacificus

<400> SEQUENCE: 45

Met Lys Val Lys Ser Lys Glu Asn Pro Ser Val Glu Glu Val Val Glu
1               5                   10                  15

Ile Leu Ser Glu Gly Leu Ser Asn Glu Ala Ile Ile Thr Leu Phe Ala
            20                  25                  30

His Cys Ser Val Phe Tyr Asp Gly Arg Ala Lys Ser Glu Leu Gly Ala
        35                  40                  45

Gly Asp Arg Val Ile Met Ile Lys Pro Asp Gly Thr Phe Leu Ile His
    50                  55                  60

Gln Lys Glu Lys Arg Val Pro Val Asn Trp Gln Pro Pro Gly Ser Ile
65                  70                  75                  80

Val Ser Phe Gln Ile Glu Glu Gly Lys Ile Lys Leu Arg Ser Val Arg
                85                  90                  95

Arg Lys Pro Lys Glu Ile Leu Glu Val Glu Leu Leu Lys Val Tyr Leu
            100                 105                 110

Ile Ser Tyr Phe Gln Ala Glu Asp Tyr Glu Ala Leu Asn Leu Met Gly
        115                 120                 125

Ser Glu Ala Glu Met Ala Asp Leu Ile Leu Gln Asn Pro Ser Ile Ile
    130                 135                 140

Glu Glu Gly Phe Lys Ala Leu Gln Lys Glu Lys Pro Ile Lys His Gly
145                 150                 155                 160

Ile Ile Asp Ile Tyr Gly Val Asp Arg Asp Gly Asn Ile Val Val Leu
                165                 170                 175

Glu Leu Lys Arg Arg Arg Ala Asp Leu His Ala Val Ser Gln Leu Lys
            180                 185                 190

Arg Tyr Val Asp Ala Leu Lys Glu Glu His Gly Ser Val Arg Gly Ile
        195                 200                 205

Leu Val Ala Pro Ser Leu Thr Ser Gly Ala Glu Lys Leu Leu Lys Asp
    210                 215                 220

Leu Gly Leu Glu Phe Lys Lys Leu Asn Pro Pro Lys Arg Glu Lys Ala
225                 230                 235                 240

Arg Lys Gly Lys Gln Lys Thr Leu Asp Met Leu
                245                 250

<210> SEQ ID NO 46

```
<211> LENGTH: 242
<212> TYPE: PRT
<213> ORGANISM: Methanobacterium formicicum

<400> SEQUENCE: 46

Asn Pro Asp Thr Pro Arg Val Leu Glu Ile Ile Asn Glu Gly Leu Ser
1               5                   10                  15

Lys Arg Ala Val Ile Thr Ile Met Ala Cys Cys Arg Val Asp Tyr Asp
            20                  25                  30

Gly Arg Ala Val Ser Arg Leu Gly Leu Gly Asp Arg Ile Ile Leu Ile
        35                  40                  45

Lys Ser Asp Gly Ser Phe Ile Ile His Gln Arg Asn Leu Asp Pro
50                  55                  60

Val Asn Trp Gln Pro Pro Lys Thr Lys Val Thr Ala Asp Ile Tyr Gln
65              70                  75                  80

Gly Met Val Lys Ile Lys Gly Val Arg Arg Asn Pro Ser Glu Ser Leu
                85                  90                  95

Glu Val Lys Ile Leu Gln Thr His Met Ile Ser Tyr Phe Ile Gly Glu
            100                 105                 110

Asp Ser Glu Ser Leu Glu Leu Ala Gly Tyr Glu Ala Asn Met Gly Asp
        115                 120                 125

Leu Ile Phe Lys Asp Pro Glu Val Phe Glu Lys Gly Phe Arg Pro Thr
130                 135                 140

Ser Arg Glu Tyr His Thr Pro Gln Gly Phe Ile Asp Ile Leu Gly Lys
145                 150                 155                 160

Asp Gln Asp Gly Asn Ile Thr Ile Leu Glu Leu Lys Ser Arg Lys Ala
                165                 170                 175

Gly Thr Asn Ala Val Lys Gln Leu Arg Arg Tyr Val Asp Cys Phe Ser
            180                 185                 190

Asp His Lys Glu Lys Val Arg Gly Val Leu Val Ala Pro Ser Ala Thr
        195                 200                 205

Asp Asp Ala Leu Glu Leu Leu Glu Glu Gln Gly Met Glu Phe Lys Ala
    210                 215                 220

Leu Glu Pro Pro Arg Glu Leu Gly Thr Asp Lys Val Val Thr Leu Glu
225                 230                 235                 240

Asn Phe

<210> SEQ ID NO 47
<211> LENGTH: 247
<212> TYPE: PRT
<213> ORGANISM: Pyrococcus kukulkanii

<400> SEQUENCE: 47

Lys Ile Val Val Arg Glu Asn Pro Thr Val Glu Asp Val Lys Glu Leu
1               5                   10                  15

Leu Glu Phe Ala Glu Lys His Asn Gly Met Val Thr Ile Phe Ala Arg
            20                  25                  30

Cys Arg Val Tyr Tyr Glu Gly Arg Ala Lys Ser Glu Leu Gly Glu Gly
        35                  40                  45

Asp Arg Ile Ile Ile Ile Lys Pro Asp Gly Ser Phe Leu Ile His Gln
    50                  55                  60

Asn Lys Lys Arg Glu Pro Val Asn Trp Gln Pro Pro Gly Ser Val Val
65              70                  75                  80

Lys Ile Glu Gly Asn Lys Val Val Ser Ile Arg Arg Lys Pro Arg Glu
                85                  90                  95
```

```
Lys Leu Glu Val Glu Leu Ile Glu Ser Tyr Ala Ile Thr Val Phe Leu
                100                 105                 110

Ala Glu Asp Tyr Glu Glu Leu Ser Leu Thr Gly Ser Glu Ala Glu Met
            115                 120                 125

Ala Lys Leu Ile Phe Glu Lys Pro Glu Val Ile Glu Glu Gly Phe Lys
        130                 135                 140

Pro Met Phe Lys Glu Lys Pro Ile Lys His Gly Ile Val Asp Ile Leu
145                 150                 155                 160

Gly Val Asp Arg Glu Gly Asn Val Val Leu Glu Leu Lys Arg Arg
                165                 170                 175

Arg Ala Asp Leu His Ala Val Ser Gln Leu Lys Arg Tyr Val Asp Ser
            180                 185                 190

Leu Lys Glu Glu Tyr Gly Asp Lys Val Arg Gly Ile Leu Val Ala Pro
        195                 200                 205

Ser Leu Thr Glu Gly Ala Arg Lys Leu Leu Glu Lys Glu Gly Leu Glu
210                 215                 220

Phe Arg Lys Leu Glu Pro Pro Lys Arg Glu Ser Arg Lys Lys Ser Lys
225                 230                 235                 240

Gln Lys Thr Leu Asp Phe Phe
                245

<210> SEQ ID NO 48
<211> LENGTH: 247
<212> TYPE: PRT
<213> ORGANISM: Thermococcus guaymasensis

<400> SEQUENCE: 48

Lys Val Glu Leu Arg Glu Asn Pro Ser Pro Glu Glu Ile Lys Leu Leu
1               5                   10                  15

Val Asp Ser Ala Val Ser Ser Glu Gly Ile Leu Thr Ile Phe Ala Arg
            20                  25                  30

Cys Arg Val His Tyr Asp Gly Arg Ala Lys Ser Glu Leu Gly Pro Gly
        35                  40                  45

Asp Arg Val Ile Ile Val Lys Pro Asp Gly Ser Phe Leu Ile His Gln
    50                  55                  60

Lys Glu Lys Arg Glu Pro Val Asn Trp Gln Pro Pro Gly Ser Val Val
65                  70                  75                  80

Arg Leu Glu Leu Arg Glu Lys Pro Val Leu Val Ser Val Arg Arg Lys
                85                  90                  95

Pro Arg Glu Thr Leu Glu Val Glu Leu Glu Glu Val Tyr Leu Ile Thr
            100                 105                 110

Val Phe His Ala Glu Asp Tyr Glu Glu Leu Ala Leu Thr Gly Ser Glu
        115                 120                 125

Ala Glu Met Ala Glu Leu Ile Phe Glu Asn Pro Glu Val Ile Glu Phe
    130                 135                 140

Gly Phe Lys Pro Leu Tyr Arg Glu Lys Pro Ile Lys His Gly Ile Val
145                 150                 155                 160

Asp Val Leu Gly Val Asp Arg Glu Gly Asn Ile Val Val Leu Glu Leu
                165                 170                 175

Lys Arg Arg Arg Ala Asp Leu His Ala Val Ser Gln Leu Lys Arg Tyr
            180                 185                 190

Val Glu Thr Leu Arg Glu Glu His Glu Asn Val Arg Gly Ile Leu Val
        195                 200                 205

Ala Pro Ser Leu Thr Ser Gly Ala Lys Lys Leu Leu Glu Lys Glu Gly
    210                 215                 220
```

Leu Glu Phe Arg Lys Leu Glu Pro Pro Lys Arg Asp Arg Lys Ser Arg
225                 230                 235                 240

Gly Lys Gln Leu Lys Leu Phe
                245

<210> SEQ ID NO 49
<211> LENGTH: 247
<212> TYPE: PRT
<213> ORGANISM: Thermococcus eurythermalis

<400> SEQUENCE: 49

Lys Val Glu Leu Arg Glu Asn Pro Ser Pro Glu Glu Ile Lys Leu Leu
1               5                   10                  15

Val Asp Ser Ala Val Ser Ser Glu Gly Val Leu Thr Ile Phe Ala Arg
            20                  25                  30

Cys Arg Val His Tyr Asp Gly Arg Ala Lys Ser Glu Leu Gly Pro Gly
        35                  40                  45

Asp Arg Val Ile Ile Val Lys Pro Asp Gly Ser Phe Leu Ile His Gln
    50                  55                  60

Lys Glu Lys Arg Glu Pro Val Asn Trp Gln Pro Pro Gly Ser Val Val
65                  70                  75                  80

Arg Leu Glu Leu Arg Glu Lys Pro Val Leu Val Ser Val Arg Arg Lys
                85                  90                  95

Pro Arg Glu Thr Leu Glu Val Glu Leu Glu Val Tyr Leu Ile Thr
            100                 105                 110

Val Phe His Ala Glu Asp Tyr Glu Glu Leu Ala Leu Thr Gly Ser Glu
        115                 120                 125

Ala Glu Met Ala Glu Leu Ile Phe Glu Asn Pro Glu Val Ile Glu Pro
    130                 135                 140

Gly Phe Lys Pro Leu Tyr Arg Glu Lys Pro Ile Lys His Gly Ile Val
145                 150                 155                 160

Asp Val Leu Gly Val Asp Arg Asp Gly Asn Leu Val Val Leu Glu Leu
                165                 170                 175

Lys Arg Arg Arg Ala Asp Leu His Ala Val Ser Gln Leu Lys Arg Tyr
            180                 185                 190

Val Glu Thr Leu Arg Glu Glu His Glu Asn Val Arg Gly Ile Leu Val
        195                 200                 205

Ala Pro Ser Leu Thr Ser Gly Ala Lys Lys Leu Leu Glu Lys Glu Gly
    210                 215                 220

Leu Glu Phe Arg Lys Leu Glu Pro Pro Lys Arg Asp Arg Lys Ser Arg
225                 230                 235                 240

Gly Lys Gln Leu Lys Leu Phe
                245

<210> SEQ ID NO 50
<211> LENGTH: 247
<212> TYPE: PRT
<213> ORGANISM: Thermococcus nautili

<400> SEQUENCE: 50

Lys Val Glu Leu Arg Glu Asn Pro Ser Pro Glu Glu Ile Lys Leu Leu
1               5                   10                  15

Val Asp Ser Ala Val Ser Ser Glu Gly Val Leu Thr Ile Phe Ala Arg
            20                  25                  30

Cys Arg Val His Tyr Asp Gly Arg Ala Lys Ser Glu Leu Gly Pro Gly
        35                  40                  45

Asp Arg Val Ile Ile Val Lys Pro Asp Gly Ser Phe Leu Ile His Gln
                50                  55                  60

Lys Glu Lys Arg Glu Pro Val Asn Trp Gln Pro Pro Gly Ser Val Val
 65                  70                  75                  80

Arg Leu Glu Leu Arg Glu Lys Pro Val Leu Val Ser Val Arg Arg Lys
                    85                  90                  95

Pro Arg Glu Thr Leu Glu Val Glu Leu Glu Val Tyr Leu Ile Thr
                100                 105                 110

Val Phe His Ala Glu Asp Tyr Glu Glu Leu Ala Leu Thr Gly Ser Glu
                115                 120                 125

Ala Glu Met Ala Glu Leu Ile Phe Glu Asn Pro Glu Val Ile Glu Pro
            130                 135                 140

Gly Phe Lys Pro Leu Tyr Arg Glu Lys Pro Ile Lys His Gly Ile Val
145                 150                 155                 160

Asp Val Leu Gly Val Asp Lys Asp Gly Asn Leu Val Val Leu Glu Leu
                165                 170                 175

Lys Arg Arg Arg Ala Asp Leu His Ala Val Ser Gln Leu Lys Arg Tyr
                180                 185                 190

Val Glu Thr Leu Arg Glu Glu His Glu Asn Val Arg Gly Ile Leu Val
            195                 200                 205

Ala Pro Ser Leu Thr Ser Gly Ala Lys Lys Leu Leu Glu Lys Glu Gly
            210                 215                 220

Leu Glu Phe Arg Lys Leu Glu Pro Pro Lys Arg Gly Arg Lys Ser Arg
225                 230                 235                 240

Gly Lys Gln Leu Lys Leu Phe
                245

<210> SEQ ID NO 51
<211> LENGTH: 247
<212> TYPE: PRT
<213> ORGANISM: Thermococcus gammatolerans

<400> SEQUENCE: 51

Lys Val Glu Leu Arg Glu Asn Pro Ser Pro Glu Glu Ile Lys Leu Leu
 1               5                  10                  15

Val Asp Leu Ala Ile Ser Ser Glu Gly Val Leu Thr Ile Phe Ala Arg
                20                  25                  30

Cys Arg Val His Tyr Asp Gly Arg Ala Lys Ser Glu Leu Gly Pro Gly
                35                  40                  45

Asp Arg Val Ile Ile Val Lys Pro Asp Gly Ser Phe Leu Ile His Gln
                50                  55                  60

Lys Glu Lys Arg Glu Pro Val Asn Trp Gln Pro Pro Gly Ser Val Val
 65                  70                  75                  80

Arg Leu Glu Leu Arg Glu Lys Pro Val Leu Ile Ser Val Arg Arg Lys
                    85                  90                  95

Pro Arg Glu Thr Leu Glu Val Glu Leu Asp Glu Val Tyr Leu Ile Thr
                100                 105                 110

Val Phe His Ala Glu Asp Tyr Glu Glu Leu Ala Leu Thr Gly Ser Glu
                115                 120                 125

Ala Glu Met Ala Glu Leu Ile Phe Glu Asn Pro Glu Val Ile Glu Leu
            130                 135                 140

Gly Phe Lys Pro Leu Tyr Arg Glu Lys Pro Ile Arg His Gly Ile Val
145                 150                 155                 160

Asp Val Leu Gly Val Asp Arg Asp Gly Asn Leu Val Val Leu Glu Leu 165                 170                 175
Lys Arg Arg Arg Ala Asp Leu His Ala Val Ser Gln Leu Lys Arg Tyr
            180                 185                 190

Val Glu Thr Leu Arg Glu Glu His Glu Asn Val Arg Gly Ile Leu Val
        195                 200                 205

Ala Pro Ser Leu Thr Ser Gly Ala Lys Lys Leu Leu Glu Lys Glu Gly
    210                 215                 220

Leu Glu Phe Arg Lys Leu Glu Pro Pro Lys Arg Asp Gly Lys Ser Arg
225                 230                 235                 240

Gly Arg Gln Leu Arg Leu Phe
                245

<210> SEQ ID NO 52
<211> LENGTH: 247
<212> TYPE: PRT
<213> ORGANISM: Thermococcus

<400> SEQUENCE: 52

Lys Val Glu Leu Arg Glu Asn Pro Ser Pro Glu Glu Ile Lys Leu Leu
1               5                   10                  15

Val Asp Ser Ala Val Ser Ser Glu Gly Val Leu Thr Ile Phe Ala Arg
            20                  25                  30

Cys Arg Val His Tyr Asp Gly Arg Ala Lys Ser Glu Leu Gly Pro Gly
        35                  40                  45

Asp Arg Val Ile Ile Val Lys Pro Asp Gly Ser Phe Leu Ile His Gln
    50                  55                  60

Lys Glu Lys Arg Glu Pro Val Asn Trp Gln Pro Gly Ser Val Val
65                  70                  75                  80

Arg Leu Glu Leu Arg Gly Lys Pro Val Leu Val Ser Val Arg Arg Lys
                85                  90                  95

Pro Arg Glu Thr Leu Glu Val Glu Leu Glu Glu Val Tyr Leu Ile Thr
            100                 105                 110

Val Phe His Ala Glu Asp Tyr Glu Glu Leu Ala Leu Thr Gly Ser Glu
        115                 120                 125

Ala Glu Met Ala Glu Leu Ile Phe Glu Asn Pro Glu Val Ile Glu Pro
    130                 135                 140

Gly Phe Lys Pro Leu Tyr Arg Glu Lys Pro Ile Lys His Gly Ile Val
145                 150                 155                 160

Asp Val Leu Gly Val Asp Lys Asp Gly Asn Leu Val Val Leu Glu Leu
                165                 170                 175

Lys Arg Arg Arg Ala Asp Leu His Ala Val Ser Gln Leu Lys Arg Tyr
            180                 185                 190

Val Glu Thr Leu Arg Glu Lys His Glu Asn Val Arg Gly Ile Leu Val
        195                 200                 205

Ala Pro Ser Leu Thr Ser Gly Ala Arg Lys Leu Leu Glu Lys Glu Gly
    210                 215                 220

Leu Glu Phe Arg Lys Leu Glu Pro Pro Lys Arg Gly Arg Lys Ser Lys
225                 230                 235                 240

Gly Arg Gln Leu Lys Leu Phe
                245

<210> SEQ ID NO 53
<211> LENGTH: 252
<212> TYPE: PRT
<213> ORGANISM: Methanotorris igneus

<400> SEQUENCE: 53

Lys Val Asn Tyr Leu Val Asn Pro Lys Ala Glu Asp Ile Val Glu Leu
1               5                   10                  15

Leu Ala Ser Gly Ile Val Asn Asp Ser Ile Leu Val Phe Phe Ala Phe
            20                  25                  30

Cys Arg Val Arg Tyr Asp Gly Arg Ala Lys Ser Glu Leu Glu Pro Gly
                35                  40                  45

Asp Arg Ile Ile Ile Ile Lys Pro Asp Gly Ser Phe Leu Val His Lys
        50                  55                  60

Asn Thr Lys Arg Glu Pro Val Asn Trp Gln Pro Pro Gly Ser Val Val
65                  70                  75                  80

Ser Trp Glu Val His Asp Gly Lys Leu Val Leu Lys Ser Val Arg Lys
                85                  90                  95

Lys Pro Arg Glu Ile Leu Gln Val Glu Leu Ile Lys Val Tyr His Ala
                100                 105                 110

Cys Ser Phe Gln Cys Glu Asp Tyr Glu Glu Leu Ser Leu Thr Gly Ser
            115                 120                 125

Glu Ala Glu Met Ala Glu Leu Ile Phe Glu Asn Pro Ser Leu Ile Glu
130                 135                 140

Asp Gly Phe Lys Pro Leu Phe Lys Glu Lys Gln Ile Asn His Gly Ile
145                 150                 155                 160

Ile Asp Ile Leu Gly Lys Asp Lys Ser Gly Arg Trp Val Val Ile Glu
                165                 170                 175

Leu Lys Arg Arg Arg Ala Asp Leu Gln Ala Val Ser Gln Leu Lys Arg
            180                 185                 190

Tyr Val Glu Cys Leu Lys Tyr Glu Tyr Gly Glu Gly Asn Ile Arg Gly
        195                 200                 205

Ile Leu Val Ala Pro Ser Leu Thr Ser Gly Ala Lys Lys Leu Leu Glu
        210                 215                 220

Glu Glu Asn Leu Glu Phe Arg Glu Leu Lys Pro Pro Lys Lys Glu Arg
225                 230                 235                 240

Leu Lys Glu Asn Lys Gln Thr Thr Leu Asp Phe Tyr
                245                 250

<210> SEQ ID NO 54
<211> LENGTH: 249
<212> TYPE: PRT
<213> ORGANISM: Thermococcus barophilus

<400> SEQUENCE: 54

Met Lys Val Glu Ala Lys Val Glu Pro Ser His Glu Glu Ile Ile Glu
1               5                   10                  15

Ile Leu Asp Lys Ala Leu Ser Val Glu Ala Ile Ile Thr Leu Phe Ala
            20                  25                  30

Tyr Cys Arg Val Phe Tyr Glu Gly Arg Ala Lys Ser Glu Leu Gly Pro
                35                  40                  45

Gly Asp Arg Val Ile Ile Lys Pro Asp Gly Ser Phe Leu Ile His
        50                  55                  60

Gln Lys Asn Lys Arg Glu Pro Val Asn Trp Gln Pro Pro Gly Ser Val
65                  70                  75                  80

Val Ser Ile Val Leu Glu Asp Gly Arg Ile Met Leu Arg Ser Val Arg
                85                  90                  95

Arg Lys Pro Lys Glu Thr Leu Glu Val Glu Leu Ile Lys Thr Tyr Leu
                100                 105                 110

```
Val Ser Tyr Phe Gln Ala Glu Asp Tyr Glu Leu Thr Leu Thr Gly
        115                 120                 125

Ser Glu Ala Glu Met Ala Asp Leu Ile Phe Glu Asn Pro Ser Leu Ile
    130                 135                 140

Glu Glu Gly Phe Lys Pro Leu Phe Lys Glu Lys Pro Ile Lys His Gly
145                 150                 155                 160

Ile Val Asp Val Leu Gly Lys Asp Lys His Gly Asn Leu Val Val Leu
                165                 170                 175

Glu Leu Lys Arg Arg Arg Ala Asp Leu His Ala Val Ser Gln Leu Lys
                180                 185                 190

Arg Tyr Val Asp Ser Leu Arg Glu Glu His Lys Asn Val Arg Gly Ile
        195                 200                 205

Leu Val Ala Pro Ser Leu Thr Ala Gly Ala Lys Lys Leu Leu Glu Lys
    210                 215                 220

Glu Gly Leu Glu Phe Lys Lys Leu Asn Pro Pro Lys Arg Glu Lys Arg
225                 230                 235                 240

Lys Lys Gly Lys Gln Lys Thr Leu Asp
                245
```

<210> SEQ ID NO 55
<211> LENGTH: 249
<212> TYPE: PRT
<213> ORGANISM: Thermococcus barophilus

<400> SEQUENCE: 55

```
Met Lys Val Glu Ala Lys Val Gly Pro Ser His Glu Glu Ile Val Glu
1               5                   10                  15

Ile Leu Asn Lys Ala Leu Ser Val Glu Ala Ile Ile Thr Leu Phe Ala
                20                  25                  30

Tyr Cys Arg Val Phe Tyr Glu Gly Arg Ala Lys Ser Glu Leu Gly Pro
            35                  40                  45

Gly Asp Arg Val Ile Ile Ile Lys Pro Asp Gly Ser Phe Leu Ile His
    50                  55                  60

Gln Lys Asn Lys Arg Glu Pro Val Asn Trp Gln Pro Pro Gly Ser Val
65                  70                  75                  80

Val Ser Ile Val Leu Gly Asp Gly Arg Ile Met Leu Arg Ser Val Arg
                85                  90                  95

Arg Lys Pro Lys Glu Thr Leu Glu Val Glu Leu Ile Lys Thr Tyr Leu
            100                 105                 110

Val Ser Tyr Phe Gln Ala Glu Asp Tyr Glu Leu Thr Leu Thr Gly
        115                 120                 125

Ser Glu Ala Glu Met Ala Asp Leu Ile Phe Glu Asn Pro Ser Leu Ile
    130                 135                 140

Glu Glu Gly Phe Lys Pro Leu Phe Lys Glu Lys Pro Ile Lys His Gly
145                 150                 155                 160

Ile Val Asp Val Leu Gly Lys Asp Lys His Gly Asn Leu Val Val Leu
                165                 170                 175

Glu Leu Lys Arg Arg Arg Ala Asp Leu His Ala Val Ser Gln Leu Lys
                180                 185                 190

Arg Tyr Val Asp Ser Leu Arg Glu Glu His Lys Asn Val Arg Gly Ile
        195                 200                 205

Leu Val Ala Pro Ser Leu Thr Ala Gly Ala Lys Lys Leu Leu Glu Lys
    210                 215                 220

Glu Gly Leu Glu Phe Lys Lys Leu Asn Pro Pro Lys Arg Glu Lys Arg
225                 230                 235                 240
```

```
Lys Lys Gly Lys Gln Lys Thr Leu Asp
                245

<210> SEQ ID NO 56
<211> LENGTH: 242
<212> TYPE: PRT
<213> ORGANISM: Methanobacterium

<400> SEQUENCE: 56

Asn Pro Asp Thr Gln Arg Val Leu Asp Ile Ile Asn Glu Gly Leu Ser
1               5                   10                  15

Lys Arg Ala Val Ile Thr Ile Met Ala Ser Cys Arg Val Tyr Tyr Asp
            20                  25                  30

Gly Arg Ala Val Ser Arg Leu Glu Leu Gly Asp Arg Ile Ile Met Ile
        35                  40                  45

Lys Ser Asp Gly Ser Phe Ile Ile His Gln Asp Arg Asn Leu Glu Pro
    50                  55                  60

Val Asn Trp Gln Pro Pro Lys Thr Lys Val Thr Val Asp Thr His Gln
65                  70                  75                  80

Gly Met Val Lys Ile Arg Gly Val Arg Arg Ser Pro Ser Glu Ser Leu
                85                  90                  95

Glu Val Glu Ile Leu Gln Thr His Leu Val Ser Tyr Phe Ile Gly Glu
            100                 105                 110

Asp Val Glu Ser Leu Glu Leu Ala Gly Tyr Glu Ala Asn Met Gly Asp
        115                 120                 125

Leu Ile Phe Lys Asp Pro Glu Val Ile Glu Lys Gly Phe Arg Pro Thr
    130                 135                 140

Ser Arg Glu Tyr His Thr Pro Gln Gly Phe Ile Asp Val Leu Gly Lys
145                 150                 155                 160

Asp Gln Asn Gly Asn Ile Thr Ile Leu Glu Leu Lys Ser Arg Lys Ala
                165                 170                 175

Gly Val Asn Ala Val Lys Gln Leu Arg Arg Tyr Val Asp Cys Phe Ser
            180                 185                 190

Asp His Lys Asp Thr Val Arg Gly Val Leu Val Ala Pro Ser Ile Thr
        195                 200                 205

Asp Asp Ala Arg Glu Leu Leu Glu Glu Gln Lys Met Glu Phe Lys Glu
    210                 215                 220

Leu Glu Pro Pro Arg Glu Leu Gly Thr Asp Lys Val Val Thr Leu Glu
225                 230                 235                 240

Lys Phe

<210> SEQ ID NO 57
<211> LENGTH: 249
<212> TYPE: PRT
<213> ORGANISM: Pyrococcus yayanosii

<400> SEQUENCE: 57

Lys Ala Glu Val Arg Met Glu Pro Thr Pro Lys Glu Leu Ala Glu Leu
1               5                   10                  15

Phe Asp Leu Ala Arg Lys Leu Glu Gly Met Leu Ile Ile Phe Ala Arg
            20                  25                  30

Cys Arg Val His Tyr Glu Gly Arg Ala Lys Ser Glu Leu Gly Glu Gly
        35                  40                  45

Asp Arg Ile Ile Met Ile Lys Pro Asp Gly Ser Phe Leu Ile His Gln
    50                  55                  60
```

Lys Lys Lys Arg Glu Pro Val Asn Trp Gln Pro Gly Ser Lys Val
65                  70                  75                  80

Arg Leu Glu Leu Arg Asn Val Pro Thr Ile Val Ser Val Arg Arg Lys
            85                  90                  95

Pro Arg Glu Ile Leu Glu Val Glu Leu Leu Glu Thr Tyr Met Val Ser
            100                 105                 110

Ala Phe Phe Ala Glu Asp Tyr Glu Ala Leu Lys Leu Ser Gly Ser Glu
            115                 120                 125

Ala Glu Met Ala Ala Leu Ile Phe Ser Asn Pro Asp Val Ile Glu Pro
        130                 135                 140

Gly Phe Lys Pro Leu Phe Arg Glu Lys Pro Val Arg His Gly Ile Val
145                 150                 155                 160

Asp Val Leu Gly Val Asp Lys Glu Gly Asn Leu Val Val Leu Glu Leu
                165                 170                 175

Lys Arg Arg Lys Ala Asp Leu His Ala Val Ser Gln Leu Lys Arg Tyr
                180                 185                 190

Val Glu Ala Leu Arg Glu Asn Pro Gly Lys Ile Val Arg Gly Ile
            195                 200                 205

Leu Val Ala Pro Ser Ile Thr Ala Gly Ala Gln Arg Leu Leu Glu Lys
210                 215                 220

Glu Gly Leu Glu Phe Arg Arg Met Glu Pro Pro Lys Arg Lys Glu Lys
225                 230                 235                 240

Arg Lys Ser Arg Gln Lys Thr Leu Asp
                245

<210> SEQ ID NO 58
<211> LENGTH: 248
<212> TYPE: PRT
<213> ORGANISM: Thermococcus litoralis

<400> SEQUENCE: 58

Met Lys Val Glu Ala Lys Leu Asn Pro Thr Tyr Glu Glu Ile Val Asp
1               5                   10                  15

Ile Phe Asn Arg Ala Leu Ser Lys Glu Ala Ile Val Asn Ile Phe Ala
            20                  25                  30

His Cys Arg Val Phe Tyr Asp Gly Arg Ala Lys Ser Glu Leu Gly Pro
        35                  40                  45

Gly Asp Arg Val Ile Leu Ile Lys Pro Asp Gly Ser Phe Leu Ile His
    50                  55                  60

Gln Lys Glu Lys Arg Glu Pro Val Asn Trp Gln Pro Pro Gly Ser Ser
65                  70                  75                  80

Val Gly Leu Glu Val Lys Glu Asp Lys Ile Phe Leu Arg Ser Ile Arg
            85                  90                  95

Arg Lys Pro Arg Glu Ile Leu Glu Val Glu Leu Leu Asn Val Tyr Leu
            100                 105                 110

Ile Ser Tyr Phe Gln Ala Glu Asp Tyr Glu Glu Leu Ala Leu Thr Gly
        115                 120                 125

Ser Glu Ala Glu Met Ala Asp Leu Ile Phe Glu Asn Pro Ser Leu Ile
    130                 135                 140

Glu Asp Gly Phe Lys Pro Leu Phe Lys Glu Lys Pro Ile Lys His Gly
145                 150                 155                 160

Ile Val Asp Val Leu Gly Val Asp Lys Glu Gly Asn Ile Val Ile Leu
                165                 170                 175

Glu Leu Lys Arg Arg Arg Ala Asp Leu His Ala Val Ser Gln Leu Lys
                180                 185                 190

```
Arg Tyr Val Glu Ala Met Arg Glu Glu His Glu Lys Val Arg Gly Ile
            195                 200                 205

Leu Val Ala Pro Ser Leu Thr Ser Gly Ala Lys Lys Leu Leu Glu Lys
        210                 215                 220

Glu Gly Leu Glu Phe Arg Lys Leu Thr Pro Pro Lys Arg Gly Lys Ser
225                 230                 235                 240

Lys Arg Gly Arg Gln Lys Thr Leu
                245

<210> SEQ ID NO 59
<211> LENGTH: 248
<212> TYPE: PRT
<213> ORGANISM: Thermococcus

<400> SEQUENCE: 59

Met Lys Val Glu Ala Lys Leu Asn Pro Thr Tyr Glu Glu Ile Val Asp
1               5                   10                  15

Ile Phe Asn Arg Ala Leu Ser Lys Glu Ala Ile Val Asn Ile Phe Ala
            20                  25                  30

His Cys Arg Val Phe Tyr Asp Gly Arg Ala Lys Ser Glu Leu Gly Pro
        35                  40                  45

Gly Asp Arg Val Ile Leu Ile Lys Pro Asp Gly Ser Phe Leu Ile His
    50                  55                  60

Gln Lys Glu Lys Arg Glu Pro Val Asn Trp Gln Pro Gly Ser Ser
65                  70                  75                  80

Val Gly Leu Glu Val Lys Glu Gly Arg Ile Phe Leu Arg Ser Ile Arg
                85                  90                  95

Arg Lys Pro Arg Glu Ile Leu Glu Val Glu Leu Leu His Val Tyr Leu
            100                 105                 110

Ile Ser Tyr Phe Gln Ala Glu Asp Tyr Glu Glu Leu Ala Leu Thr Gly
        115                 120                 125

Ser Glu Ala Glu Met Ala Asp Leu Ile Phe Glu Asn Pro Ser Val Ile
    130                 135                 140

Glu Asp Gly Phe Lys Pro Leu Phe Lys Glu Lys Pro Ile Lys His Gly
145                 150                 155                 160

Ile Val Asp Val Leu Gly Val Asp Lys Glu Gly Asn Ile Val Val Leu
                165                 170                 175

Glu Leu Lys Arg Arg Arg Ala Asp Leu His Ala Val Ser Gln Leu Lys
            180                 185                 190

Arg Tyr Val Glu Ala Met Lys Glu Glu His Glu Lys Val Arg Gly Ile
        195                 200                 205

Leu Val Ala Pro Ser Leu Thr Ser Gly Ala Lys Lys Leu Leu Glu Lys
    210                 215                 220

Glu Gly Leu Glu Phe Arg Arg Leu Thr Pro Pro Lys Arg Gly Lys Ser
225                 230                 235                 240

Lys Arg Gly Arg Gln Lys Thr Leu
                245

<210> SEQ ID NO 60
<211> LENGTH: 243
<212> TYPE: PRT
<213> ORGANISM: Pyrococcus horikoshii

<400> SEQUENCE: 60

Glu Asn Pro Thr Val Glu Glu Val Lys Glu Leu Leu Asp Ile Ala Glu
1               5                   10                  15
```

```
Lys His Gly Gly Val Val Thr Ile Phe Ala Arg Cys Arg Val Tyr Tyr
            20                  25                  30

Glu Gly Arg Ala Lys Ser Glu Leu Gly Glu Gly Asp Arg Ile Val Ile
        35                  40                  45

Ile Lys Pro Asp Gly Ser Phe Leu Ile His Gln Asn Lys Lys Arg Glu
50                  55                  60

Pro Val Asn Trp Gln Pro Gly Ser Lys Val Ser Met Arg Glu Asn
65                  70                  75                  80

Ser Ile Ile Ser Ile Arg Arg Lys Pro His Glu Arg Leu Glu Val Glu
                85                  90                  95

Leu Met Glu Val Tyr Ala Val Thr Val Phe Leu Ala Glu Asp Tyr Glu
            100                 105                 110

Glu Leu Ala Leu Thr Gly Ser Glu Ala Glu Met Ala Lys Leu Ile Phe
        115                 120                 125

Glu Asn Pro Asn Val Ile Glu Glu Gly Phe Lys Pro Met Phe Arg Glu
130                 135                 140

Lys Gln Ile Lys His Gly Ile Val Asp Ile Met Gly Leu Asp Lys Asp
145                 150                 155                 160

Gly Asn Ile Val Val Leu Glu Leu Lys Arg Arg Lys Ala Asp Leu His
                165                 170                 175

Ala Val Ser Gln Leu Lys Arg Tyr Val Asp Ser Leu Lys Glu Glu Tyr
            180                 185                 190

Gly Glu Lys Val Arg Gly Ile Leu Val Ala Pro Ser Leu Thr Glu Gly
        195                 200                 205

Ala Lys Lys Leu Leu Glu Lys Glu Gly Leu Glu Phe Arg Lys Leu Glu
210                 215                 220

Pro Pro Lys Asn Asn Asp Asn Lys Arg Glu Val Lys Gln Lys Thr Leu
225                 230                 235                 240

Asp Phe Phe

<210> SEQ ID NO 61
<211> LENGTH: 247
<212> TYPE: PRT
<213> ORGANISM: Thermococcus thioreducens

<400> SEQUENCE: 61

Lys Val Glu Ala Val Gln Asn Pro Ser Arg Asp Glu Leu Met Arg Met
1               5                   10                  15

Val Asp Ser Ala Leu Ser Ala Glu Ala Met Leu Thr Ile Phe Ala Arg
            20                  25                  30

Cys Lys Val His Tyr Asp Gly Arg Ala Lys Ser Glu Leu Gly Ser Gly
        35                  40                  45

Asp Arg Val Ile Ile Lys Pro Asp Gly Ala Phe Leu Ile His Gln
50                  55                  60

Ser Arg Lys Arg Glu Pro Val Asn Trp Gln Pro Gly Ser Phe Val
65                  70                  75                  80

Met Met Glu Glu Arg Asp Gly Ile Leu Val Leu Arg Ser Val Arg Arg
                85                  90                  95

Lys Pro Lys Glu Ile Leu Glu Val Glu Leu Glu Val Tyr Leu Ile
            100                 105                 110

Ser Leu Phe Lys Ala Glu Asp Tyr Glu Glu Leu Ala Leu Thr Gly Ser
        115                 120                 125

Glu Ala Glu Met Ala Glu Met Val Phe Arg Asn Pro Glu Leu Ile Glu
130                 135                 140
```

```
Pro Gly Phe Lys Pro Leu Phe Arg Glu Lys Gln Ile Gly His Gly Ile
145                 150                 155                 160

Val Asp Ile Leu Gly Arg Asp Arg Asp Gly Asn Leu Val Val Leu Glu
                165                 170                 175

Leu Lys Arg Arg Lys Ala Asp Leu His Ala Val Ser Gln Leu Lys Arg
            180                 185                 190

Tyr Val Glu Ala Leu Lys Arg Glu His Glu Thr Val Arg Gly Ile Leu
                195                 200                 205

Val Ala Pro Ser Leu Thr Ala Gly Ala Lys Lys Leu Leu Glu Lys Glu
        210                 215                 220

Gly Leu Glu Phe Arg Arg Val Gln Pro Pro Lys Arg Glu Lys Phe Gly
225                 230                 235                 240

Arg Gly Arg Gln Lys Thr Leu
                245
```

<210> SEQ ID NO 62
<211> LENGTH: 244
<212> TYPE: PRT
<213> ORGANISM: Thermococcus chitonophagus

<400> SEQUENCE: 62

```
Val Arg Glu Lys Pro Thr Val Glu Asp Val Lys Glu Leu Leu Glu Phe
1               5                   10                  15

Ala Glu Lys His Asn Gly Met Val Thr Ile Phe Ala Arg Cys Arg Val
                20                  25                  30

Tyr Tyr Glu Gly Arg Ala Lys Ser Glu Leu Gly Glu Gly Asp Arg Ile
            35                  40                  45

Ile Ile Ile Lys Pro Asp Gly Ser Phe Leu Ile His Gln Asn Lys Lys
        50                  55                  60

Arg Glu Pro Val Asn Trp Gln Pro Pro Gly Ser Val Val Arg Val Glu
65                  70                  75                  80

Gly Asn Lys Val Ile Ser Ile Arg Arg Lys Pro Arg Glu Lys Leu Glu
                85                  90                  95

Val Glu Leu Ile Glu Ser Tyr Ala Ile Thr Val Phe Leu Ala Glu Asp
            100                 105                 110

Tyr Glu Glu Leu Ser Leu Thr Gly Ser Glu Ala Glu Met Ala Lys Leu
        115                 120                 125

Ile Phe Glu Lys Pro Glu Val Ile Glu Glu Gly Phe Lys Pro Met Phe
130                 135                 140

Lys Glu Lys Pro Ile Lys His Gly Ile Val Asp Ile Leu Gly Ile Asp
145                 150                 155                 160

Arg Glu Gly Asn Val Val Val Leu Glu Leu Lys Arg Arg Ala Asp
                165                 170                 175

Leu His Ala Val Ser Gln Leu Lys Arg Tyr Val Asp Ala Leu Lys Glu
        180                 185                 190

Glu Tyr Gly Glu Arg Val Arg Gly Ile Leu Val Ala Pro Ser Leu Thr
    195                 200                 205

Glu Gly Ala Arg Lys Leu Leu Glu Lys Glu Gly Leu Glu Phe Lys Lys
    210                 215                 220

Leu Glu Pro Pro Lys Arg Glu Ser Arg Lys Lys Ser Lys Gln Arg Thr
225                 230                 235                 240

Leu Asp Phe Phe
```

<210> SEQ ID NO 63

```
<211> LENGTH: 245
<212> TYPE: PRT
<213> ORGANISM: Pyrococcus

<400> SEQUENCE: 63

Ile Lys Glu Lys Pro Thr Ala Asp Glu Ile Lys Glu Leu Leu Asp Ile
1               5                   10                  15

Ala Glu Lys Tyr Gly Gly Val Ile Thr Ile Phe Ala Lys Cys Lys Val
                20                  25                  30

Tyr Tyr Glu Gly Arg Ala Lys Ser Glu Leu Gly Glu Gly Asp Arg Ile
            35                  40                  45

Ile Ile Ile Lys Pro Asp Gly Ser Phe Leu Ile His Gln Asn Lys Lys
50                  55                  60

Arg Glu Pro Val Asn Trp Gln Pro Pro Gly Ser Ser Val Arg Ile Glu
65                  70                  75                  80

Gly Asn Thr Ile Ile Ser Ile Arg Arg Lys Pro Arg Glu Lys Leu Glu
                85                  90                  95

Val Glu Val Leu Glu Ala Tyr Ser Gly Ile Val Phe Phe Ala Glu Asp
            100                 105                 110

Tyr Glu Glu Leu Ala Leu Thr Gly Ser Glu Ala Glu Met Ala Glu Leu
        115                 120                 125

Ile Phe Gln Asn Pro Asp Ile Ile Glu Lys Gly Phe Lys Pro Leu Phe
130                 135                 140

Arg Glu Lys Pro Ile Lys His Gly Ile Val Asp Ile Leu Gly Val Asp
145                 150                 155                 160

Lys Glu Gly Asn Ile Val Val Leu Glu Leu Lys Arg Arg Arg Ala Asp
                165                 170                 175

Leu His Ala Val Ser Gln Leu Lys Arg Tyr Val Glu Ser Leu Lys Glu
            180                 185                 190

Glu Tyr Lys Arg Lys Val Arg Gly Ile Leu Val Ala Pro Ser Leu Thr
        195                 200                 205

Glu Gly Ala Arg Lys Leu Leu Glu Lys Glu Gly Leu Glu Phe Lys Arg
    210                 215                 220

Leu Glu Pro Pro Lys Arg Lys Asp Lys Lys Ser Arg Gly Lys Gln Lys
225                 230                 235                 240

Thr Leu Asp Phe Phe
                245

<210> SEQ ID NO 64
<211> LENGTH: 245
<212> TYPE: PRT
<213> ORGANISM: Pyrococcus

<400> SEQUENCE: 64

Ile Lys Glu Lys Pro Thr Ala Asp Glu Ile Lys Glu Leu Leu Asp Ile
1               5                   10                  15

Ala Glu Lys Tyr Gly Gly Val Ile Thr Ile Phe Ala Lys Cys Lys Val
                20                  25                  30

Tyr Tyr Glu Gly Arg Ala Lys Ser Glu Leu Gly Glu Gly Asp Arg Ile
            35                  40                  45

Ile Ile Ile Lys Pro Asp Gly Ser Phe Leu Ile His Gln Asn Lys Lys
50                  55                  60

Arg Glu Pro Val Asn Trp Gln Pro Pro Gly Ser Ser Val Arg Ile Glu
65                  70                  75                  80

Gly Asn Thr Ile Ile Ser Ile Arg Arg Lys Pro Arg Glu Lys Leu Glu
                85                  90                  95
```

```
Val Glu Val Leu Glu Ala Tyr Ser Gly Ile Val Phe Ala Glu Asp
            100                 105                 110

Tyr Glu Glu Leu Ala Leu Thr Gly Ser Glu Ala Glu Met Ala Glu Leu
            115                 120                 125

Ile Phe Gln Asn Pro Asp Ile Ile Glu Lys Gly Phe Lys Pro Leu Phe
        130                 135                 140

Arg Glu Lys Pro Ile Lys His Gly Ile Val Asp Ile Leu Gly Val Asp
145                 150                 155                 160

Lys Glu Gly Asn Ile Val Val Leu Glu Leu Lys Arg Arg Ala Asp
                165                 170                 175

Leu His Ala Val Ser Gln Leu Lys Arg Tyr Val Glu Ser Leu Lys Glu
                180                 185                 190

Glu Tyr Lys Arg Lys Val Arg Gly Ile Leu Val Ala Pro Ser Leu Thr
            195                 200                 205

Glu Gly Ala Arg Lys Leu Leu Glu Lys Glu Gly Leu Glu Phe Lys Arg
        210                 215                 220

Leu Glu Pro Pro Lys Arg Lys Asp Lys Lys Ser Arg Gly Lys Gln Lys
225                 230                 235                 240

Thr Leu Asp Phe Phe
                245

<210> SEQ ID NO 65
<211> LENGTH: 247
<212> TYPE: PRT
<213> ORGANISM: Thermococcus onnurineus

<400> SEQUENCE: 65

Lys Val Glu Ala Val Thr Asn Pro Ser Arg Glu Glu Leu Leu Gly Ile
1               5                   10                  15

Ile Asp Ser Ala Leu Ser Lys Glu Ala Met Leu Thr Ile Phe Ala Arg
            20                  25                  30

Cys Lys Val His Tyr Asp Gly Arg Ala Lys Ser Glu Leu Gly Ser Gly
        35                  40                  45

Asp Arg Val Ile Leu Val Lys Pro Asp Gly Ala Phe Leu Ile His Gln
    50                  55                  60

Ser Lys Lys Arg Glu Pro Val Asn Trp Gln Pro Pro Gly Ser Phe Val
65                  70                  75                  80

Thr Val Glu Glu Arg Asp Gly Ile Ile Val Leu Arg Ser Val Arg Arg
                85                  90                  95

Lys Pro Lys Glu Ile Leu Glu Val Glu Leu Glu Glu Val Tyr Leu Ala
            100                 105                 110

Ser Leu Phe Lys Ala Glu Asp Tyr Glu Glu Leu Ala Leu Thr Gly Ser
        115                 120                 125

Glu Ala Glu Met Ala Glu Met Ile Phe Lys Asn Pro Glu Leu Ile Glu
    130                 135                 140

Pro Gly Phe Arg Pro Leu Phe Arg Glu Lys Ser Ile Gly His Gly Ile
145                 150                 155                 160

Val Asp Ile Leu Gly Arg Asp Arg Glu Gly Asn Leu Val Val Leu Glu
                165                 170                 175

Leu Lys Arg Arg Arg Ala Asp Leu His Ala Val Ser Gln Leu Lys Arg
            180                 185                 190

Tyr Val Glu Ala Leu Arg Ala Glu His Pro Ala Val Arg Gly Ile Leu
        195                 200                 205

Val Ala Pro Ser Leu Thr Ser Gly Ala Lys Lys Leu Leu Glu Lys Glu
```

```
                    210                 215                 220
Gly Leu Glu Phe Arg Arg Val Gln Pro Pro Lys Arg Glu Ser Val Thr
225                 230                 235                 240

Lys Gly Arg Gln Thr Thr Leu
                245

<210> SEQ ID NO 66
<211> LENGTH: 242
<212> TYPE: PRT
<213> ORGANISM: Methanobacterium formicicum

<400> SEQUENCE: 66

Asn Pro Glu Thr Gln Arg Val Leu Glu Ile Ile Asn Glu Gly Leu Ser
1               5                   10                  15

Lys Arg Ala Val Ile Thr Ile Met Ala Ser Cys Arg Val Asn Tyr Asp
                20                  25                  30

Gly Arg Ala Val Ser Arg Leu Gly Val Gly Asp Arg Ile Ile Leu Ile
            35                  40                  45

Lys Ser Asp Gly Ser Phe Ile Ile His Gln Asp Arg Asn Leu Glu Pro
    50                  55                  60

Val Asn Trp Gln Pro Pro Lys Thr Lys Val Thr Val Glu Thr Tyr Gln
65                  70                  75                  80

Gly Met Val Lys Ile Arg Gly Val Arg Arg Asn Pro Ser Glu Ser Leu
                85                  90                  95

Glu Val Glu Ile Leu Gln Thr His Leu Ala Ser Tyr Phe Ile Gly Glu
            100                 105                 110

Asp Val Glu Ser Leu Glu Leu Ala Gly Tyr Glu Ala Asn Met Gly Asp
        115                 120                 125

Leu Ile Phe Lys Asp Pro Glu Val Val Glu Lys Gly Phe Arg Pro Thr
    130                 135                 140

Ser Arg Glu Tyr His Thr Pro Gln Gly Phe Ile Asp Ile Leu Gly Lys
145                 150                 155                 160

Asp Gln Asn Gly Asn Ile Thr Ile Leu Glu Leu Lys Ser Arg Lys Ala
                165                 170                 175

Gly Ile Asn Ala Val Lys Gln Leu Arg Arg Tyr Val Asp Cys Phe Ser
            180                 185                 190

Asp His Lys Glu Ala Val Arg Gly Val Leu Val Ala Pro Ser Ile Thr
        195                 200                 205

Asp Asp Ala Arg Gln Leu Leu Glu Glu Gln Lys Met Glu Phe Lys Ala
    210                 215                 220

Leu Glu Pro Pro Arg Glu Leu Gly Thr Asp Lys Val Val Thr Leu Glu
225                 230                 235                 240

Asn Phe

<210> SEQ ID NO 67
<211> LENGTH: 242
<212> TYPE: PRT
<213> ORGANISM: Thermococcus

<400> SEQUENCE: 67

Met Lys Val Glu Ala Lys Leu Asn Pro Ser Glu Glu Ile Ile Ile Asp
1               5                   10                  15

Leu Phe Ser Lys Gly Leu Ser Lys Glu Ala Ile Leu Thr Ile Phe Ala
                20                  25                  30

His Cys Lys Val Ser Tyr Asn Gly Arg Ala Lys Ser Glu Leu Gly Pro
            35                  40                  45
```

```
Gly Asp Arg Val Ile Ile Lys Pro Asp Gly Ser Phe Leu Ile His
    50                  55                  60

Gln Lys Glu Lys Arg Glu Pro Val Asn Trp Gln Pro Gly Ser Ser
65                  70                  75                  80

Pro Ser Leu Ser Ala Gly Glu Asp Lys Leu Ile Leu Lys Ser Val Arg
                85                  90                  95

Arg Lys Pro Lys Glu Thr Leu Glu Val Glu Leu Ile Asp Val Tyr Leu
                100                 105                 110

Phe Ser Tyr Phe Gln Ala Glu Asp Tyr Glu Thr Leu Ala Leu Met Gly
            115                 120                 125

Ser Glu Ala Glu Met Ala Asp Leu Ile Phe Glu Asn Pro Glu Leu Ile
    130                 135                 140

Glu Asp Gly Phe Lys Pro Leu Phe Lys Glu Lys Ser Ile Lys His Gly
145                 150                 155                 160

Ile Val Asp Ile Leu Gly Lys Asp Lys Asn Gly Asn Ile Val Val Leu
                165                 170                 175

Glu Phe Lys Arg Arg Ala Asp Leu His Ala Val Ser Gln Leu Lys
                180                 185                 190

Arg Tyr Val Glu Thr Ile Lys Glu Glu Tyr Lys Asn Val Arg Gly Ile
            195                 200                 205

Leu Val Ala Pro Ser Leu Thr Ser Gly Ala Lys Arg Leu Leu Glu Lys
    210                 215                 220

Glu Gly Leu Glu Phe Lys Lys Leu Thr Pro Pro Lys Lys Glu Lys Ser
225                 230                 235                 240

Lys Lys

<210> SEQ ID NO 68
<211> LENGTH: 242
<212> TYPE: PRT
<213> ORGANISM: Thermococcus sibiricus

<400> SEQUENCE: 68

Met Lys Val Glu Ala Lys Leu Asn Pro Ser Lys Glu Glu Ile Ile Asp
1               5                   10                  15

Leu Phe Ser Lys Gly Leu Ser Lys Glu Ala Ile Val Thr Ile Phe Ala
                20                  25                  30

His Cys Lys Val Ser Tyr Asn Gly Arg Ala Lys Ser Glu Leu Gly Pro
            35                  40                  45

Gly Asp Arg Val Ile Ile Lys Pro Asp Gly Ser Phe Leu Ile His
    50                  55                  60

Gln Lys Glu Lys Arg Glu Pro Val Asn Trp Gln Pro Gly Ser Ser
65                  70                  75                  80

Pro Ser Leu Ser Ala Gly Glu Asp Lys Leu Ile Leu Lys Ser Val Arg
                85                  90                  95

Arg Lys Pro Lys Glu Thr Leu Glu Val Glu Leu Ile Asp Val Tyr Leu
                100                 105                 110

Phe Ser Tyr Phe Gln Ala Glu Asp Tyr Glu Thr Leu Ala Leu Met Gly
            115                 120                 125

Ser Glu Ala Glu Met Ala Asp Leu Ile Phe Glu Asn Pro Glu Leu Ile
    130                 135                 140

Glu Asp Gly Phe Lys Pro Leu Phe Lys Glu Lys Ser Ile Lys His Gly
145                 150                 155                 160

Ile Val Asp Ile Leu Gly Lys Asp Lys Asn Gly Asn Ile Val Val Leu
                165                 170                 175
```

```
Glu Phe Lys Arg Arg Ala Asp Leu His Ala Val Ser Gln Leu Lys
            180                 185                 190

Arg Tyr Val Glu Thr Ile Lys Glu Glu Tyr Lys Asn Val Arg Gly Ile
        195                 200                 205

Leu Val Ala Pro Ser Leu Thr Ser Gly Ala Lys Arg Leu Leu Glu Lys
    210                 215                 220

Glu Gly Leu Glu Phe Lys Lys Leu Thr Pro Lys Lys Glu Lys Ser
225                 230                 235                 240

Lys Lys

<210> SEQ ID NO 69
<211> LENGTH: 242
<212> TYPE: PRT
<213> ORGANISM: Thermococcus sibiricus

<400> SEQUENCE: 69

Met Lys Val Glu Val Lys Leu Asn Pro Ser Lys Glu Val Ile Asp
1               5                   10                  15

Leu Phe Ser Arg Gly Leu Ser Thr Glu Ala Ile Val Thr Ile Phe Ala
            20                  25                  30

Arg Cys Asn Val Ser Tyr Asp Gly Arg Ala Lys Ser Glu Leu Gly Leu
        35                  40                  45

Gly Asp Arg Val Ile Ile Lys Pro Asp Gly Ser Phe Leu Ile His
    50                  55                  60

Gln Lys Glu Lys Arg Glu Pro Val Asn Trp Gln Pro Gly Ser Ser
65                  70                  75                  80

Val Ser Leu Lys Ile Gly Glu Asp Lys Leu Ile Leu Arg Ser Val Arg
            85                  90                  95

Arg Lys Pro Lys Glu Ile Leu Glu Val Gly Leu Ile Asp Val Tyr Leu
        100                 105                 110

Leu Ser Tyr Phe Gln Ala Glu Asp Tyr Glu Ser Leu Ala Leu Met Gly
    115                 120                 125

Ser Glu Ala Glu Met Ala Asp Leu Val Phe Glu Asn Pro Glu Leu Ile
130                 135                 140

Glu Pro Gly Phe Lys Pro Ile Phe Lys Glu Lys Ser Ile Arg His Gly
145                 150                 155                 160

Ile Ile Asp Ile Leu Gly Lys Asp Lys Asp Gly Asn Ile Val Val Leu
            165                 170                 175

Glu Phe Lys Arg Arg Ala Asp Leu His Ala Val Ser Gln Leu Lys
        180                 185                 190

Arg Tyr Val Glu Thr Met Arg Glu Glu Tyr Lys Asn Val Arg Gly Ile
    195                 200                 205

Leu Val Ala Pro Ser Leu Thr Ser Gly Ala Lys Arg Leu Leu Glu Lys
        210                 215                 220

Glu Gly Leu Glu Phe Lys Lys Leu Thr Pro Lys Lys Glu Lys Ser
225                 230                 235                 240

Arg Lys

<210> SEQ ID NO 70
<211> LENGTH: 241
<212> TYPE: PRT
<213> ORGANISM: Thermococcus zilligii

<400> SEQUENCE: 70

Asn Pro Ser Pro Glu Glu Ile Lys Leu Leu Val Asp Ser Ala Ile Ser
```

```
            1               5                  10                 15
          Ser Glu Ala Leu Leu Thr Ile Phe Ala His Cys Arg Val Tyr Tyr Asp
                          20                 25                 30

Gly Arg Ala Lys Ser Glu Leu Gly Ser Gly Asp Arg Val Ile Ile Val
                          35                 40                 45

Lys Pro Asp Gly Ser Phe Leu Ile His Gln Ser Lys Lys Arg Glu Pro
           50                             55                 60

Val Asn Trp Gln Pro Pro Gly Ser Val Val His Val Glu Leu Arg Glu
           65                 70                     75                 80

Lys Pro Val Leu Val Ser Val Arg Arg Lys Pro Pro Glu Thr Leu Glu
                                  85                 90                 95

Val Glu Leu Glu Glu Val Tyr Leu Ile Thr Val Phe His Ala Glu Asp
                         100                105                110

Tyr Glu Glu Leu Ala Leu Thr Gly Ser Glu Ala Glu Met Ala Glu Leu
                         115                120                125

Ile Phe Glu Gln Pro Glu Val Ile Glu Pro Gly Phe Lys Pro Leu Tyr
                         130                135                140

Arg Glu Lys Pro Val Lys His Gly Ile Val Asp Val Leu Gly Val Asp
          145                150                155                160

Arg Glu Gly Asn Ile Val Val Leu Glu Leu Lys Arg Arg Arg Ala Asp
                                 165                170                175

Leu His Ala Val Ser Gln Leu Lys Arg Tyr Val Glu Thr Leu Lys Glu
                         180                185                190

Glu His Gly Asn Val Arg Gly Ile Leu Val Ala Pro Ser Leu Thr Ser
                         195                200                205

Gly Ala Arg Lys Leu Leu Glu Lys Glu Gly Leu Glu Phe Arg Lys Leu
                         210                215                220

Gln Pro Pro Lys Gly Gly Lys Lys Ser Arg Gly Lys Gln Leu Arg Leu
          225                230                235                240

Phe

<210> SEQ ID NO 71
<211> LENGTH: 239
<212> TYPE: PRT
<213> ORGANISM: Thermococcus kodakarensis KOD1

<400> SEQUENCE: 71

Lys Val Thr Val Ile Thr Ser Pro Ser Thr Glu Glu Leu Val Ser Leu
           1               5                  10                 15

Val Asn Ser Ala Leu Leu Glu Glu Ala Met Leu Thr Ile Phe Ala Arg
                          20                 25                 30

Cys Lys Val His Tyr Asp Gly Arg Ala Lys Ser Glu Leu Gly Ser Gly
                          35                 40                 45

Asp Arg Val Ile Ile Val Lys Pro Asp Gly Ser Phe Leu Ile His Gln
           50                             55                 60

Ser Lys Lys Arg Glu Pro Val Asn Trp Gln Pro Pro Gly Ser Arg Val
           65                 70                     75                 80

Arg Leu Glu Leu Arg Glu Asn Pro Val Leu Val Ser Ile Arg Arg Lys
                                  85                 90                 95

Pro Arg Glu Thr Leu Glu Val Glu Leu Glu Glu Val Tyr Met Val Ser
                         100                105                110

Val Phe Arg Ala Glu Asp Tyr Glu Glu Leu Ala Leu Thr Gly Ser Glu
                         115                120                125

Ala Glu Met Ala Glu Leu Ile Phe Glu Asn Pro Glu Val Ile Glu Pro
```

```
                130                 135                 140
Gly Phe Lys Pro Leu Phe Arg Glu Lys Ala Ile Gly Thr Gly Ile Val
145                 150                 155                 160

Asp Val Leu Gly Arg Asp Ser Asp Gly Asn Ile Val Val Leu Glu Leu
                165                 170                 175

Lys Arg Arg Arg Ala Glu Leu His Ala Val Arg Gln Leu Lys Ser Tyr
                180                 185                 190

Val Glu Ile Leu Arg Glu Glu Tyr Gly Asp Lys Val Arg Gly Ile Leu
                195                 200                 205

Val Ala Pro Ser Leu Thr Ser Gly Ala Lys Arg Leu Leu Glu Lys Glu
                210                 215                 220

Gly Leu Glu Phe Arg Lys Leu Glu Pro Pro Lys Arg Asp Ser Lys
225                 230                 235

<210> SEQ ID NO 72
<211> LENGTH: 239
<212> TYPE: PRT
<213> ORGANISM: Thermococcus kodakarensis KOD1

<400> SEQUENCE: 72

Lys Val Thr Val Ile Thr Ser Pro Ser Thr Glu Glu Leu Val Ser Leu
1               5                   10                  15

Val Asn Ser Ala Leu Leu Glu Glu Ala Met Leu Thr Ile Phe Ala Arg
                20                  25                  30

Cys Lys Val His Tyr Asp Gly Arg Ala Lys Ser Glu Leu Gly Ser Gly
            35                  40                  45

Asp Arg Val Ile Ile Val Lys Pro Asp Gly Ser Phe Leu Ile His Gln
50                  55                  60

Ser Lys Lys Arg Glu Pro Val Asn Trp Gln Pro Pro Gly Ser Arg Val
65                  70                  75                  80

Arg Leu Glu Leu Arg Glu Asn Pro Val Leu Val Ser Ile Arg Arg Lys
                85                  90                  95

Pro Arg Glu Thr Leu Glu Val Glu Leu Glu Val Tyr Met Val Ser
                100                 105                 110

Val Phe Arg Ala Glu Asp Tyr Glu Glu Leu Ala Leu Thr Gly Ser Glu
                115                 120                 125

Ala Glu Met Ala Glu Leu Ile Phe Glu Asn Pro Glu Val Ile Glu Pro
                130                 135                 140

Gly Phe Lys Pro Leu Phe Arg Glu Lys Ala Ile Gly Thr Gly Ile Val
145                 150                 155                 160

Ala Val Leu Gly Arg Asp Ser Asp Gly Asn Ile Val Val Leu Glu Leu
                165                 170                 175

Lys Arg Arg Arg Ala Glu Leu His Ala Val Arg Gln Leu Lys Ser Tyr
                180                 185                 190

Val Glu Ile Leu Arg Glu Glu Tyr Gly Asp Lys Val Arg Gly Ile Leu
                195                 200                 205

Val Ala Pro Ser Leu Thr Ser Gly Ala Lys Arg Leu Leu Glu Lys Glu
                210                 215                 220

Gly Leu Glu Phe Arg Lys Leu Glu Pro Pro Lys Arg Asp Ser Lys
225                 230                 235

<210> SEQ ID NO 73
<211> LENGTH: 241
<212> TYPE: PRT
<213> ORGANISM: Thermococcus barophilus
```

<400> SEQUENCE: 73

```
Pro Ser His Glu Glu Ile Ile Glu Ile Leu Asp Lys Ala Leu Ser Val
1               5                   10                  15
Glu Ala Ile Ile Thr Leu Phe Ala Tyr Cys Arg Val Phe Tyr Glu Gly
            20                  25                  30
Arg Ala Lys Ser Glu Leu Gly Pro Gly Asp Arg Val Ile Ile Ile Lys
        35                  40                  45
Pro Asp Gly Ser Phe Leu Ile His Gln Lys Asn Lys Arg Glu Pro Val
50                  55                  60
Asn Trp Gln Pro Pro Gly Ser Val Val Ser Ile Val Leu Glu Asp Gly
65                  70                  75                  80
Arg Ile Met Leu Arg Ser Val Arg Arg Lys Pro Lys Glu Thr Leu Glu
                85                  90                  95
Val Glu Leu Ile Lys Thr Tyr Leu Val Ser Tyr Phe Gln Ala Glu Asp
            100                 105                 110
Tyr Glu Glu Leu Thr Leu Thr Gly Ser Glu Ala Glu Met Ala Asp Leu
        115                 120                 125
Ile Phe Glu Asn Pro Ser Leu Ile Glu Glu Gly Phe Lys Pro Leu Phe
130                 135                 140
Lys Glu Lys Pro Ile Lys His Gly Ile Val Asp Val Leu Gly Lys Asp
145                 150                 155                 160
Lys His Gly Asn Leu Val Val Leu Glu Leu Lys Arg Arg Arg Ala Asp
                165                 170                 175
Leu His Ala Val Ser Gln Leu Lys Arg Tyr Val Asp Ser Leu Arg Glu
            180                 185                 190
Glu His Lys Asn Val Arg Gly Ile Leu Val Ala Pro Ser Leu Thr Ala
        195                 200                 205
Gly Ala Lys Lys Leu Leu Glu Lys Glu Gly Leu Glu Phe Lys Lys Leu
210                 215                 220
Asn Pro Pro Lys Arg Glu Lys Arg Lys Lys Gly Lys Gln Lys Thr Leu
225                 230                 235                 240
Asp
```

<210> SEQ ID NO 74
<211> LENGTH: 239
<212> TYPE: PRT
<213> ORGANISM: Methanocaldococcus jannaschii

<400> SEQUENCE: 74

```
Leu Thr Asn Pro Thr Thr Lys Asp Leu Glu Asn Phe Ile Asp Met Tyr
1               5                   10                  15
Val Phe Lys Tyr Ile Leu Ile Leu Leu Ala Arg Cys Lys Val Phe Tyr
            20                  25                  30
Glu Gly Arg Ala Lys Ser Gln Leu Glu Glu Gly Asp Arg Val Ile Ile
        35                  40                  45
Ile Lys Pro Asp Gly Ala Phe Leu Ile His Lys Asp Lys Lys Arg Glu
50                  55                  60
Pro Val Asn Trp Gln Pro Ser Gly Ser Ser Ile Trp Glu Val Glu
65                  70                  75                  80
Asp Asn Phe Phe Ile Leu Lys Ser Ile Arg Arg Lys Pro Lys Glu Glu
                85                  90                  95
Leu Lys Val Val Ile Ser Glu Val Tyr His Ala Cys Ala Phe Asn Cys
            100                 105                 110
Glu Asp Tyr Glu Glu Ile Asn Leu Arg Gly Ser Glu Ser Glu Met Ala
```

```
                115                 120                 125
Glu Met Ile Phe Arg Asn Pro Asp Leu Ile Glu Gly Phe Lys Pro
        130                 135                 140

Ile Ser Arg Glu Tyr Gln Ile Pro Thr Gly Ile Val Asp Ile Leu Gly
145                 150                 155                 160

Lys Asp Lys Glu Asn Lys Trp Val Ile Leu Glu Leu Lys Arg Arg Arg
                165                 170                 175

Ala Asp Leu Gln Ala Val Ser Gln Leu Lys Arg Tyr Val Glu Tyr Phe
            180                 185                 190

Lys Asn Lys Tyr Gly Glu Asp Lys Val Arg Gly Ile Leu Val Ser Pro
                195                 200                 205

Ser Leu Thr Thr Gly Ala Glu Lys Leu Leu Lys Glu Glu Asn Leu Glu
        210                 215                 220

Phe Lys Arg Leu Asn Pro Pro Lys Gly Ser Lys Arg Asp Leu Lys
225                 230                 235
```

<210> SEQ ID NO 75
<211> LENGTH: 239
<212> TYPE: PRT
<213> ORGANISM: Methanococcus jannaschii

<400> SEQUENCE: 75

```
Leu Thr Asn Pro Thr Thr Lys Asp Leu Glu Asn Phe Ile Asp Met Tyr
1               5                   10                  15

Val Phe Lys Tyr Ile Leu Ile Leu Leu Ala Arg Cys Lys Val Phe Tyr
                20                  25                  30

Glu Gly Arg Ala Lys Ser Gln Leu Glu Glu Gly Asp Arg Val Ile Ile
            35                  40                  45

Ile Lys Pro Asp Gly Ala Phe Leu Ile His Lys Asp Lys Lys Arg Glu
50                  55                  60

Pro Val Asn Trp Gln Pro Ser Gly Ser Ser Ile Ile Trp Glu Val Glu
65                  70                  75                  80

Asp Asn Phe Phe Ile Leu Lys Ser Ile Arg Arg Lys Pro Lys Glu Glu
                85                  90                  95

Leu Lys Val Val Ile Ser Glu Val Tyr His Ala Cys Ala Phe Asn Cys
            100                 105                 110

Glu Asp Tyr Glu Glu Ile Asn Leu Arg Gly Ser Glu Ser Glu Met Ala
        115                 120                 125

Glu Met Ile Phe Arg Asn Pro Asp Leu Ile Glu Gly Phe Lys Pro
        130                 135                 140

Ile Ser Arg Glu Tyr Gln Ile Pro Thr Gly Ile Val Asp Ile Leu Gly
145                 150                 155                 160

Lys Asp Lys Glu Asn Lys Trp Val Ile Leu Glu Leu Lys Arg Arg Arg
                165                 170                 175

Ala Asp Leu Gln Ala Val Ser Gln Leu Lys Arg Tyr Val Glu Tyr Phe
            180                 185                 190

Lys Asn Lys Tyr Gly Glu Asp Lys Val Arg Gly Ile Leu Val Ser Pro
                195                 200                 205

Ser Leu Thr Thr Gly Ala Glu Lys Leu Leu Lys Glu Glu Asn Leu Glu
        210                 215                 220

Phe Lys Arg Leu Asn Pro Pro Lys Gly Ser Lys Arg Asp Leu Lys
225                 230                 235
```

<210> SEQ ID NO 76
<211> LENGTH: 238

<212> TYPE: PRT
<213> ORGANISM: Methanocaldococcus vulcanius

<400> SEQUENCE: 76

```
Met Lys Val His Phe Leu His Lys Pro Asp Ile Lys Asn Leu Val Asn
1               5                   10                  15

Phe Ile Lys Glu His Ile Tyr Asp Ser Val Ile Leu Leu Ser Arg
                20                  25                  30

Cys Ser Val Ile Tyr Asp Gly Arg Ala Lys Ser Thr Leu Asn Glu Gly
                35                  40                  45

Asp Arg Ile Ile Met Ile Lys Pro Asp Gly Ser Leu Leu Ile His Lys
            50                  55                  60

Asn Lys Lys Arg Glu Pro Val Asn Trp Gln Pro Ser Gly Ser Ser Ile
65                  70                  75                  80

Ser Tyr Lys Ile Glu Asn Lys Gln Phe Ile Arg Ser Ile Arg Lys
                85                  90                  95

Lys Pro Arg Glu Val Leu Glu Ile Ile Val Tyr Glu Val Tyr His Ala
                100                 105                 110

Cys Ala Phe Lys Cys Glu Asp Tyr Glu Glu Leu Asn Leu Thr Gly Ser
                115                 120                 125

Glu Gly Asp Met Val Asp Met Ile Phe Lys Asn Pro Lys Leu Ile Glu
            130                 135                 140

Glu Gly Phe Lys Pro Leu Ser Lys Glu Tyr Gln Ile Pro Thr Gly Ile
145                 150                 155                 160

Ile Asp Ile Leu Gly Lys Asp Glu Asn Asn Asn Trp Val Ile Leu Glu
                165                 170                 175

Leu Lys Arg Arg Arg Ala Asp Leu Gln Ser Val Ser Gln Leu Lys Arg
                180                 185                 190

Tyr Val Glu Tyr Phe Lys Ser Lys Tyr Gly Lys Arg Val Arg Gly
                195                 200                 205

Ile Leu Val Ala Pro Ser Leu Thr Thr Gly Ala Leu Asn Leu Leu Lys
            210                 215                 220

Ser Glu Asn Leu Glu Phe Lys Lys Leu Thr Pro Pro Lys Lys
225                 230                 235
```

<210> SEQ ID NO 77
<211> LENGTH: 235
<212> TYPE: PRT
<213> ORGANISM: Thermococcus paralvinellae

<400> SEQUENCE: 77

```
Met Lys Val Glu Ala Lys Val Asp Pro Ser His Glu Glu Met Val Glu
1               5                   10                  15

Ile Leu Asp Lys Ala Leu Ser Thr Asp Ala Ile Thr Leu Phe Ala
                20                  25                  30

Tyr Cys Arg Val Phe Tyr Glu Gly Arg Ala Lys Ser Glu Leu Gly Pro
                35                  40                  45

Gly Asp Arg Val Ile Ile Lys Pro Asp Gly Ser Phe Leu Ile His
            50                  55                  60

Gln Lys Asn Lys Arg Glu Pro Val Asn Trp Gln Pro Pro Gly Ser Ala
65                  70                  75                  80

Val Ser Ile Val Leu Glu Asp Gly Lys Ile Met Leu Arg Ser Val Arg
                85                  90                  95

Arg Lys Pro Lys Glu Thr Leu Val Glu Leu Ile Lys Thr Tyr Leu
                100                 105                 110
```

```
Val Ser Tyr Phe Gln Ala Glu Asp Tyr Glu Leu Ala Leu Thr Gly
        115                 120                 125

Ser Glu Ala Glu Met Ala Asp Leu Ile Phe Glu Asn Pro Ser Leu Ile
130                 135                 140

Glu Glu Gly Phe Lys Pro Leu Phe Lys Glu Lys Pro Ile Lys His Gly
145                 150                 155                 160

Ile Val Asp Val Leu Gly Arg Asp Lys His Gly Asn Leu Val Val Leu
                165                 170                 175

Glu Leu Lys Arg Arg Arg Ala Asp Leu His Ala Val Ser Gln Leu Lys
                180                 185                 190

Arg Tyr Val Asp Ala Leu Arg Glu Glu His Lys Asn Val Arg Gly Ile
        195                 200                 205

Leu Val Ala Pro Ser Ile Thr Ala Gly Ala Lys Lys Leu Leu Glu Lys
210                 215                 220

Glu Gly Leu Glu Phe Lys Lys Leu Asn Pro Pro
225                 230                 235

<210> SEQ ID NO 78
<211> LENGTH: 235
<212> TYPE: PRT
<213> ORGANISM: Thermococcus paralvinellae

<400> SEQUENCE: 78

Met Lys Val Glu Ala Lys Val Asp Pro Ser His Glu Glu Met Val Glu
1               5                   10                  15

Ile Leu Asp Lys Ala Leu Ser Thr Asp Ala Ile Ile Thr Leu Phe Ala
                20                  25                  30

Tyr Cys Arg Val Phe Tyr Glu Gly Arg Ala Lys Ser Glu Leu Gly Pro
            35                  40                  45

Gly Asp Arg Val Ile Ile Lys Pro Asp Gly Ser Phe Leu Ile His
        50                  55                  60

Gln Lys Asn Lys Arg Glu Pro Val Asn Trp Gln Pro Pro Gly Ser Ala
65                  70                  75                  80

Val Ser Ile Val Leu Glu Asp Gly Lys Ile Met Leu Arg Ser Val Arg
                85                  90                  95

Arg Lys Pro Lys Glu Thr Leu Glu Val Glu Leu Ile Lys Thr Tyr Leu
            100                 105                 110

Val Ser Tyr Phe Gln Ala Glu Asp Tyr Glu Leu Ala Leu Thr Gly
        115                 120                 125

Ser Glu Ala Glu Met Ala Asp Leu Ile Phe Glu Asn Pro Ser Leu Ile
130                 135                 140

Glu Glu Gly Phe Lys Pro Leu Phe Lys Glu Lys Pro Ile Lys His Gly
145                 150                 155                 160

Ile Val Asp Val Leu Gly Arg Asp Lys His Gly Asn Leu Val Val Leu
                165                 170                 175

Glu Leu Lys Arg Arg Arg Ala Asp Leu His Ala Val Ser Gln Leu Lys
                180                 185                 190

Arg Tyr Val Asp Ala Leu Arg Glu Glu His Lys Asn Val Arg Gly Ile
        195                 200                 205

Leu Val Ala Pro Ser Ile Thr Ala Gly Ala Lys Lys Leu Leu Glu Lys
210                 215                 220

Glu Gly Leu Glu Phe Lys Lys Leu Asn Pro Pro
225                 230                 235

<210> SEQ ID NO 79
```

```
<211> LENGTH: 237
<212> TYPE: PRT
<213> ORGANISM: Halomicrobium mukohataei

<400> SEQUENCE: 79

Glu Thr Leu Ser Asp Pro Asp Phe Asp Ala Ala Gly Asp Leu Val Glu
1               5                   10                  15

Arg Gly Ile Asp Ala Gly Ala Leu Val Thr Leu Phe Gly Arg Cys Arg
            20                  25                  30

Val Asp Tyr Asp Gly Arg Ala Thr Ser Thr Leu Gly Pro Gly Asp Arg
        35                  40                  45

His Val Met Leu Lys Pro Asp Gly Ala Ala Leu Val His Thr Asp Glu
    50                  55                  60

Gly Gln Gln Pro Val Asn Trp Gln Pro Gly Cys Glu His Ala Val
65                  70                  75                  80

Arg Val Val Asp Gly Glu Phe Val Val Glu Ser Glu Arg Ser Ser Pro
                85                  90                  95

Asp Glu Leu Leu Ser Ile Ala Phe Glu Ser Leu Ser His Val Gly Val
            100                 105                 110

Phe Asp Val Thr Asp Ala Thr Asp Leu Ser Leu Thr Gly Thr Glu Glu
        115                 120                 125

Asp Leu Arg Glu Arg Ile Leu Asp Asp Pro Asp Leu Leu Glu Pro Ala
    130                 135                 140

Phe Thr Pro Leu Ala Thr Glu Arg Ser Thr Pro Ala Gly Ala Ile Asp
145                 150                 155                 160

Ile Tyr Gly Glu Asp Ala Asp Gly Arg Thr Val Val Glu Leu Lys
                165                 170                 175

Arg Arg Arg Val Gly Pro Asp Ala Val Gly Gln Leu Asp Arg Tyr Val
            180                 185                 190

Gln Ala Leu Gly Arg Asp Leu His Asp Glu Ala Glu Ile Arg Gly Leu
        195                 200                 205

Leu Val Ala Pro Ser Val Thr Asp Arg Ala Arg Glu Leu Leu Ala Gln
    210                 215                 220

Lys Gly Leu Glu Phe Val Ser Leu Ala Pro Pro Glu Glu
225                 230                 235

<210> SEQ ID NO 80
<211> LENGTH: 235
<212> TYPE: PRT
<213> ORGANISM: Halomicrobium katesii

<400> SEQUENCE: 80

Leu Ser Asp Pro Asp Phe Asp Ala Ala Gly Asp Leu Val Glu Arg Gly
1               5                   10                  15

Ile Asp Ala Gly Ala Leu Val Thr Leu Phe Gly Arg Cys Arg Val Asp
            20                  25                  30

Tyr Asp Gly Arg Ala Thr Ser Thr Leu Gly Pro Gly Asp Arg His Val
        35                  40                  45

Met Leu Lys Pro Asp Gly Ala Ala Leu Val His Thr Asp Glu Gly Gln
    50                  55                  60

Gln Pro Val Asn Trp Gln Pro Pro Gly Cys Glu His Ala Val Arg Val
65                  70                  75                  80

Val Asp Gly Glu Phe Val Val Glu Ser Glu Arg Ser Ser Pro Asp Glu
                85                  90                  95

Leu Leu Ser Ile Ala Phe Glu Ser Leu Ala His Val Gly Val Phe Asp
            100                 105                 110
```

```
Val Thr Asp Ala Thr Asp Leu Ser Leu Thr Gly Thr Glu Ala Asp Leu
        115                 120                 125

Arg Glu Arg Ile Leu Asp Asp Pro Asp Leu Leu Glu Pro Ala Phe Thr
130                 135                 140

Pro Leu Ala Thr Glu Arg Ser Thr Pro Ala Gly Ala Ile Asp Ile Tyr
145                 150                 155                 160

Gly Glu Asp Gly Asp Gly Arg Thr Val Val Glu Leu Lys Arg Arg
                165                 170                 175

Arg Val Gly Pro Asp Ala Val Gly Gln Leu Asp Arg Tyr Val Gln Ala
                180                 185                 190

Leu Gly Arg Asp Leu His Asp Glu Ala Glu Ile Arg Gly Ile Leu Val
        195                 200                 205

Ala Pro Ser Val Thr Asp Arg Ala Arg Glu Leu Leu Ala Gln Lys Gly
        210                 215                 220

Leu Glu Phe Val Ser Leu Ala Pro Pro Glu Glu
225                 230                 235

<210> SEQ ID NO 81
<211> LENGTH: 235
<212> TYPE: PRT
<213> ORGANISM: Haloarcula japonica

<400> SEQUENCE: 81

Glu Thr Leu Thr Tyr Pro Asp Pro Ala Asp Ala Leu Asp Leu Ala Ser
1               5                   10                  15

Arg Asn Ala Asp Arg Gly Ala Leu Val Thr Leu Val Gly Thr Cys Thr
                20                  25                  30

Val Glu Tyr Glu Gly Arg Ala Ala Ser Ser Leu Gly Leu Gly Asp Arg
            35                  40                  45

His Val Met Leu Lys Pro Asp Gly Ala Ala Leu Val His Thr Asp Glu
        50                  55                  60

Gly Gln Gln Pro Val Asn Trp Gln Pro Pro Gly Cys Glu His Ser Ile
65                  70                  75                  80

Ser Val Asp Asp Gly Ser Leu Val Val Arg Ser Thr Arg Ser Thr Pro
                85                  90                  95

Glu Glu Leu Leu Glu Val Thr Phe Glu Thr Val Ala His Ala Ala Ala
                100                 105                 110

Phe Asp Val Thr Asp Ser Lys Asp Leu Ala Leu Thr Gly Thr Glu Ala
            115                 120                 125

Asp Leu Lys Asp Arg Ile Leu Asp Glu Pro Gly Leu Val Glu Ser Gly
        130                 135                 140

Phe Thr Pro Leu Ala Thr Glu Arg Glu Thr Pro Ala Gly Ala Val Asp
145                 150                 155                 160

Ile Tyr Gly Glu Asp Ala Asp Gly Arg Thr Thr Ile Leu Glu Leu Lys
                165                 170                 175

Arg Arg Arg Val Gly Pro Asp Ala Val Gly Gln Leu Gly Arg Tyr Val
                180                 185                 190

Asp Ala Leu Glu Arg Asp Leu His Ala Asp Thr Glu Val Arg Gly Ile
        195                 200                 205

Leu Val Ala Pro Ser Val Thr Asp Arg Ala Arg Gln Leu Leu Ala Glu
        210                 215                 220

Lys Gly Leu Glu Phe Val Ser Leu Glu Pro Pro
225                 230                 235
```

<210> SEQ ID NO 82
<211> LENGTH: 226
<212> TYPE: PRT
<213> ORGANISM: Pyrococcus furiosus

<400> SEQUENCE: 82

Glu Asn Pro Arg Ile Glu Glu Ile Lys Glu Leu Leu Glu Val Ala Glu
1               5                   10                  15

Ser Arg Glu Gly Leu Leu Thr Ile Phe Ala Arg Cys Thr Val Tyr Tyr
            20                  25                  30

Glu Gly Arg Ala Lys Ser Glu Leu Gly Glu Gly Asp Arg Ile Ile Ile
        35                  40                  45

Ile Lys Pro Asp Gly Ser Phe Leu Ile His Gln Lys Lys Lys Arg Glu
50                  55                  60

Pro Val Asn Trp Gln Pro Pro Gly Ser Lys Val Lys Met Glu Gly Asn
65                  70                  75                  80

Ser Leu Ile Ser Ile Arg Arg Asn Pro Lys Glu Thr Leu Lys Val Asp
                85                  90                  95

Ile Ile Glu Ala Tyr Ala Ala Val Leu Phe Met Ala Glu Asp Tyr Glu
            100                 105                 110

Glu Leu Thr Leu Thr Gly Ser Glu Ala Glu Met Ala Glu Leu Ile Phe
        115                 120                 125

Gln Asn Pro Asn Val Ile Glu Glu Gly Phe Lys Pro Met Phe Arg Glu
130                 135                 140

Lys Pro Ile Lys His Gly Ile Val Asp Val Leu Gly Val Asp Arg Glu
145                 150                 155                 160

Gly Asn Ile Val Val Leu Glu Leu Lys Arg Arg Arg Ala Asp Leu His
                165                 170                 175

Ala Val Ser Gln Leu Lys Arg Tyr Val Asp Ala Leu Lys Glu Glu His
            180                 185                 190

Gly Asn Lys Val Arg Gly Ile Leu Val Ala Pro Ser Leu Thr Glu Gly
        195                 200                 205

Ala Lys Lys Leu Leu Glu Lys Leu Gly Leu Glu Phe Arg Lys Leu Glu
210                 215                 220

Pro Pro
225

<210> SEQ ID NO 83
<211> LENGTH: 226
<212> TYPE: PRT
<213> ORGANISM: Pyrococcus furiosus

<400> SEQUENCE: 83

Glu Asn Pro Arg Ile Glu Glu Ile Lys Glu Leu Leu Glu Val Ala Glu
1               5                   10                  15

Ser Arg Glu Gly Leu Leu Thr Ile Phe Ala Arg Cys Thr Val Tyr Tyr
            20                  25                  30

Glu Gly Arg Ala Lys Ser Glu Leu Gly Glu Gly Asp Arg Ile Ile Ile
        35                  40                  45

Ile Lys Pro Asp Gly Ser Phe Leu Ile His Gln Lys Lys Lys Arg Glu
50                  55                  60

Pro Val Asn Trp Gln Pro Pro Gly Ser Lys Val Lys Met Glu Gly Asn
65                  70                  75                  80

Ser Leu Ile Ser Ile Arg Arg Asn Pro Lys Glu Thr Leu Lys Val Asp
                85                  90                  95

Ile Ile Glu Ala Tyr Ala Ala Val Leu Phe Met Ala Glu Asp Tyr Glu

```
            100                 105                 110
Glu Leu Thr Leu Thr Gly Ser Glu Ala Glu Met Ala Glu Leu Ile Phe
        115                 120                 125
Gln Asn Pro Asn Val Ile Glu Glu Gly Phe Lys Pro Met Phe Arg Glu
    130                 135                 140
Lys Pro Ile Lys His Gly Ile Val Asp Val Leu Gly Val Asp Arg Glu
145                 150                 155                 160
Gly Asn Ile Val Val Leu Glu Leu Lys Arg Arg Arg Ala Asp Leu His
                165                 170                 175
Ala Val Ser Gln Leu Lys Arg Tyr Val Asp Ala Leu Lys Glu Glu His
            180                 185                 190
Gly Asn Lys Val Arg Gly Ile Leu Val Ala Pro Ser Leu Thr Glu Gly
        195                 200                 205
Ala Lys Lys Leu Leu Glu Lys Leu Gly Leu Glu Phe Arg Lys Leu Glu
    210                 215                 220
Pro Pro
225

<210> SEQ ID NO 84
<211> LENGTH: 226
<212> TYPE: PRT
<213> ORGANISM: Pyrococcus furiosus DSM 3638

<400> SEQUENCE: 84

Glu Asn Pro Arg Ile Glu Glu Ile Lys Glu Leu Leu Glu Val Ala Glu
1               5                   10                  15
Ser Arg Glu Gly Leu Leu Thr Ile Phe Ala Arg Cys Thr Val Tyr Tyr
            20                  25                  30
Glu Gly Arg Ala Lys Ser Glu Leu Gly Glu Gly Asp Arg Ile Ile Ile
        35                  40                  45
Ile Lys Pro Asp Gly Ser Phe Leu Ile His Gln Lys Lys Arg Glu
    50                  55                  60
Pro Val Asn Trp Gln Pro Pro Gly Ser Lys Val Lys Met Glu Gly Asn
65                  70                  75                  80
Ser Leu Ile Ser Ile Arg Arg Asn Pro Lys Glu Thr Leu Lys Val Asp
                85                  90                  95
Ile Ile Glu Ala Tyr Ala Ala Val Leu Phe Met Ala Glu Asp Tyr Glu
            100                 105                 110
Glu Leu Thr Leu Thr Gly Ser Glu Ala Glu Met Ala Glu Leu Ile Phe
        115                 120                 125
Gln Asn Pro Asn Val Ile Glu Glu Gly Phe Lys Pro Met Phe Arg Glu
    130                 135                 140
Lys Pro Ile Lys His Gly Ile Val Asp Val Leu Gly Val Asp Arg Glu
145                 150                 155                 160
Gly Asn Ile Val Val Leu Glu Leu Lys Arg Arg Arg Ala Asp Leu His
                165                 170                 175
Ala Val Ser Gln Leu Lys Arg Tyr Val Asp Ala Leu Lys Glu Glu His
            180                 185                 190
Gly Asn Lys Val Arg Gly Ile Leu Val Ala Pro Ser Leu Thr Glu Gly
        195                 200                 205
Ala Lys Lys Leu Leu Glu Lys Leu Gly Leu Glu Phe Arg Lys Leu Glu
    210                 215                 220
Pro Pro
225
```

<210> SEQ ID NO 85
<211> LENGTH: 226
<212> TYPE: PRT
<213> ORGANISM: Pyrococcus furiosus

<400> SEQUENCE: 85

| Glu | Asn | Pro | Arg | Ile | Glu | Glu | Ile | Lys | Glu | Leu | Leu | Glu | Val | Ala | Glu |
|---|---|---|---|---|---|---|---|---|---|---|---|---|---|---|---|
| 1 | | | | 5 | | | | | 10 | | | | | 15 | |

| Ser | Arg | Glu | Gly | Leu | Leu | Thr | Ile | Phe | Ala | Arg | Cys | Thr | Val | Tyr | Tyr |
|---|---|---|---|---|---|---|---|---|---|---|---|---|---|---|---|
| | | | 20 | | | | | 25 | | | | | 30 | | |

| Glu | Gly | Arg | Ala | Lys | Ser | Glu | Leu | Gly | Glu | Gly | Asp | Arg | Ile | Ile | Ile |
|---|---|---|---|---|---|---|---|---|---|---|---|---|---|---|---|
| | | | 35 | | | | | 40 | | | | | 45 | | |

| Ile | Lys | Pro | Asp | Gly | Ser | Phe | Leu | Ile | His | Gln | Lys | Lys | Arg | Glu |
|---|---|---|---|---|---|---|---|---|---|---|---|---|---|---|
| 50 | | | | | 55 | | | | | 60 | | | | |

| Pro | Val | Asn | Trp | Gln | Pro | Pro | Gly | Ser | Lys | Val | Lys | Met | Glu | Gly | Asn |
|---|---|---|---|---|---|---|---|---|---|---|---|---|---|---|---|
| 65 | | | | | 70 | | | | | 75 | | | | | 80 |

| Ser | Leu | Ile | Ser | Ile | Arg | Arg | Asn | Pro | Lys | Glu | Thr | Leu | Lys | Val | Asp |
|---|---|---|---|---|---|---|---|---|---|---|---|---|---|---|---|
| | | | | 85 | | | | | 90 | | | | | 95 | |

| Ile | Ile | Glu | Ala | Tyr | Ala | Ala | Val | Leu | Phe | Met | Ala | Glu | Asp | Tyr | Glu |
|---|---|---|---|---|---|---|---|---|---|---|---|---|---|---|---|
| | | | 100 | | | | | 105 | | | | | 110 | | |

| Glu | Leu | Thr | Leu | Thr | Gly | Ser | Glu | Ala | Glu | Met | Ala | Glu | Leu | Ile | Phe |
|---|---|---|---|---|---|---|---|---|---|---|---|---|---|---|---|
| | | | 115 | | | | | 120 | | | | | 125 | | |

| Gln | Asn | Pro | Asn | Val | Ile | Glu | Glu | Gly | Phe | Lys | Pro | Met | Phe | Arg | Glu |
|---|---|---|---|---|---|---|---|---|---|---|---|---|---|---|---|
| | 130 | | | | | 135 | | | | | 140 | | | | |

| Lys | Pro | Ile | Lys | His | Gly | Ile | Val | Asp | Val | Leu | Gly | Val | Asp | Arg | Glu |
|---|---|---|---|---|---|---|---|---|---|---|---|---|---|---|---|
| 145 | | | | | 150 | | | | | 155 | | | | | 160 |

| Gly | Asn | Ile | Val | Val | Leu | Glu | Leu | Lys | Arg | Arg | Arg | Ala | Asp | Leu | His |
|---|---|---|---|---|---|---|---|---|---|---|---|---|---|---|---|
| | | | | 165 | | | | | 170 | | | | | 175 | |

| Ala | Val | Ser | Gln | Leu | Lys | Arg | Tyr | Val | Asp | Ala | Leu | Lys | Glu | Glu | His |
|---|---|---|---|---|---|---|---|---|---|---|---|---|---|---|---|
| | | | 180 | | | | | 185 | | | | | 190 | | |

| Gly | Asn | Lys | Val | Arg | Gly | Ile | Leu | Val | Ala | Pro | Ser | Leu | Thr | Glu | Gly |
|---|---|---|---|---|---|---|---|---|---|---|---|---|---|---|---|
| | | 195 | | | | | 200 | | | | | 205 | | | |

| Ala | Lys | Lys | Leu | Leu | Glu | Lys | Leu | Gly | Leu | Glu | Phe | Arg | Lys | Leu | Glu |
|---|---|---|---|---|---|---|---|---|---|---|---|---|---|---|---|
| | 210 | | | | | 215 | | | | | 220 | | | | |

| Pro | Pro |
|---|---|
| 225 | |

<210> SEQ ID NO 86
<211> LENGTH: 232
<212> TYPE: PRT
<213> ORGANISM: Halostagnicola larsenii

<400> SEQUENCE: 86

| Leu | Glu | Arg | Pro | Ala | Val | Glu | Thr | Ala | Cys | Glu | Thr | Val | Ala | Asp | Gly |
|---|---|---|---|---|---|---|---|---|---|---|---|---|---|---|---|
| 1 | | | | 5 | | | | | 10 | | | | | 15 | |

| Ile | Asp | Arg | Asp | Ala | Leu | Val | Thr | Val | Phe | Gly | Arg | Cys | Ser | Val | Glu |
|---|---|---|---|---|---|---|---|---|---|---|---|---|---|---|---|
| | | | 20 | | | | | 25 | | | | | 30 | | |

| Tyr | Asp | Gly | Arg | Ala | Ser | Ser | Gln | Leu | Asp | Ala | Gly | Asp | Arg | His | Val |
|---|---|---|---|---|---|---|---|---|---|---|---|---|---|---|---|
| | | | 35 | | | | | 40 | | | | | 45 | | |

| Met | Cys | Lys | Pro | Asp | Gly | Thr | Thr | Leu | Val | His | Thr | Asp | Glu | Gly | Gln |
|---|---|---|---|---|---|---|---|---|---|---|---|---|---|---|---|
| | 50 | | | | | 55 | | | | | 60 | | | | |

| Gln | Pro | Val | Asn | Trp | Gln | Pro | Pro | Gly | Cys | Thr | His | Glu | Val | Phe | Cys |
|---|---|---|---|---|---|---|---|---|---|---|---|---|---|---|---|
| 65 | | | | | 70 | | | | | 75 | | | | | 80 |

| Asp | Asp | Gly | Ala | Leu | Phe | Leu | Glu | Ser | His | Arg | Ser | Thr | Pro | Gln | Glu |
|---|---|---|---|---|---|---|---|---|---|---|---|---|---|---|---|
| | | | | 85 | | | | | 90 | | | | | 95 | |

```
Arg Leu Leu Ile Gly Phe Glu Arg Val Val His Val Ser Val Phe Pro
                100                 105                 110

Val Ser Asp Ser Ser Glu Leu Thr Leu Val Gly Thr Glu Glu Asp Leu
            115                 120                 125

Arg Gln Arg Ile Leu Glu Asp Pro Gly Leu Leu Glu Pro Gly Phe Arg
        130                 135                 140

Pro Leu Ala Thr Glu Arg Asp Thr Pro Ala Gly Ala Ile Asp Ile Tyr
145                 150                 155                 160

Gly Glu Asp Ser Val Gly Arg Ala Val Val Glu Leu Lys Arg Arg
                165                 170                 175

Arg Val Gly Pro Asp Ala Val Ser Gln Leu Arg Arg Tyr Val Asp Ala
            180                 185                 190

Leu Glu Arg Asp Leu His Ala Asp Ala Ser Ile Arg Gly Ile Leu Val
        195                 200                 205

Ala Pro Ser Val Thr Asp Arg Ala Ser Gly Leu Leu Gly Glu His Gly
210                 215                 220

Leu Glu Phe Val Ser Leu Glu Pro
225                 230

<210> SEQ ID NO 87
<211> LENGTH: 222
<212> TYPE: PRT
<213> ORGANISM: Thermococcus barophilus

<400> SEQUENCE: 87

Ile Thr Leu Phe Ala Tyr Cys Arg Val Phe Tyr Glu Gly Arg Ala Lys
1               5                   10                  15

Ser Glu Leu Gly Pro Gly Asp Arg Val Ile Ile Lys Pro Asp Gly
            20                  25                  30

Ser Phe Leu Ile His Gln Lys Asn Lys Arg Glu Pro Val Asn Trp Gln
        35                  40                  45

Pro Pro Gly Ser Val Val Ser Ile Val Leu Gly Asp Gly Arg Ile Met
50                  55                  60

Leu Arg Ser Val Arg Arg Lys Pro Lys Glu Thr Leu Glu Val Glu Leu
65                  70                  75                  80

Ile Lys Thr Tyr Leu Val Ser Tyr Phe Gln Ala Glu Asp Tyr Glu Glu
                85                  90                  95

Leu Thr Leu Thr Gly Ser Glu Ala Glu Met Ala Asp Leu Ile Phe Glu
            100                 105                 110

Asn Pro Ser Leu Ile Glu Glu Gly Phe Lys Pro Leu Phe Lys Glu Lys
        115                 120                 125

Pro Ile Lys His Gly Ile Val Asp Val Leu Gly Lys Asp Lys His Gly
        130                 135                 140

Asn Leu Val Val Leu Glu Leu Lys Arg Arg Ala Asp Leu His Ala
145                 150                 155                 160

Val Ser Gln Leu Lys Arg Tyr Val Asp Ser Leu Arg Glu Glu His Lys
                165                 170                 175

Asn Val Arg Gly Ile Leu Val Ala Pro Ser Leu Thr Ala Gly Ala Lys
            180                 185                 190

Lys Leu Leu Glu Lys Glu Gly Leu Glu Phe Lys Leu Asn Pro Pro
        195                 200                 205

Lys Arg Glu Lys Arg Lys Lys Gly Lys Gln Lys Thr Leu Asp
    210                 215                 220

<210> SEQ ID NO 88
```

<211> LENGTH: 221
<212> TYPE: PRT
<213> ORGANISM: Pyrococcus

<400> SEQUENCE: 88

```
Phe Glu Lys Pro Ser Ile Glu Glu Val Lys Glu Leu Phe Lys Met Ala
1               5                   10                  15

Glu Lys His Gly Gly Val Val Thr Val Phe Ala Arg Cys Lys Val Tyr
            20                  25                  30

Tyr Glu Gly Arg Ala Lys Ser Glu Leu Gly Glu Gly Asp Arg Ile Ile
        35                  40                  45

Ile Val Lys Pro Asp Gly Thr Phe Leu Val His Gln Asn Lys Lys Arg
50                  55                  60

Glu Pro Val Asn Trp Gln Pro Pro Gly Ser Ile Val Ser Ile Glu Gly
65                  70                  75                  80

Asn Ser Ile Ile Ser Ile Arg Arg Arg Pro Arg Glu Lys Leu Glu Val
                85                  90                  95

Glu Leu Ile Asp Val Tyr Ala Val Val Val Phe Leu Ala Glu Asp Tyr
            100                 105                 110

Lys Glu Leu Ala Leu Thr Gly Ser Glu Ala Glu Met Ala Lys Leu Ile
        115                 120                 125

Phe Glu Asn Pro Glu Val Ile Glu Glu Gly Phe Lys Pro Met Phe Arg
130                 135                 140

Glu Lys Pro Ile Lys His Gly Ile Val Asp Ile Met Gly Val Asp Lys
145                 150                 155                 160

Asn Gly Asn Ile Val Ile Leu Glu Leu Lys Arg Arg Lys Ala Asp Leu
                165                 170                 175

His Ala Val Ser Gln Leu Lys Arg Tyr Val Asp Ala Leu Lys Glu Glu
            180                 185                 190

Tyr Gly Glu Arg Val Arg Gly Ile Leu Val Ala Pro Ser Leu Thr Glu
        195                 200                 205

Gly Ala Lys Lys Leu Leu Glu Lys Glu Gly Leu Glu Phe
    210                 215                 220
```

<210> SEQ ID NO 89
<211> LENGTH: 221
<212> TYPE: PRT
<213> ORGANISM: Thermococcus cleftensis

<400> SEQUENCE: 89

```
Leu Thr Ile Phe Ala Arg Cys Arg Val His Tyr Asp Gly Arg Ala Lys
1               5                   10                  15

Ser Glu Leu Gly Ser Gly Asp Arg Val Ile Leu Val Lys Pro Asp Gly
            20                  25                  30

Ala Phe Leu Val His Gln Ser Lys Arg Glu Pro Val Asn Trp Gln
        35                  40                  45

Pro Pro Gly Ser Phe Val Thr Val Glu Val Arg Glu Gly Leu Val Val
50                  55                  60

Leu Arg Ser Val Arg Arg Lys Pro Lys Glu Ile Leu Glu Val Glu Leu
65                  70                  75                  80

Glu Glu Val Tyr Leu Ala Ser Leu Phe Asn Ala Glu Asp Tyr Glu Glu
                85                  90                  95

Leu Ala Leu Thr Gly Ser Glu Ala Glu Met Ala Glu Met Ile Phe Arg
            100                 105                 110

Asn Pro Glu Leu Ile Glu Pro Gly Phe Lys Pro Leu Phe Arg Glu Lys
        115                 120                 125
```

```
Gln Ile Gly His Gly Ile Val Asp Ile Leu Gly Lys Asp Gly Arg Gly
            130                 135                 140

Asn Leu Val Val Leu Glu Leu Lys Arg Arg Lys Ala Asp Leu His Ala
145                 150                 155                 160

Val Ser Gln Leu Lys Arg Tyr Val Glu Ala Leu Glu Arg Glu His Gly
            165                 170                 175

Lys Val Arg Gly Ile Leu Val Ala Pro Ser Leu Thr Ser Gly Ala Lys
            180                 185                 190

Lys Leu Leu Glu Lys Glu Gly Leu Glu Phe Arg Lys Val Glu Pro Pro
            195                 200                 205

Lys Lys Glu Lys Leu Gly Arg Gly Arg Gln Lys Thr Leu
            210                 215                 220
```

<210> SEQ ID NO 90
<211> LENGTH: 224
<212> TYPE: PRT
<213> ORGANISM: Palaeococcus pacificus

<400> SEQUENCE: 90

```
Ile Thr Leu Phe Ala His Cys Ser Val Phe Tyr Asp Gly Arg Ala Lys
1               5                   10                  15

Ser Glu Leu Gly Ala Gly Asp Arg Val Ile Met Ile Lys Pro Asp Gly
            20                  25                  30

Thr Phe Leu Ile His Gln Lys Glu Lys Arg Val Pro Val Asn Trp Gln
        35                  40                  45

Pro Pro Gly Ser Ile Val Ser Phe Gln Ile Glu Glu Gly Lys Ile Lys
    50                  55                  60

Leu Arg Ser Val Arg Arg Lys Pro Lys Glu Ile Leu Glu Val Glu Leu
65                  70                  75                  80

Leu Lys Val Tyr Leu Ile Ser Tyr Phe Gln Ala Glu Asp Tyr Glu Ala
                85                  90                  95

Leu Asn Leu Met Gly Ser Glu Ala Glu Met Ala Asp Leu Ile Leu Gln
            100                 105                 110

Asn Pro Ser Ile Ile Glu Glu Gly Phe Lys Ala Leu Gln Lys Glu Lys
        115                 120                 125

Pro Ile Lys His Gly Ile Ile Asp Ile Tyr Gly Val Asp Arg Asp Gly
    130                 135                 140

Asn Ile Val Val Leu Glu Leu Lys Arg Arg Arg Ala Asp Leu His Ala
145                 150                 155                 160

Val Ser Gln Leu Lys Arg Tyr Val Asp Ala Leu Lys Glu Glu His Gly
                165                 170                 175

Ser Val Arg Gly Ile Leu Val Ala Pro Ser Leu Thr Ser Gly Ala Glu
            180                 185                 190

Lys Leu Leu Lys Asp Leu Gly Leu Glu Phe Lys Lys Leu Asn Pro Pro
        195                 200                 205

Lys Arg Glu Lys Ala Arg Lys Gly Lys Gln Lys Thr Leu Asp Met Leu
    210                 215                 220
```

<210> SEQ ID NO 91
<211> LENGTH: 222
<212> TYPE: PRT
<213> ORGANISM: Methanosphaera stadtmanae

<400> SEQUENCE: 91

```
Ile Ile Ile Leu Ala Gln Cys His Val Glu Tyr Glu Gly Arg Ala Arg
1               5                   10                  15
```

-continued

```
Ser Arg Leu Asp Lys Gly Asp Arg Leu Ile Leu Ile Lys Lys Asp Gly
            20                  25                  30

Thr Phe Thr Ile His Gln Glu Leu Asn Leu Asp Pro Val Asn Trp Gln
        35                  40                  45

Ala Pro Gly Cys Lys Asn Lys Val Ser Leu Lys Glu Asn Gln Ile Ile
 50                  55                  60

Leu Gln Ser Ile Lys Thr Lys Pro Asp Glu Glu Ile Thr Val Tyr Leu
65                  70                  75                  80

Asp Thr Val Tyr Cys Ala Thr Tyr Tyr Asn Cys Val Asp Thr Lys Asn
                85                  90                  95

Leu Glu Ile Arg Gly Tyr Glu Lys His Met Val Asp Leu Ala Trp Glu
            100                 105                 110

Lys Pro Glu Leu Ile Glu Lys Gly Phe Arg Pro Thr Arg Arg Glu Tyr
        115                 120                 125

Gln Thr Glu Asn Gly Phe Ile Asp Leu Met Gly Thr Asp Lys Asp Glu
130                 135                 140

Lys Leu Met Ile Leu Glu Phe Lys Ser Arg Lys Ala Gly Thr Asn Ala
145                 150                 155                 160

Val Lys Gln Leu Lys Gly Tyr Val Glu Cys Phe Met Asp Asn Lys Glu
                165                 170                 175

Phe Val Arg Gly Ile Ile Val Ala Pro Asp Ile Thr Asp Asn Ala Leu
            180                 185                 190

Glu Leu Leu Lys Ser Leu Gln Met Glu Phe Ile Pro Leu Asn Pro Pro
        195                 200                 205

Lys Asp Leu Leu Thr Lys Lys Ala Ser Thr Leu Asp Ser Phe
210                 215                 220
```

<210> SEQ ID NO 92
<211> LENGTH: 223
<212> TYPE: PRT
<213> ORGANISM: Methanocaldococcus

<400> SEQUENCE: 92

```
Leu Ile Leu Leu Ala Arg Cys Arg Val Phe Tyr Glu Gly Arg Ala Lys
1               5                   10                  15

Ser Gln Leu Glu Glu Gly Asp Arg Val Ile Ile Lys Pro Asp Gly
            20                  25                  30

Thr Phe Leu Ile His Lys Asp Lys Lys Arg Glu Pro Val Asn Trp Gln
        35                  40                  45

Pro Pro Gly Ser Asn Ile Ile Trp Lys Val Glu Asp Asn Tyr Phe Ile
 50                  55                  60

Leu Lys Ser Ile Arg Arg Lys Pro Lys Glu Glu Leu Lys Val Val Ile
65                  70                  75                  80

Ser Glu Val Tyr His Thr Cys Ala Phe Asn Cys Glu Asp Tyr Glu Glu
                85                  90                  95

Leu Asn Leu Thr Gly Ser Glu Ser Glu Met Ala Glu Met Ile Phe Arg
            100                 105                 110

Asn Pro Asn Leu Ile Glu Glu Gly Phe Lys Pro Leu Ser Arg Glu Tyr
        115                 120                 125

Gln Ile Pro Thr Gly Ile Ile Asp Ile Leu Gly Lys Asp Lys Asp Glu
130                 135                 140

Arg Trp Val Ile Leu Glu Leu Lys Arg Arg Ala Asp Leu Gln Ala
145                 150                 155                 160

Val Ser Gln Leu Lys Arg Tyr Val Glu Tyr Phe Lys Ser Lys Tyr Gly
```

```
            165                 170                 175
Arg Asp Arg Val Arg Gly Ile Leu Val Ala Pro Ser Leu Thr Val Gly
            180                 185                 190

Ala Glu Arg Leu Leu Lys Glu Glu Asn Leu Glu Phe Lys Lys Leu Asn
            195                 200                 205

Pro Pro Lys Gly Ser Lys Lys Asp Leu Lys Gln Asn Met Lys Ser
            210                 215                 220

<210> SEQ ID NO 93
<211> LENGTH: 221
<212> TYPE: PRT
<213> ORGANISM: Thermococcus

<400> SEQUENCE: 93

Val Asn Ile Phe Ala His Cys Arg Val Phe Tyr Asp Gly Arg Ala Lys
1               5                   10                  15

Ser Glu Leu Gly Pro Gly Asp Arg Val Ile Leu Ile Lys Pro Asp Gly
            20                  25                  30

Ser Phe Leu Ile His Gln Lys Glu Lys Arg Glu Pro Val Asn Trp Gln
        35                  40                  45

Pro Pro Gly Ser Ser Val Gly Leu Glu Ile Asn Asp Gly Lys Leu Phe
    50                  55                  60

Leu Arg Ser Val Arg Arg Lys Pro Arg Glu Ile Leu Glu Val Glu Leu
65                  70                  75                  80

Leu Asn Val Tyr Leu Ile Ser Tyr Phe Gln Ala Glu Asp Tyr Glu Glu
                85                  90                  95

Leu Ala Leu Thr Gly Ser Glu Ala Glu Met Ala Asp Leu Ile Phe Glu
            100                 105                 110

Asp Pro Ser Leu Ile Glu Ala Gly Phe Lys Pro Leu Phe Arg Glu Lys
        115                 120                 125

Pro Ile Lys His Gly Ile Val Asp Val Leu Gly Val Asp Lys Glu Gly
    130                 135                 140

Asn Ile Val Ile Leu Glu Leu Lys Arg Arg Arg Ala Asp Leu His Ala
145                 150                 155                 160

Val Ser Gln Leu Lys Arg Tyr Val Glu Ala Met Arg Glu Glu His Glu
                165                 170                 175

Lys Val Arg Gly Ile Leu Val Ala Pro Ser Leu Thr Ser Gly Ala Lys
            180                 185                 190

Lys Leu Leu Glu Lys Glu Gly Leu Glu Phe Arg Lys Leu Thr Pro Pro
        195                 200                 205

Lys Arg Gly Lys Ser Lys Arg Gly Arg Gln Lys Thr Leu
    210                 215                 220

<210> SEQ ID NO 94
<211> LENGTH: 215
<212> TYPE: PRT
<213> ORGANISM: Thermococcus sibiricus

<400> SEQUENCE: 94

Val Thr Ile Phe Ala Arg Cys Asn Val Ser Tyr Asp Gly Arg Ala Lys
1               5                   10                  15

Ser Glu Leu Gly Leu Gly Asp Arg Val Ile Ile Lys Pro Asp Gly
            20                  25                  30

Ser Phe Leu Ile His Gln Lys Glu Lys Arg Glu Pro Val Asn Trp Gln
        35                  40                  45

Pro Pro Gly Ser Ser Val Ser Leu Lys Ile Gly Glu Asp Lys Leu Ile
```

```
              50                  55                  60
Leu Arg Ser Val Arg Arg Lys Pro Lys Glu Ile Leu Glu Val Gly Leu
 65                  70                  75                  80

Ile Asp Val Tyr Leu Leu Ser Tyr Phe Gln Ala Glu Asp Tyr Glu Ser
                     85                  90                  95

Leu Ala Leu Met Gly Ser Glu Ala Glu Met Ala Asp Leu Val Phe Glu
                100                 105                 110

Asn Pro Glu Leu Ile Glu Pro Gly Phe Lys Pro Ile Phe Lys Glu Lys
            115                 120                 125

Ser Ile Arg His Gly Ile Ile Asp Ile Leu Gly Lys Asp Lys Asp Gly
        130                 135                 140

Asn Ile Val Val Leu Glu Phe Lys Arg Arg Ala Asp Leu His Ala
145                 150                 155                 160

Val Ser Gln Leu Lys Arg Tyr Val Glu Thr Met Arg Glu Glu Tyr Lys
                165                 170                 175

Asn Val Arg Gly Ile Leu Val Ala Pro Ser Leu Thr Ser Gly Ala Lys
            180                 185                 190

Arg Leu Leu Glu Lys Glu Gly Leu Glu Phe Lys Lys Leu Thr Pro Pro
        195                 200                 205

Lys Lys Glu Lys Ser Arg Lys
    210                 215

<210> SEQ ID NO 95
<211> LENGTH: 221
<212> TYPE: PRT
<213> ORGANISM: Thermococcus piezophilus

<400> SEQUENCE: 95

Leu Thr Ile Phe Ala Arg Cys Lys Val His Tyr Asp Gly Arg Ala Lys
  1               5                  10                  15

Ser Glu Leu Gly Ser Gly Asp Arg Val Ile Leu Val Lys Pro Asp Gly
                 20                  25                  30

Ala Phe Leu Ile His Gln Ser Lys Lys Arg Glu Pro Val Asn Trp Gln
             35                  40                  45

Pro Pro Gly Ser Phe Val Thr Val Glu Glu Arg Asp Gly Ile Ile Val
         50                  55                  60

Leu Arg Ser Val Arg Arg Lys Pro Lys Glu Ile Leu Glu Val Glu Leu
 65                  70                  75                  80

Glu Glu Val Tyr Leu Ala Ser Leu Phe Lys Ala Glu Asp Tyr Glu Glu
                 85                  90                  95

Leu Ala Leu Thr Gly Ser Glu Ala Glu Met Ala Glu Met Ile Phe Lys
                100                 105                 110

Asn Pro Glu Leu Ile Glu Pro Gly Phe Arg Pro Leu Phe Arg Glu Lys
            115                 120                 125

Ser Ile Gly His Gly Ile Val Asp Ile Leu Gly Arg Asp Arg Glu Gly
        130                 135                 140

Asn Leu Val Val Leu Glu Leu Lys Arg Arg Ala Asp Leu His Ala
145                 150                 155                 160

Val Ser Gln Leu Lys Arg Tyr Val Glu Ala Leu Arg Ala Glu His Pro
                165                 170                 175

Ala Val Arg Gly Ile Leu Val Ala Pro Ser Leu Thr Ser Gly Ala Lys
            180                 185                 190

Lys Leu Leu Glu Lys Glu Gly Leu Glu Phe Arg Arg Val Gln Pro Pro
        195                 200                 205
```

```
Lys Arg Glu Ser Val Ala Lys Gly Arg Gln Thr Thr Leu
    210                 215                 220
```

<210> SEQ ID NO 96
<211> LENGTH: 221
<212> TYPE: PRT
<213> ORGANISM: Thermococcus

<400> SEQUENCE: 96

```
Val Asn Ile Phe Ala His Cys Arg Val Phe Tyr Asp Gly Arg Ala Lys
1               5                   10                  15

Ser Glu Leu Gly Pro Gly Asp Arg Val Ile Leu Ile Lys Pro Asp Gly
            20                  25                  30

Ser Phe Leu Ile His Gln Lys Glu Lys Arg Glu Pro Val Asn Trp Gln
        35                  40                  45

Pro Pro Gly Ser Ser Val Gly Leu Glu Val Lys Glu Gly Arg Ile Phe
    50                  55                  60

Leu Arg Ser Ile Arg Arg Lys Pro Arg Glu Ile Leu Glu Val Glu Leu
65                  70                  75                  80

Leu His Val Tyr Leu Ile Ser Tyr Phe Gln Ala Glu Asp Tyr Glu Glu
                85                  90                  95

Leu Ala Leu Thr Gly Ser Glu Ala Glu Met Ala Asp Leu Ile Phe Glu
            100                 105                 110

Asn Pro Ser Val Ile Glu Asp Gly Phe Lys Pro Leu Phe Lys Glu Lys
        115                 120                 125

Pro Ile Lys His Gly Ile Val Asp Val Leu Gly Val Asp Lys Glu Gly
    130                 135                 140

Asn Ile Val Val Leu Glu Leu Lys Arg Arg Arg Ala Asp Leu His Ala
145                 150                 155                 160

Val Ser Gln Leu Lys Arg Tyr Val Glu Ala Met Lys Glu Glu His Glu
                165                 170                 175

Lys Val Arg Gly Ile Leu Val Ala Pro Ser Leu Thr Ser Gly Ala Lys
            180                 185                 190

Lys Leu Leu Glu Lys Glu Gly Leu Glu Phe Arg Arg Leu Thr Pro Pro
        195                 200                 205

Lys Arg Gly Lys Ser Lys Arg Gly Arg Gln Lys Thr Leu
    210                 215                 220
```

<210> SEQ ID NO 97
<211> LENGTH: 221
<212> TYPE: PRT
<213> ORGANISM: Thermococcus thioreducens

<400> SEQUENCE: 97

```
Leu Thr Ile Phe Ala Arg Cys Lys Val His Tyr Asp Gly Arg Ala Lys
1               5                   10                  15

Ser Glu Leu Gly Ser Gly Asp Arg Val Ile Ile Lys Pro Asp Gly
            20                  25                  30

Ala Phe Leu Ile His Gln Ser Arg Lys Arg Glu Pro Val Asn Trp Gln
        35                  40                  45

Pro Pro Gly Ser Phe Val Met Met Glu Glu Arg Asp Gly Ile Leu Val
    50                  55                  60

Leu Arg Ser Val Arg Arg Lys Pro Lys Glu Ile Leu Glu Val Glu Leu
65                  70                  75                  80

Glu Glu Val Tyr Leu Ile Ser Leu Phe Lys Ala Glu Asp Tyr Glu Glu
                85                  90                  95
```

```
Leu Ala Leu Thr Gly Ser Glu Ala Glu Met Ala Glu Met Val Phe Arg
                100                 105                 110

Asn Pro Glu Leu Ile Glu Pro Gly Phe Lys Pro Leu Phe Arg Glu Lys
            115                 120                 125

Gln Ile Gly His Gly Ile Val Asp Ile Leu Gly Arg Asp Arg Asp Gly
        130                 135                 140

Asn Leu Val Val Leu Glu Leu Lys Arg Arg Lys Ala Asp Leu His Ala
145                 150                 155                 160

Val Ser Gln Leu Lys Arg Tyr Val Glu Ala Leu Lys Arg Glu His Glu
                165                 170                 175

Thr Val Arg Gly Ile Leu Val Ala Pro Ser Leu Thr Ala Gly Ala Lys
            180                 185                 190

Lys Leu Leu Glu Lys Glu Gly Leu Glu Phe Arg Arg Val Gln Pro Pro
        195                 200                 205

Lys Arg Glu Lys Phe Gly Arg Gly Arg Gln Lys Thr Leu
            210                 215                 220

<210> SEQ ID NO 98
<211> LENGTH: 221
<212> TYPE: PRT
<213> ORGANISM: Thermococcus litoralis

<400> SEQUENCE: 98

Val Asn Ile Phe Ala His Cys Arg Val Phe Tyr Asp Gly Arg Ala Lys
1               5                   10                  15

Ser Glu Leu Gly Pro Gly Asp Arg Val Ile Leu Ile Lys Pro Asp Gly
            20                  25                  30

Ser Phe Leu Ile His Gln Lys Glu Lys Arg Glu Pro Val Asn Trp Gln
        35                  40                  45

Pro Pro Gly Ser Ser Val Gly Leu Glu Val Lys Glu Asp Lys Ile Phe
    50                  55                  60

Leu Arg Ser Ile Arg Arg Lys Pro Arg Glu Ile Leu Glu Val Glu Leu
65                  70                  75                  80

Leu Asn Val Tyr Leu Ile Ser Tyr Phe Gln Ala Glu Asp Tyr Glu Glu
                85                  90                  95

Leu Ala Leu Thr Gly Ser Glu Ala Glu Met Ala Asp Leu Ile Phe Glu
                100                 105                 110

Asn Pro Ser Leu Ile Glu Asp Gly Phe Lys Pro Leu Phe Lys Glu Lys
            115                 120                 125

Pro Ile Lys His Gly Ile Val Asp Val Leu Gly Val Asp Lys Glu Gly
        130                 135                 140

Asn Ile Val Ile Leu Glu Leu Lys Arg Arg Ala Asp Leu His Ala
145                 150                 155                 160

Val Ser Gln Leu Lys Arg Tyr Val Glu Ala Met Arg Glu Glu His Glu
                165                 170                 175

Lys Val Arg Gly Ile Leu Val Ala Pro Ser Leu Thr Ser Gly Ala Lys
            180                 185                 190

Lys Leu Leu Glu Lys Glu Gly Leu Glu Phe Arg Lys Leu Thr Pro Pro
        195                 200                 205

Lys Arg Gly Lys Ser Lys Arg Gly Arg Gln Lys Thr Leu
            210                 215                 220

<210> SEQ ID NO 99
<211> LENGTH: 221
<212> TYPE: PRT
<213> ORGANISM: Thermococcus onnurineus
```

<400> SEQUENCE: 99

```
Leu Thr Ile Phe Ala Arg Cys Lys Val His Tyr Asp Gly Arg Ala Lys
1               5                   10                  15

Ser Glu Leu Gly Ser Gly Asp Arg Val Ile Leu Val Lys Pro Asp Gly
            20                  25                  30

Ala Phe Leu Ile His Gln Ser Lys Lys Arg Glu Pro Val Asn Trp Gln
        35                  40                  45

Pro Pro Gly Ser Phe Val Thr Val Glu Glu Arg Asp Gly Ile Ile Val
50                  55                  60

Leu Arg Ser Val Arg Arg Lys Pro Lys Glu Ile Leu Glu Val Glu Leu
65                  70                  75                  80

Glu Glu Val Tyr Leu Ala Ser Leu Phe Lys Ala Glu Asp Tyr Glu Glu
                85                  90                  95

Leu Ala Leu Thr Gly Ser Glu Ala Glu Met Ala Glu Met Ile Phe Lys
            100                 105                 110

Asn Pro Glu Leu Ile Glu Pro Gly Phe Arg Pro Leu Phe Arg Glu Lys
        115                 120                 125

Ser Ile Gly His Gly Ile Val Asp Ile Leu Gly Arg Asp Arg Glu Gly
130                 135                 140

Asn Leu Val Val Leu Glu Leu Lys Arg Arg Arg Ala Asp Leu His Ala
145                 150                 155                 160

Val Ser Gln Leu Lys Arg Tyr Val Glu Ala Leu Arg Ala Glu His Pro
                165                 170                 175

Ala Val Arg Gly Ile Leu Val Ala Pro Ser Leu Thr Ser Gly Ala Lys
            180                 185                 190

Lys Leu Leu Glu Lys Glu Gly Leu Glu Phe Arg Arg Val Gln Pro Pro
        195                 200                 205

Lys Arg Glu Ser Val Thr Lys Gly Arg Gln Thr Thr Leu
210                 215                 220
```

<210> SEQ ID NO 100
<211> LENGTH: 215
<212> TYPE: PRT
<213> ORGANISM: Thermococcus celericrescens

<400> SEQUENCE: 100

```
Leu Thr Ile Phe Ala Arg Cys Lys Val His Tyr Asp Gly Arg Ala Lys
1               5                   10                  15

Ser Glu Leu Gly Ser Gly Asp Arg Val Ile Ile Lys Pro Asp Gly
            20                  25                  30

Ala Phe Leu Ile His Gln Ser Lys Lys Arg Glu Pro Val Asn Trp Gln
        35                  40                  45

Pro Pro Gly Ser Phe Val Thr Val Glu Glu Arg Asp Gly Ile Ile Ile
50                  55                  60

Leu Arg Ser Val Arg Arg Lys Pro Lys Glu Ile Leu Glu Val Glu Leu
65                  70                  75                  80

Glu Glu Val Tyr Leu Val Ser Leu Phe Lys Ala Glu Asp Tyr Glu Glu
                85                  90                  95

Leu Thr Leu Thr Gly Ser Glu Ala Glu Met Ala Glu Met Ile Phe Gly
            100                 105                 110

Asn Pro Glu Leu Ile Glu Pro Gly Phe Lys Pro Leu Phe Arg Glu Lys
        115                 120                 125

Gln Ile Gly His Gly Ile Val Asp Ile Leu Gly Arg Asp Lys Asn Gly
130                 135                 140
```

-continued

Asn Leu Val Val Leu Glu Leu Lys Arg Arg Lys Ala Asp Leu His Ala
145                 150                 155                 160

Val Ser Gln Leu Lys Arg Tyr Val Glu Gly Leu Ser Lys Glu His Glu
                165                 170                 175

Gly Val Arg Gly Ile Leu Val Ala Pro Ser Leu Thr Ser Gly Ala Lys
            180                 185                 190

Arg Leu Leu Glu Lys Glu Gly Leu Glu Phe Arg Lys Val Gln Pro Pro
        195                 200                 205

Lys Arg Glu Lys Leu Gly Lys
    210                 215

<210> SEQ ID NO 101
<211> LENGTH: 215
<212> TYPE: PRT
<213> ORGANISM: Thermococcus

<400> SEQUENCE: 101

Val Thr Ile Phe Ala His Cys Lys Val Phe Tyr Asp Gly Arg Ala Lys
1               5                   10                  15

Ser Glu Leu Gly Pro Gly Asp Arg Val Ile Ile Lys Pro Asp Gly
            20                  25                  30

Ser Phe Leu Ile His Gln Lys Glu Lys Arg Glu Pro Val Asn Trp Gln
        35                  40                  45

Pro Pro Gly Ser Ser Val Ser Leu Asp Val Lys Glu Asp Lys Leu Ile
    50                  55                  60

Leu Arg Ser Val Arg Arg Lys Pro Lys Glu Ile Leu Glu Val Glu Leu
65                  70                  75                  80

Ile Asp Val Tyr Leu Phe Ser Tyr Phe Gln Ala Glu Asp Tyr Glu Ala
                85                  90                  95

Leu Ala Leu Val Gly Ser Glu Ala Glu Met Ala Asp Leu Val Phe Glu
            100                 105                 110

Asn Pro Glu Leu Ile Glu Asp Gly Phe Lys Pro Leu Phe Lys Glu Lys
        115                 120                 125

Ser Ile Arg His Gly Ile Val Asp Leu Leu Gly Lys Asp Lys Asp Gly
    130                 135                 140

Asn Ile Val Ile Leu Glu Phe Lys Arg Arg Ala Asp Leu His Ala
145                 150                 155                 160

Val Ser Gln Leu Lys Arg Tyr Val Glu Thr Met Arg Glu Glu Tyr Glu
                165                 170                 175

Lys Val Arg Gly Ile Leu Val Ala Pro Ser Leu Thr Ser Gly Ala Arg
            180                 185                 190

Arg Leu Leu Glu Lys Glu Gly Leu Glu Phe Lys Lys Leu Lys Pro Pro
        195                 200                 205

Lys Gln Glu Lys Ser Arg Lys
    210                 215

<210> SEQ ID NO 102
<211> LENGTH: 215
<212> TYPE: PRT
<213> ORGANISM: Thermococcus

<400> SEQUENCE: 102

Leu Thr Ile Phe Ala Arg Cys Arg Val His Tyr Asp Gly Arg Ala Lys
1               5                   10                  15

Ser Glu Leu Gly Ser Gly Asp Arg Val Ile Ile Lys Pro Asp Gly
            20                  25                  30

-continued

```
Ala Phe Leu Ile His Gln Ser Lys Lys Arg Glu Pro Val Asn Trp Gln
            35                  40                  45

Pro Pro Gly Ser Phe Val Thr Ile Glu Glu Arg Asp Gly Ile Ile Ile
 50                  55                  60

Leu Arg Ser Val Arg Arg Lys Pro Lys Glu Ile Leu Glu Val Glu Leu
 65                  70                  75                  80

Glu Glu Val Tyr Leu Val Ser Leu Phe Lys Ala Glu Asp Tyr Glu Glu
                 85                  90                  95

Leu Ala Leu Thr Gly Ser Glu Ala Glu Met Ala Glu Met Ile Phe Arg
            100                 105                 110

Asn Pro Glu Leu Ile Glu Pro Gly Phe Lys Pro Leu Phe Arg Glu Lys
            115                 120                 125

Gln Ile Gly His Gly Ile Val Asp Ile Leu Gly Arg Asp Gly Asp Gly
        130                 135                 140

Asn Leu Val Val Leu Glu Leu Lys Arg Arg Lys Ala Asp Leu His Ala
145                 150                 155                 160

Val Ser Gln Leu Lys Arg Tyr Val Glu Ala Leu Ser Arg Glu His Glu
                165                 170                 175

Ser Val Arg Gly Ile Leu Val Ala Pro Ser Leu Thr Ser Gly Ala Lys
            180                 185                 190

Lys Leu Leu Glu Lys Glu Gly Leu Glu Phe Arg Lys Val Gln Pro Pro
            195                 200                 205

Lys Arg Glu Lys Leu Gly Lys
        210                 215

<210> SEQ ID NO 103
<211> LENGTH: 213
<212> TYPE: PRT
<213> ORGANISM: Thermococcus kodakarensis

<400> SEQUENCE: 103

Leu Thr Ile Phe Ala Arg Cys Lys Val His Tyr Asp Gly Arg Ala Lys
 1               5                  10                  15

Ser Glu Leu Gly Ser Gly Asp Arg Val Ile Ile Val Lys Pro Asp Gly
                 20                  25                  30

Ser Phe Leu Ile His Gln Ser Lys Lys Arg Glu Pro Val Asn Trp Gln
            35                  40                  45

Pro Pro Gly Ser Arg Val Arg Leu Glu Leu Arg Glu Asn Pro Val Leu
 50                  55                  60

Val Ser Ile Arg Arg Lys Pro Arg Glu Thr Leu Glu Val Glu Leu Glu
 65                  70                  75                  80

Glu Val Tyr Met Val Ser Val Phe Arg Ala Glu Asp Tyr Glu Glu Leu
                 85                  90                  95

Ala Leu Thr Gly Ser Glu Ala Glu Met Ala Glu Leu Ile Phe Glu Asn
            100                 105                 110

Pro Glu Val Ile Glu Pro Gly Phe Lys Pro Leu Phe Arg Glu Lys Ala
            115                 120                 125

Ile Gly Thr Gly Ile Val Asp Val Leu Gly Arg Asp Ser Asp Gly Asn
        130                 135                 140

Ile Val Val Leu Glu Leu Lys Arg Arg Arg Ala Glu Leu His Ala Val
145                 150                 155                 160

Arg Gln Leu Lys Ser Tyr Val Glu Ile Leu Arg Glu Glu Tyr Gly Asp
                165                 170                 175

Lys Val Arg Gly Ile Leu Val Ala Pro Ser Leu Thr Ser Gly Ala Lys
```

```
                    180                 185                 190
Arg Leu Leu Glu Lys Glu Gly Leu Glu Phe Arg Lys Leu Glu Pro Pro
            195                 200                 205

Lys Arg Asp Ser Lys
    210

<210> SEQ ID NO 104
<211> LENGTH: 208
<212> TYPE: PRT
<213> ORGANISM: Thermococcus peptonophilus

<400> SEQUENCE: 104

Leu Thr Ile Phe Ala Arg Cys Lys Val His Tyr Asp Gly Arg Ala Lys
1               5                   10                  15

Ser Glu Leu Gly Ser Gly Asp Arg Val Ile Ile Val Lys Pro Asp Gly
            20                  25                  30

Ser Phe Leu Ile His Gln Ser Lys Lys Arg Glu Pro Val Asn Trp Gln
        35                  40                  45

Pro Pro Gly Ser Arg Val Arg Leu Glu Leu Arg Glu Asn Pro Val Leu
    50                  55                  60

Val Ser Ile Arg Arg Lys Pro Lys Glu Thr Leu Glu Val Glu Leu Glu
65                  70                  75                  80

Glu Val Tyr Met Val Ser Val Phe Arg Ala Glu Asp Tyr Glu Glu Leu
                85                  90                  95

Thr Leu Thr Gly Ser Glu Ala Glu Met Ala Glu Leu Ile Phe Glu Asn
            100                 105                 110

Pro Glu Val Ile Glu Pro Gly Phe Lys Pro Leu Phe Arg Glu Lys Thr
        115                 120                 125

Ile Lys Ser Gly Ile Val Asp Ile Leu Gly Arg Asp Ser Asn Gly Asn
    130                 135                 140

Ile Val Val Leu Glu Leu Lys Arg Arg Arg Ala Glu Leu His Ala Val
145                 150                 155                 160

Arg Gln Leu Lys Ser Tyr Val Glu Ile Leu Lys Glu Tyr Gly Asp
                165                 170                 175

Lys Val Arg Gly Ile Leu Val Ala Pro Ser Leu Thr Ser Gly Ala Lys
            180                 185                 190

Arg Leu Leu Glu Lys Glu Gly Leu Glu Phe Arg Lys Leu Glu Pro Pro
            195                 200                 205

<210> SEQ ID NO 105
<211> LENGTH: 24
<212> TYPE: DNA
<213> ORGANISM: Artificial Sequence
<220> FEATURE:
<223> OTHER INFORMATION: Synthetic consstruct

<400> SEQUENCE: 105
cgccagggtt ttcccagtca cgac                                          24

<210> SEQ ID NO 106
<211> LENGTH: 24
<212> TYPE: DNA
<213> ORGANISM: Artificial Sequence
<220> FEATURE:
<223> OTHER INFORMATION: Synthetic construct

<400> SEQUENCE: 106
gtcgtgactg ggaaaaccct ggcg                                          24
```

```
<210> SEQ ID NO 107
<211> LENGTH: 24
<212> TYPE: DNA
<213> ORGANISM: Artificial Sequence
<220> FEATURE:
<223> OTHER INFORMATION: Synthetic construct

<400> SEQUENCE: 107
gtcgtgactg ggtaaaccct ggcg                                              24

<210> SEQ ID NO 108
<211> LENGTH: 76
<212> TYPE: DNA
<213> ORGANISM: Artificial Sequence
<220> FEATURE:
<223> OTHER INFORMATION: Synthetic constuct

<400> SEQUENCE: 108
atctgatcgg aagagcacac gtctgaactc cagtctacac tctttcccta cacgacgctc      60
ttccgatctg atcgga                                                      76

<210> SEQ ID NO 109
<211> LENGTH: 54
<212> TYPE: DNA
<213> ORGANISM: Artificial Sequence
<220> FEATURE:
<223> OTHER INFORMATION: Synthetic construct

<400> SEQUENCE: 109
agagcacacg tctgaactcc agtctacact ctttccctac acgacgctct tccg             54
```

METHOD FOR REMOVING AND/OR DETECTING NUCLEIC ACIDS HAVING MISMATCHED NUCLEOTIDES

CROSS REFERENCE

This application is a § 371 application of International Application No. PCT/US2018/036875, filed Jun. 11, 2018, which claims the benefit of U.S. Provisional Application No. 62/525,803, filed Jun. 28, 2017. The entire contents of these applications are incorporated herein by reference in their entirety.

BACKGROUND

During next generation DNA sequencing, the DNA molecules to be sequenced are often sheared into fragments, repaired, and adapters of known sequence are ligated to the insert library. A key step in DNA sequencing sample preparation is ligation of oligonucleotide adapters to a population of DNA fragments. The DNA fragments are typically 3' tailed with dA to prevent self-ligation of library DNA. Adapters are designed having a 3'-T overhang to preferentially ligate to the 3'-dA of the fragments. During ligation, the adapters are in excess over the fragments in order to maximize ligation efficiency. Typically, a molar ratio of 10:1 adapter:insert is recommended to maximize ligation efficiency (Head, et al., Biotechniques, 2014, 56, 61-68). However, use of higher adapter:fragment ratios lead to "adapter dimers" that result from self-ligation of the adapters directly to each other rather than a library insert sequence.

The problem of adapter dimers is magnified if the input sample amount is low or of poor quality such as DNA or cDNA from biopsies, FFPE, tissues or single cells (Head 2014). With low DNA input or with poor quality input, the ratio of adapter:insert is greater than 10:1 (for example 100:1, 1000:1 or 10,000:1) and leads to more adapter dimers and low library conversion efficiency. Adapter dimers are also problematic during small RNA library preparation and form the majority of ligated DNA products (Shore, et al., PLoS One, 2016, 11, e0167009).

Once formed, adapter dimers are more efficiently amplified during PCR than libraries containing longer inserts. Due to their short size, adapter dimers form clusters on sequencing flow cells very efficiently. However, because adapter dimers contain no insert, sequencing the adapter dimer yields no useful data. In an Illumina sequencing run, a low level (5%) of adapter dimer contamination can result in 60% of sequencing reads coming from adapter dimers. Adapter dimer contamination therefore lowers the DNA sequencing quality and output and increases the cost of sequencing.

To minimize the formation and accumulation of DNA adapter dimers during sample preparation, several strategies have been developed to separate adapter dimers from libraries with inserts ligated to adapters. For example, adapter dimers can be removed using beads. Alternatively, ligated DNA libraries can be separated from adapter dimer by gel electrophoresis and the band corresponding to the library cut out and purified from the gel. Other methods include the use of blocking locked nucleic acids (LNAs) to reduce adapter dimer ligation (Kawano, et al., Biotechniques, 2010, 49, 751-755). However these methods lead to overall sample loss and limit automation of library construction (Shore, et al., Methods in Molecular Biology, 2018, 1712, 145-161).

US 2014/0356867 describes cleavage of adapter dimers using Cas9. However, a major source of adapter dimers— adapter dimers that contain a T-T mismatch—are not described in this publication. Moreover, not only may the guide RNAs hybridize to genomic sequences to produce undesirable off target cleavage, but introduction of guide RNA molecules into an amplification and/or sequencing reaction can potentially cause additional artefacts. In another example, WO 2013/188037 describes a method by which CRISPR stem loops are engineered into RNA adapters so that dimers of those adaptors can be recognized by Cas6 and cleaved prior to reverse transcription. WO 2013/188037 makes no mention of adapter dimers that contain a T-T mismatch, or DNA adaptors. In view of the above, methods are needed to eliminate adapter dimers to enable higher quality DNA sequencing especially at low input.

Reducing or eliminating adapter dimers would enable higher library conversion efficiency of both normal and low input libraries due to 1) higher ratios of adapter:insert that increase ligation efficiency and 2) higher PCR efficiency of libraries in the absence of adapter dimers and resulting in higher quality and yield of DNA sequencing.

SUMMARY

Many of the adapters used for the construction of next generation sequencing libraries have a single nucleotide 3' overhang. Such adapters, in theory, are only capable of ligating to other molecules that contain a single nucleotide 3' A overhang providing the adaptor overhang is complementary to A. Nucleotides complementary to A are referred to as T. Adaptors should not ligate to other molecules that contain a single nucleotide 3' T overhang. Throughout the present specification and claims, "T" includes analogs such as U and modified Ts and modified Us.

It has been found that the adapter dimers created during next generation sequencing library construction often contain a T:T mismatch at the ligation junction. These molecules can be efficiently eliminated using an EndoMS as described herein. EndoMS specifically cleaves both strands of a double-stranded DNA (dsDNA) only if it contains a mismatch. In some embodiments, the EndoMS treatment step may additionally remove molecules that contain damaged nucleotides from the sample.

A variety of methods and kits are described herein. In some embodiments, the method for cleaving adapter dimers produced during a ligation reaction, may include: (a) ligating a T-tailed double-stranded adapter to A-tailed double-stranded fragments of nucleic acid to produce ligation products that comprise: (i) adapter-ligated double-stranded nucleic acid fragments and (ii) double-stranded adapter dimers that comprise a T:T mismatch at the ligation junction; and (b) cleaving both strands of the adapter dimers using EndoMS.

A method for cleaving a nucleic acid is also provided. In some embodiments, the method may include: hybridizing the nucleic acid with an oligonucleotide that is not perfectly complementary to a target sequence within the nucleic acid, to produce a duplex that comprises one or more single nucleotide mismatches; and treating the duplex with EndoMS, thereby cleaving the nucleic acid at the target sequence containing the single nucleotide mismatch.

A method for identifying a single mismatched nucleotide in a double-stranded nucleic acid is also provided. In these embodiments, the method may comprise: (a) reacting a sample comprising the double-stranded nucleic acid with an EndoMS to produce a reaction product, wherein the EndoMS cleaves both strands of the nucleic acid only if it contains a mismatch; (b) subjecting the reaction product of (a) to amplification under conditions that amplify the double-stranded nucleic acid if it is uncleaved; and (c) detecting the presence of an amplification product, wherein the presence of the product indicates that the double-stranded nucleic acid does not have a mismatched nucleotide and the absence of a product indicates that the double-stranded nucleic acid has a mismatched nucleotide.

Other embodiments may include targeting mismatches in purified genomic DNA using EndoMS. Other embodiments may include targeting mismatches in vivo in nucleic acids in eukaryotic cells using bacterial of archaeal EndoMS genes delivered by transformation using extra chromosomal DNA. Alternatively, EndoMS proteins may be delivered in vivo in the eukaryotic cells using liposomes or various transport proteins known in the art.

BRIEF DESCRIPTION OF THE FIGURES

The skilled artisan will understand that the drawings, described below, are for illustration purposes only. The drawings are not intended to limit the scope of the present teachings in any way.

FIG. 1A-1B EndoMS eliminates double-stranded oligonucleotides that have a mismatch.

FIG. 1A shows the sequences of the double-stranded oligonucleotides used.

FIG. 1B shows EndoMS was incubated with either the T:A or T:T substrate for various times (0-60 minutes), and the reaction was halted with 10 mM EDTA. Reactions were separated and analyzed by capillary electrophoresis. EndoMS had no activity on matched T:A substrates but cleaved two nucleotides (nt) 5' to a T:T mismatch resulting in a smaller 9 nt product.

This data shows that EndoMS can efficiently eliminate double-stranded oligonucleotides that contain a mismatch.

Figure 2A:
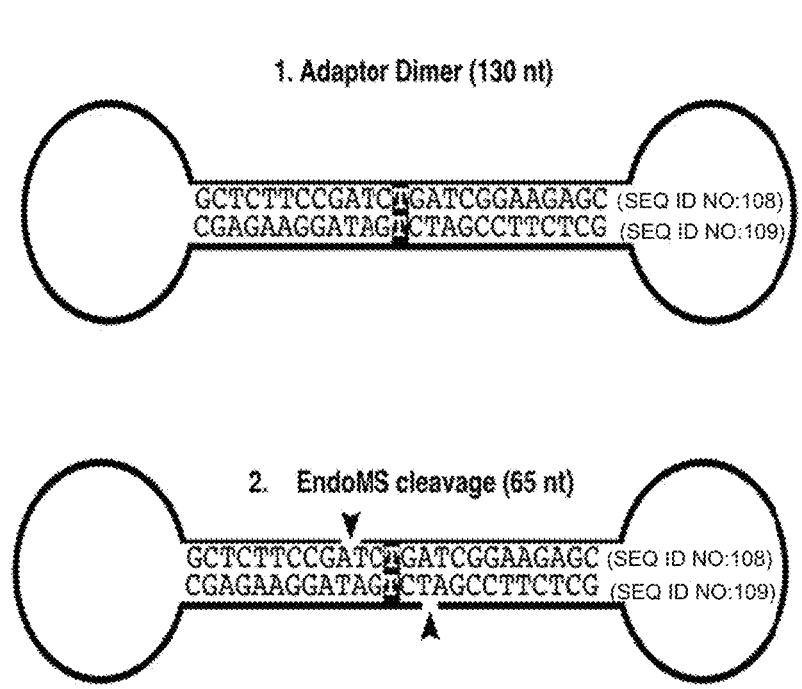
Figure 2B:
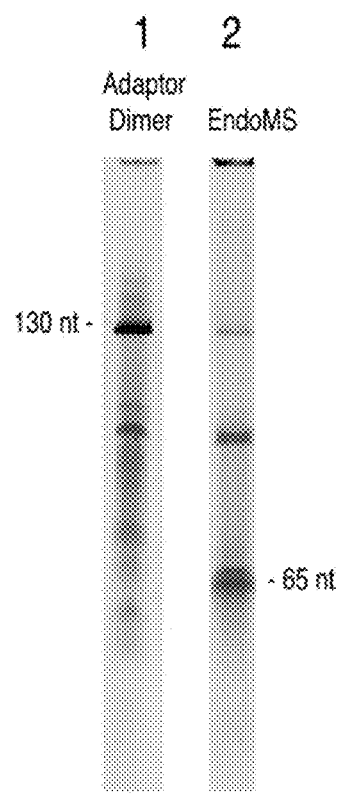

FIG. 2A-2B shows EndoMS cleaves a T:T adapter dimer mismatch. Adapters were ligated, and adapter dimers having a T:T mismatch at the ligated adapter junction were produced.

FIG. 2A shows the structures of the adapter dimers produced by ligating T-tailed hairpin oligonucleotides together.

FIG. 2B is a gel showing the analysis of reaction products. Fragments were separated by 15% TBE-Urea gel electrophoresis. Lane 1 shows uncleaved adapter dimers. A fragment of 130 nt was observed. Lane 2 shows adapter dimers treated with EndoMS. A fragment of 65 nt pieces was observed.

This data shows that adapters that contain a T overhang can ligate to each other to produce a dimer that contains a T:T mismatch. This data also shows that EndoMS can cleave those adapter dimers.

Figure 3A:
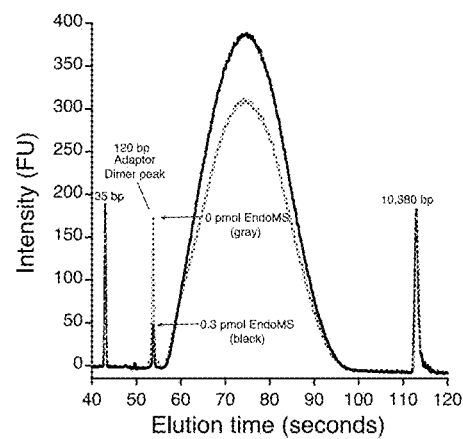
Figure 3B:
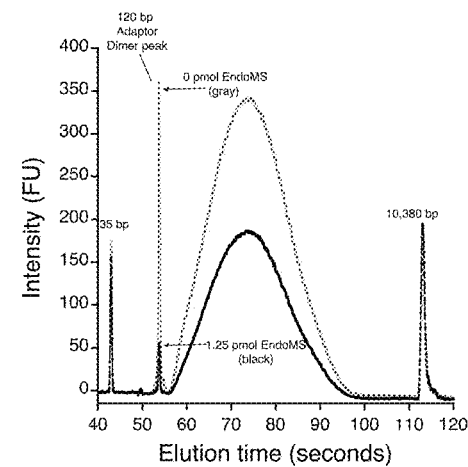
Figure 3C:
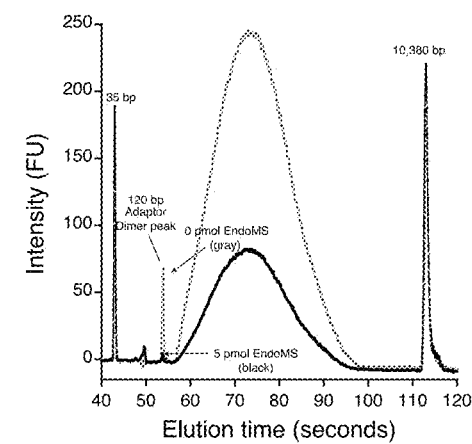

FIG. 3A-3C shows EndoMS depletes adapter dimers in next generation sequencing libraries. Human genomic DNA (10 ng) was sheared into 300 nt fragments, end repaired, dA-tailed then purified using SPRI® beads (Beckman Coulter, Brea, Calif.). Adapters (15 µM) were ligated to the insert library and purified using SPRI beads. An aliquot was treated with 0.3, 1.25 or 5 pmol EndoMS (+EndoMS: black trace) or water (−EndoMS: gray trace) and incubated for 1 hour at 37° C. Reactions were then PCR amplified for 10 cycles using Index Primer 1 and Universal Primer. Reaction products were separated and analyzed using the Agilent Bioanalyzer® (Agilent Technologies, Santa Clara, Calif.). EndoMS treatment (black) depletes adapter dimer formation.

FIG. 3A shows results obtained using 0.3 pmol EndoMS.
FIG. 3B shows results obtained using 1.25 pmol EndoMS.
FIG. 3C shows results obtained using 5 pmol EndoMS.

This data shows that EndoMS is very effective at cleaving the adapter dimers produced during next generation sequencing library construction.

Figure 4:
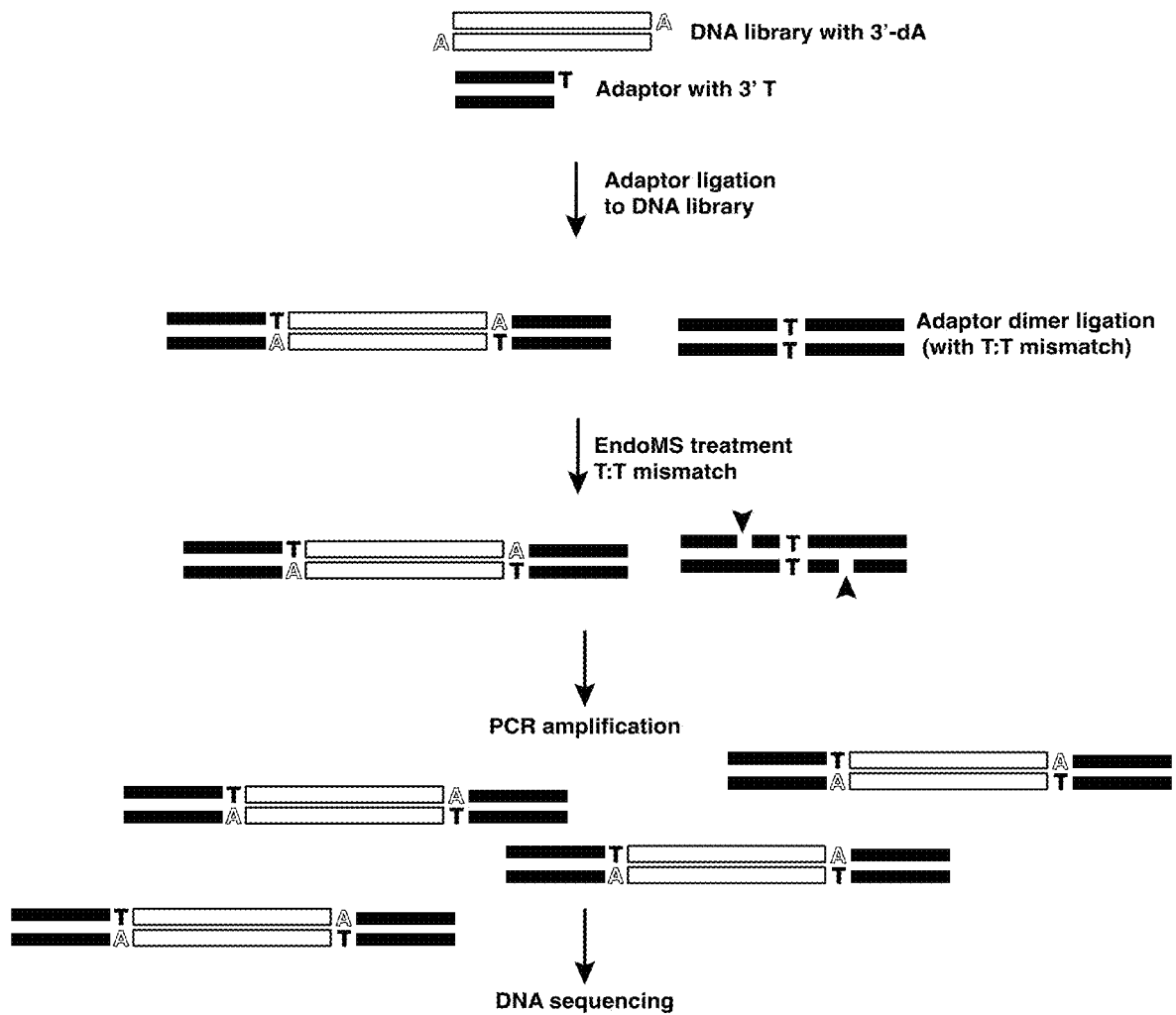

FIG. 4 schematically illustrates how EndoMS can be used to eliminate adapter dimers during NGS library construction. In this example, after adapter ligation, the DNA is purified from DNA ligase and then treated with EndoMS at 37° C. for 30 minutes in NEBNext® High-Fidelity 2× PCR Master Mix (New England Biolabs, Ipswich, Mass.). Adapter dimers are cleaved and are therefore not used as a substrate for PCR. Then PCR cycling is initiated to amplify the libraries.

Figure 5:
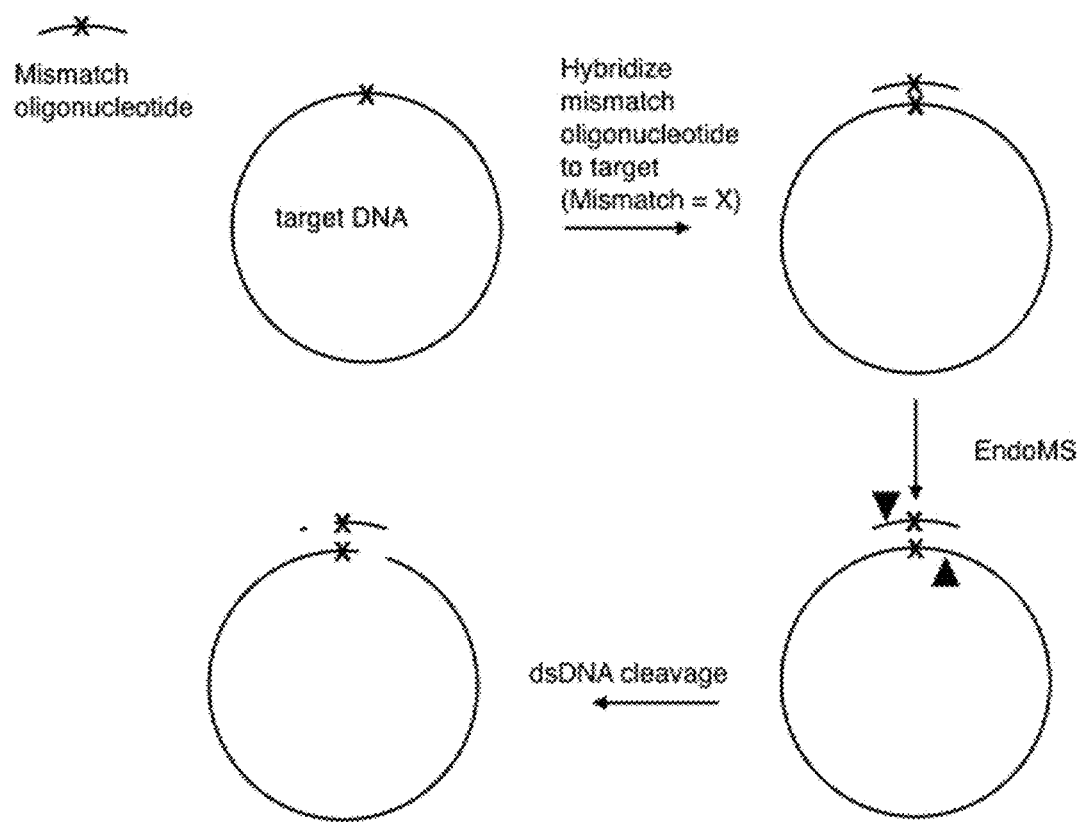

FIG. 5 shows how a mismatch oligonucleotide can target DNA cleavage using EndoMS. A mismatch oligonucleotide containing at least one T:T or U:U mismatch is hybridized to a target DNA. EndoMS cleaves at the T:T or U:U mismatch creating a dsDNA break.

Figure 6:
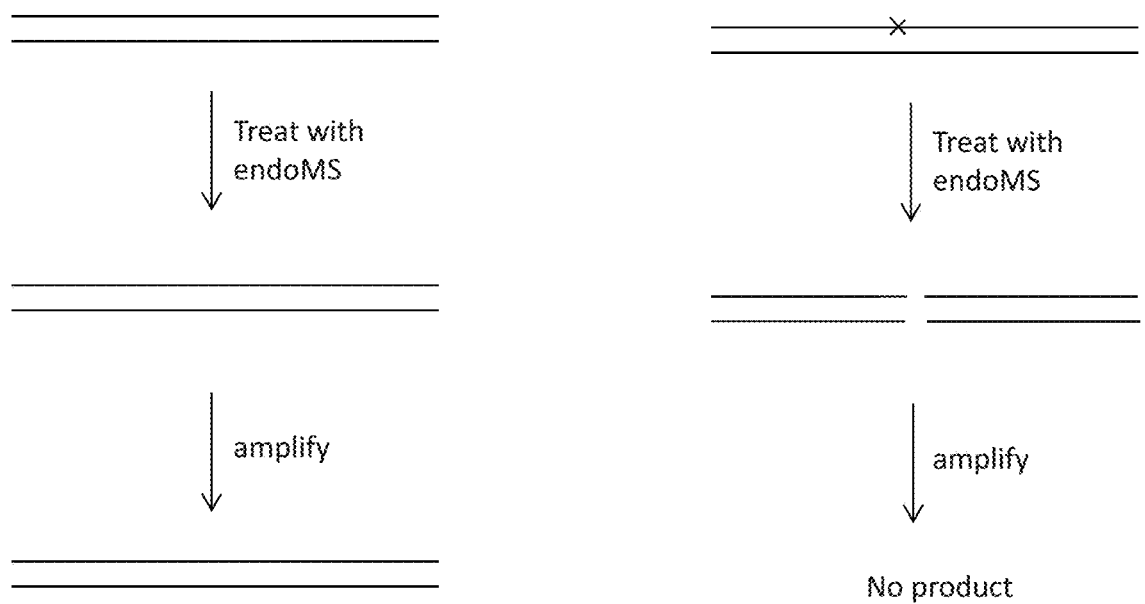

FIG. 6 shows a method for detecting a mismatched nucleotide. In this method, a sample is digested with a mismatch-specific endonuclease and a sequence is amplified, e.g., by PCR. If the sequence does not contain a mismatch, then an amplification product should be obtained. If the sequence does contain a mismatch, then no amplification product should be obtained.

Figure 7:
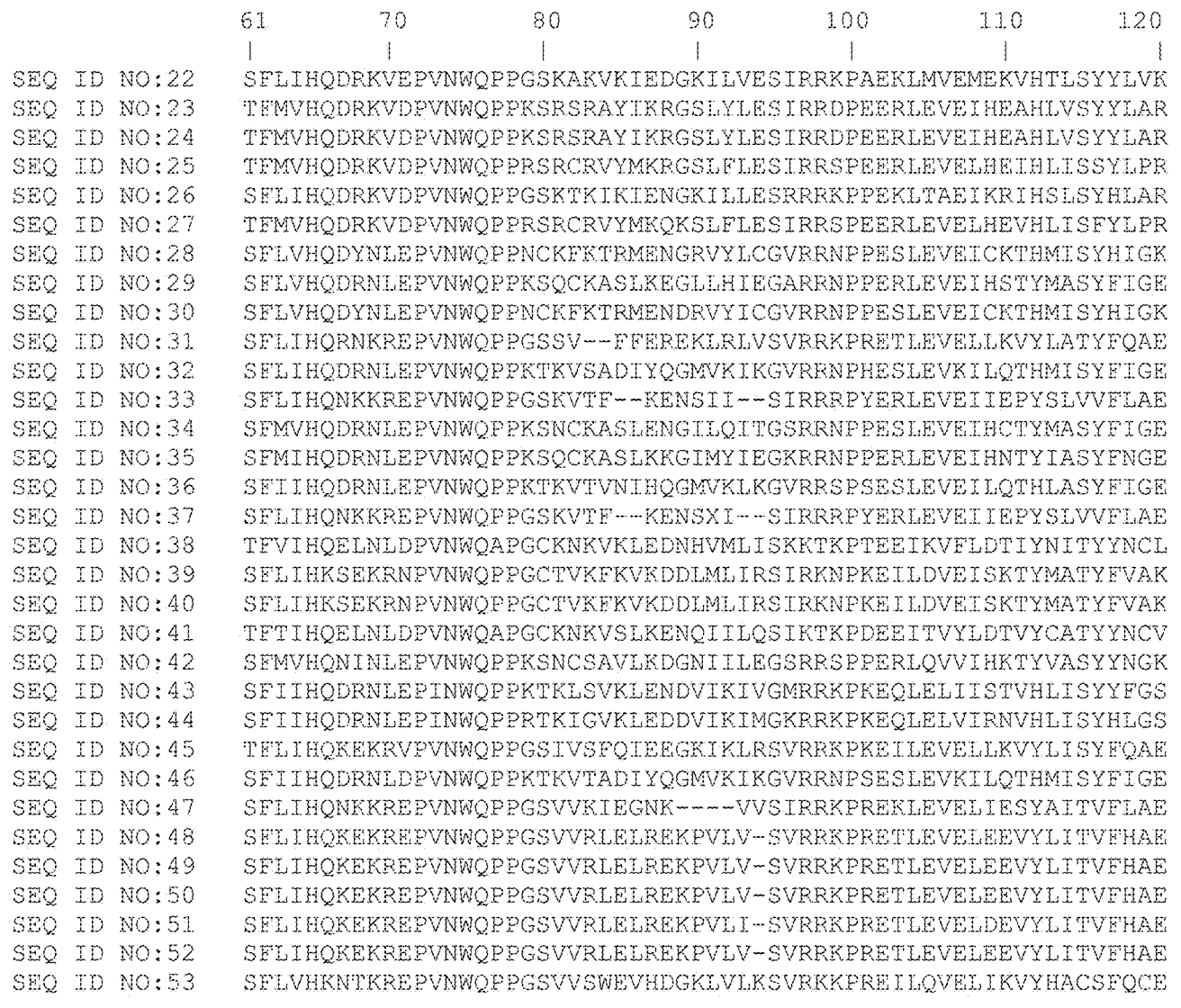
Figure 7:
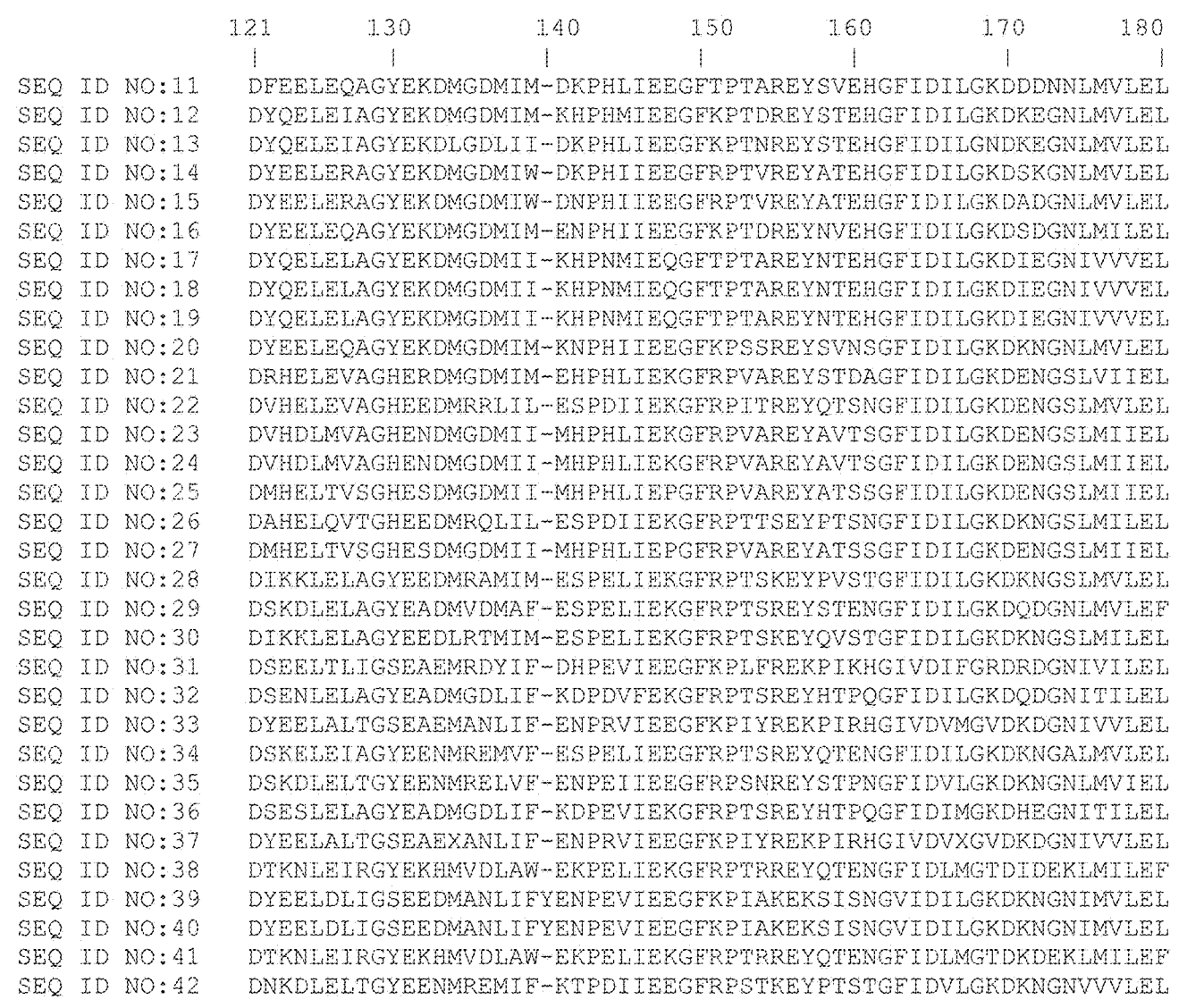

FIG. 7 shows an alignment of wild type EndoMS proteins.

DETAILED DESCRIPTION

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein as well as U.S. Provisional Application Ser. No. 62/525,803, filed Jun. 28, 2017 are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "EndoMS" refers to any member of the conserved family of endonucleases that catalyzes a double-stranded break at sites that contain a mismatched nucleotide. Examples are provided by the 104 related sequences presented herein as aligned sequences in FIG. 7 and in the sequence listings. These enzymes are considered to be a member of the RecB family of nucleases. EndoMS may also be referred to as nucS. The term "EndoMS" used herein therefore includes any of the known wild-type EndoMS family members. EndoMS catalyzes a double-stranded break at sites that contain a mismatched nucleotide. These enzymes may have a naturally-occurring amino acid sequence or may be variants of the naturally occurring proteins. For example, in certain embodiments, variants may have at least 80%, at least 85%, at least 90%, at least 95%, at least 97%, at least 98%, or at least 99% amino acid sequence identity with the naturally occurring amino acid sequence of an EndoMS family member, for example, a single EndoMS selected from the 104 sequences in FIG. 7.

The amino acid sequences of EndoMS from some bacteria and some archaea are conserved as shown in FIG. 7. For example, this enzyme family contains characteristic motifs such as a GxhDxh motif, a hxffEhK motif, and a hxxYxxhh motif, in which h is a hydrophobic residue and x is any amino acid) as described in Ren, et al. 2009 EM BO J., 28,2479-2489 and Nakai, 2016 Structure 24: 11 1960-1971. The active site (Y171) and three DNA binding site residues (R42, R70 and W75) are essential in family member *Pyrococcus abyssi* NucS. Corresponding residues D165A, E179A, and K181A were found to be essential in the *Thermococcus kodakarensis* EndoMS enzyme (see for example, see Ishino, 2016 Nucl. Acids Res. 44: 2977-2986 and Ariyoshi, et al. 2016 Structure, 24(11), 1859-1861).

It can be seen from the sequence alignments shown in FIG. 7 that K at position 181 is conserved in 100% of the 104 EndoMS proteins analyzed. D165 is conserved in 103/104 EndoMS sequences and E179 is conserved in 100% of the 104 EndoMS sequences.

This corresponds to XXXXXX in the sequence listings for SEQ ID NOs:1-104.

Additionally, in some embodiments, EndoMS may be characterized by P72 V (or I)73 N74 W75 Q76 P (or A)77 and P (or S)78.

Additionally, in some embodiments, EndoMS may be characterized by one or more amino acids at the following positions in the sequence alignment: P9, C34, Y38, G40, S44, L48, G50, K57, D59, G60, H65, P100, E102, D121, G129, E131, P143, F150, E156, G162, G168, D170, E179, K181, A189, V190, Q192,Y196, R219, G220,V222, P224, A231,E240 in which the actual position can be determined from the sequence listing.

These positions of the amino acids are derived from the alignment provided in FIG. 7.

The phylogeny and structure of this family has been studied (see Ishino, supra). Examples of wild type EndoMS family members include, but are not limited to: *Thermococcus kodakarensis* (encoded by TK1898), *Pyrococcus furiosus* (encoded by PF0012) *Pyrococcus abyssi* (encoded by PAB2263), *Halobacterium* sp. NRC-1 (encoded by VNG0171C), *Methanocaldococcus jannaschii* (encoded by MJ_0225), *Methanocella paludicola* SANAE (encoded by MCP_1445), *Methanobacterium thermoautotrophicum* (encoded by MTH1816), *Methanopyrus kandleri* (encoded by MK0507), *Sulfolobus solfataricus* (encoded by SS02208), *Pyrobaculum calidifontis* (encoded by JCM 11548, Pcal_0508), *Ignisphaera aggregans* (encoded by DSM 17230, Igag_1168), *Aeropyrum pernix* (encoded by APE_0957), *Candidatus Caldiarchaeum subterraneum* (encoded by CSUB_C1217), *Thaumarchaeota archaeon* (encoded by SCGC, AB-539-E09), *Streptomyces cattleya* (encoded by NRRL DSM 46488, SCAT_4205), *Rhodococcus jostii* (encoded by RHA1, RHA1_ro01459), *Mycobacterium colombiense* (encoded by CECT 3035, MCOL_04050) and *Actinomyces urogenitalis* (encoded by DSM 15434, HMPREF0058_1558). The sequences of these proteins are described in Ishino, Nucl. Acids Res. 2016, 44: 2977-2986, and are incorporated by reference herein.

As used herein, the term "T-tailed double-stranded adapter" refers to a double-stranded adapter that contains an end that has an overhang of a single T nucleotide (as described herein). A double-stranded adapter may be 20 to 150 bases in length, e.g., 40 to 120 bases or 50-80 bases; or shorter such as 10-40 or 20-30 bases. A double-stranded adapter may contain one or more single-stranded regions in addition to a double-stranded region that is tailed with a T.

As used herein, the nucleotide "T" is intended to include T as well as analogs of T (including U, modified T and modified U) that are still capable of base pairing with an A. Such modifications include modifications to the base and/or the sugar. Examples of modified Ts include 2-Thiothymidine-5'-triphosphate, 4-Thiothymidine-5'-Triphosphate, or 2'-Deoxythymidine-5'-O-(1-Thiotriphosphate) (TriLink Biotechnologies, San Diego, Calif.). Corresponding modifications of U may also be found and/or synthesized.

The term "adapter-ligated," as used herein, refers to a nucleic acid that has been tagged by, i.e., covalently linked with, an adapter. An adapter can be joined to a 5' end and/or a 3' end of a nucleic acid molecule.

The term "Y-adapter" refers to an adapter that contains a double-stranded region, and a single-stranded non-complementary region. The adapter is designed to have a T base overhang at the 3' end of the double stranded portion of the adapter DNA. The end of the double-stranded region can be joined to target nucleic acids such as double-stranded fragments of genomic DNA, e.g., by ligation where the 3' end of the target nucleic acid has a single base overhang which is an A. The addition of an A is a byproduct of replication of the DNA by Taq polymerase.

Each strand of an adapter-ligated target nucleic acid that has been ligated to a Y-adapter is asymmetrically tagged in that it has the sequence of one strand of the Y-adapter at one end and the other strand of the Y-adapter at the other end. Amplification of target nucleic acids that have been joined to Y-adapters at both ends results in an asymmetrically ligated nucleic acid, i.e., a nucleic acid that has a 5' end containing one adapter sequence and a 3' end that has another adapter sequence.

The terms "hairpin adapter" and "loop adapter" refer to an adapter that is in the form of a hairpin. In one embodiment, after ligation of a "hairpin adapter", the hairpin loop can be cleaved to produce strands that have non-complementary tags on the ends. In some cases, the loop of a hairpin adapter may contain a uracil residue, and the loop can be cleaved using uracil DNA glycosylase and endonuclease VIII, although other methods are known.

As used herein, the term "A-tailed double-stranded nucleic acid fragments" refers to a population of double-stranded nucleic acid fragments that have an overhang of a single A at each end. Such fragments are commonly made from fragmented DNA that has been polished and then tailed by Taq polymerase.

As used herein, the term "double-stranded adapter dimers" refers to the product of ligation between two double-stranded adapter molecules. An example of an adapter dimer is shown in FIG. 2A revealing a T-T mismatch. These "adapter dimers" can result from self-ligation of the adapters directly to each other rather than a library insert sequence Library conversion efficiency is the fraction of ligated library inserts ligated compared to the total unligated inserts, ligated inserts and adapter dimers (Library conversion efficiency =(ligated inserts/(ligated inserts +unligated inserts +adapter dimers). High library conversion efficiency is the result of all library inserts ligated to adapters with minimal adapter dimers. Alternatively, low library conversion efficiency is the result of low insert ligation efficiency and/or high efficiency adapter dimer ligation.

As used herein, the term "mismatched nucleotide" or "single nucleotide polymorphism" refers to a pair of nucleotides that oppose each other but are not complementary in a double-stranded nucleic acid. Examples of mismatched nucleotides include T:T, U:U, A:A, C:C, G:G, T:G, T:C, A:G, and A:C. In one embodiment, the mismatched nucleotide is a T:T mismatch. By way of example, a T:T mismatch may form by ligation between two double-stranded adapter molecules each having a 3' overhang of a single T nucleotide.

As used herein, the term "mismatch at the ligation junction" refers to a pair of opposing nucleotides that are not complementary that are each present adjacent to a phosphodiester bond produced in a ligation. In one embodiment, the pair of opposing nucleotide are both T nucleotides, resulting in a T:T mismatch at the ligation junction". This embodiment includes the pair of opposing nucleotide being U nucleotides, giving rise to a U:U mismatch at the ligation junction As used herein, the term "thermostable" refers to an enzyme that has optimal activity at a temperature of at least 50° C.

As used herein, the term "not perfectly complementary" refers to two sequences that are sufficiently complementary to allow the two sequences to hybridize to one another under high stringency conditions to produce a duplex, but wherein the duplex formed by hybridization of the two sequences comprises at least one mismatch, e.g., a single mismatch. Two sequences that are "not perfectly complementary" are therefore less than 100% complementary (but may be at least 90%, 95%, 98% or 99% complementary).

As used herein, the term "without enriching for the adapter-ligated fragments by size" refers to a method in which there is no step that selects for adapter-ligated fragments by their size, e.g., using a product designed to purify PCR products from adapters, such as a QIAquick® (Qiagen, Germantown, Md.) or SPRI column.

As used herein, the term "nucleic acid" refers to RNA or DNA and include RNA or DNA oligonucleotides, exons, introns, other non coding DNA, unspecified genomic DNA, whole genomes, cellular RNA species such as non coding RNA, miRNA, mRNA, tRNA, rRNA etc. The nucleic acid may be short (less than 100 nt), medium (100 nt-100 kb) or long in length (greater than 100 kb) and may comprise or consist of target sequences.

In some embodiments, the method may comprise ligating a double-stranded portion of an adapter with a T-tail as defined herein at the 3' end of one strand to double-stranded fragments of nucleic acid having an A-tail at the 3' end to produce ligation products that comprise double-stranded nucleic acid fragments having adapters ligated at each end and double-stranded adapter dimers that comprise a T:T mismatch at the ligation junction, and cleaving both strands of the adapter dimers using EndoMS.

The A-tailed double-stranded fragments of nucleic acid may be made by extracting nucleic acid (e.g. DNA) from an initial sample, optionally fragmenting the nucleic acid (e.g. DNA), polishing the ends of the nucleic acid fragments (using, e.g., T4 DNA polymerase) and A-tailing the polished fragments (using, e.g., Taq polymerase). In some embodiments, the initial sample may contain intact double-stranded nucleic acids (e.g. dsDNA). In these embodiments, the sample may be fragmented before it is A-tailed. In these embodiments, fragmenting may be done mechanically (e.g., by sonication, nebulization, or shearing, etc.) or using a double-stranded DNA "dsDNA" Fragmentase® enzyme (New England Biolabs, Ipswich Mass.). In other embodiments, the nucleic acid (e.g. DNA) in the sample may already be fragmented (e.g., as is the case for FPET samples and circulating cell-free DNA (cfDNA), e.g., ctDNA).

The T-tailed adapters are synthetic oligonucleotides that form Y-adaptors or loop adaptors both of which contain a double stranded region and a single stranded region and both have the T-tail at the 3' terminus of the double stranded region.

In some embodiments, the A-tailed double-stranded nucleic acid fragments may have a median size that is below 1 kb (e.g., in the range of 50 bp to 500 bp, 80 bp to 400 bp, or 200-400 bp), although fragments having a median size outside of this range may be used. In some embodiments, the amount of nucleic acid (e.g. DNA) in a sample may be limiting. For example, the sample of fragmented DNA may contain less than 200 ng of fragmented human DNA, e.g., 1 pg to 20 pg, 10 pg to 200 ng, 100 pg to 200 ng, 1 ng to 200 ng or 5 ng to 50 ng, or less than 10,000 (e.g., less than 5,000, less than 1,000, less than 500, less than 100, less than 10 or less than 1) haploid genome equivalents, depending on the genome.

As would be apparent, the ligation step may be done using any suitable ligase including, but not limited to T4 DNA ligase.

As noted above, the EndoMS treatment not only removes adapter dimers from the reaction, but potentially also double-stranded nucleic acid molecules (e.g. dsDNA molecules) that contain single nucleotide mismatches. Single nucleotide mismatches may result from damaged nucleotides that are read by a polymerase as a different nucleotide and, as such, damaged nucleotides can confound the results obtained by sequencing those fragments. For example, deaminated cytosines and oxidized guanines both base pair with adenine, which lead to erroneous base calls after amplification. It has been found that damaged nucleotides are a pervasive cause of sequencing errors and this, in turn, confounds variant identification (see, e.g., Chen, et al., Science 2017 355:752-756). In these cases, a "damaged nucleotide" is any derivative of adenine, cytosine, guanine, and thymine that has been altered in a way that allows it to pair with a different base. In non-damaged DNA, A base pairs with T and C base pairs with G. However, some bases can be oxidized, alkylated or deaminated in a way that effects base pairing. For example, 7,8-dihydro-8-oxoguanine (8-oxo-dG) is a derivative of guanine that base pairs with adenine instead of cytosine. This derivative causes a G to T transversion after replication. Deamination of cytosine produces uracil, which can base pair with adenine, leading to a C to T change after replication. Other examples of damaged nucleotides that are capable of mismatched pairing are known. Removal of molecules that contain damaged nucleotides can provide more reliable sequencing data.

In some embodiments, the method may comprise amplifying the adapter-ligated double-stranded nucleic acid fragments after the reaction has been treated with EndoMS. In these embodiments, the amplification may be done by PCR (e.g., using a first primer that hybridizes to an adapter sequence and another primer that hybridizes to the complement of an adapter sequence). As would be apparent, the primers used for amplification and/or the adapters may be compatible with use in any next generation sequencing platform, e.g., Illumina's reversible terminator method, Roche's pyrosequencing method (454), Life Technologies' sequencing by ligation (the SOLID® platform), Life Technologies' Ion Torrent platform or Pacific Biosciences' fluorescent base-cleavage method, etc. The fragments may be sequenced without amplification, or after they are amplified. Examples of such methods are described in the following references: Margulies, et al., Nature, 2005, 437:376-80); Ronaghi, et al., Analytical Biochemistry, 1996, 242:84-9; Shendure, Science, 2005, 309:1728; Imelfort, et al., Brief Bioinform. 2009, 10:609-18; Fox, et al., Methods Mol Biol. 2009, 553:79-108; Appleby, et al., Methods Mol Biol. 2009, 513:19-39; English, PLoS One. 2012 7:e47768; and Morozova, Genomics, 2008, 92:255-64, which are incorporated by reference for the general descriptions of the methods and the particular steps of the methods, including all starting products, reagents, and final products for each of the steps. The sequencing may be done by paired-end sequencing, although single read sequencing can be done in some cases.

Because the adapter dimers can be efficiently removed using EndoMS, there is no need to remove the adapter dimers by size separation. As such, in some embodiments, the method may be done without enriching for the adapter-ligated double-stranded nucleic acid fragments by size. For example, there is no need to perform a size separation after ligation but before amplification, after amplification and before sequencing, or after ligation and before sequencing (if the sample is not amplified beforehand).

In some embodiments, the ligation and EndoMS steps may be done in the same vessel. In these embodiments, the method may be done by incubating a reaction mix comprising the T-tailed double-stranded adapter, the A-tailed double-stranded fragments of nucleic acid, ligase, and the EndoMS, to produce the ligation products and cleave both strands of the adapter dimers. In some embodiments, the EndoMS may be thermostable. In these embodiments, the ligation reaction may be terminated and the EndoMS may be activated by changing the temperature of the reaction mix. For example, the ligation step may be performed at a temperature of between 15° C. to 25° C., and the EndoMS treatment step may be done at a temperature that is at least 10° C., at least 20° C., or at least 30° C. higher than the ligation step (e.g., at a temperature of at least 35° C., at least 45° C., or at least 55° C.). Alternatively, the EndoMS may be mesophilic.

Also provided herein is a method for cleaving a nucleic acid (such as DNA). In these embodiments, the method may comprise hybridizing the nucleic acid with an oligonucleotide that is not perfectly complementary to a target sequence to produce a duplex that comprises one or more mismatches (e.g., a single mismatch), and treating the duplex with EndoMS, thereby cleaving the nucleic acid at the target sequence. In these embodiments, the nucleic acid (e.g. DNA) may be single-stranded (e.g., which can be made by denaturing a sample that comprises dsDNA). Alternatively, the nucleic acid (e.g. DNA) may be double-stranded, and the hybridizing is done by strand invasion. This can be done by, e.g., incubating the reaction at a temperature that is insufficient to denature the nucleic acid in the sample but sufficient to allow strand invasion, such as a temperature in the range of 37° C. to 80° C. Strand invasion can be facilitated by single-stranded DNA binding proteins (SSBPs).

The oligonucleotide used in this method may be of any suitable length, e.g., between 15 and 100 nucleotides in length. In some embodiments, in the duplex, the oligonucleotide and nucleic acid comprise at least 8 nucleotides of perfect complementarity (at least 10, at least 15, or at least 20 nucleotides of perfect complementarity) on either side of a mismatch.

EndoMS can also be used to identify single nucleotide mismatches in a double-stranded nucleic acid such as any dsDNA. In some embodiments, this method may comprise: (a) reacting a sample comprising the double-stranded nucleic acid (e.g. dsDNA) with EndoMS to produce a reaction product, wherein the EndoMS cleaves both strands of the double-stranded nucleic acid only if it contains a mismatch; (b) subjecting the reaction product of (a) to amplification under conditions that amplify the double-stranded nucleic acid if it is uncleaved; and (c) detecting whether an amplification product is present, wherein the presence of the product indicates that the double-stranded nucleic acid does not have a mismatched nucleotide, and the absence of a product indicates that the double-stranded nucleic acid has a mismatched nucleotide. As would be apparent, step (b) can be done by PCR, using primers that flank the mismatch.

In this method, the double-stranded nucleic acid (e.g. dsDNA) may be from any source, or from a mixture of two or more different sources. In some embodiments, the mismatch may be at a ligation junction (e.g., at the ligation junction of an adapter dimer, as discussed above. In other embodiments, the dsDNA may be genomic DNA. In these embodiments, the mismatch may be caused by DNA damage. For example, the dsDNA may contain a damaged nucleotide. In other embodiments, the dsDNA may be a PCR product or double-stranded cDNA. In these embodiments, the mismatch may be caused by mis-incorporation of a nucleotide. In some embodiments, the double-stranded nucleic acid (e.g. dsDNA) may comprise two strands (e.g., a first strand and a second strand that may comprise one or more nucleotide substitutions relative to the first strand) that have been hybridized together. In one embodiment, the method comprises the initial step of hybridizing together a first nucleic acid strand and a second nucleic acid strand, wherein the first and second strands are not perfectly complementary (i.e. to form a duplex comprising one or more mismatches). In this embodiment, one of the strands in a duplex may contain the complement of a single nucleotide polymorphism relative to the other strand in the duplex.

In this method, the presence of an amplification product can be detected by gel or capillary electrophoresis, for example, although other methods that can separate DNA molecules by size can be used.

The detection may be qualitative or quantitative. In some embodiments, the results may be compared to a control. As such, the detecting step may comprise quantifying the amount of the amplification product.

The methods described above can be employed to analyze genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, wherein certain embodiments the mammal is a human. In exemplary embodiments, the sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, synovial fluid, urine, amniotic fluid, and semen. In particular embodiments, a sample may be obtained from a subject, e.g., a human. In some embodiments, the sample comprises fragments of human genomic DNA. In some embodiments, the sample may be obtained from a cancer patient. In some embodiments, the sample may be made by extracting fragmented DNA from a patient sample, e.g., a formalin-fixed paraffin embedded tissue sample. In some embodiments, the patient sample may be a sample of cell-free "circulating" DNA from a bodily fluid, e.g., peripheral blood, e.g., from the blood of a patient or of a pregnant female. The DNA fragments used in the initial step of the method should be non-amplified DNA that has not been denatured beforehand.

Kits

Also provided by this disclosure is a kit for practicing the subject method, as described above. For example, in some embodiments, the kit may comprise a T-tailed double-stranded adapter and an EndoMS enzyme. The kit may also contain a ligase (e.g., T4 DNA ligase), a reaction buffer (which may be in concentrated form) and/or reagents for A-tailing fragments (e.g., T4 DNA polymerase and Taq polymerase), etc. The various components of the kit may be present in separate containers or certain compatible components may be pre-combined into a single container, as desired.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

EMBODIMENTS

Embodiment 1. A method for reducing adapter dimers, comprising:
(a) ligating a T-tailed double-stranded adapter to an A-tailed double-stranded fragment of nucleic acid to produce ligation products that comprise adapter-ligated fragments and double-stranded adapter dimers that comprise a T:T mismatch at the ligation junction; and
(b) cleaving both strands of the adapter dimers using EndoMS.

Embodiment 2. The method of embodiment 1, further comprising (c) amplifying the adapter-ligated fragments.

Embodiment 3. The method of embodiment 2, wherein the amplifying is done using primers that hybridize to the adapter, or complement thereof.

Embodiment 4. The method of embodiments 2 or 3, wherein the method is done without enriching for the adapter-ligated double stranded nucleic acid fragments by size.

Embodiment 5. The method of any prior embodiment, wherein the fragments are genomic fragments.

Embodiment 6. The method of any prior embodiment, wherein the T-tailed adapter is a Y adapter.

Embodiment 7. The method of any prior embodiment, wherein the T-tailed adapter is a loop adapter.

Embodiment 8. The method of any prior embodiment, wherein the method comprises incubating a reaction mix comprising the T-tailed double-stranded adapter, the A-tailed double-stranded fragments of nucleic acid, a ligase, and the EndoMS to produce the ligation products and cleaving both strands of the adapter dimers.

Embodiment 9. The method of any prior embodiment, wherein the EndoMS is thermostable.

Embodiment 10. A kit comprising:
(a) a T-tailed double-stranded adapter; and
(b) an EndoMS enzyme.

Embodiment 11. The kit of embodiment 10, wherein the kit further comprises a ligase.

Embodiment 12. The kit of any of embodiments 10-11, wherein the kit further comprises a reaction buffer.

Embodiment 13. A method, comprising:
(a) hybridizing a first single stranded nucleic acid with a second single stranded nucleic acid that is not perfectly complementary to a target sequence in the first nucleic acid to produce a duplex nucleic acid that comprises one or more mismatches; and
(b) treating the duplex nucleic acid with EndoMS, so as to cleave the duplex nucleic acid at the target sequence.

Embodiment 14. The method of embodiment 13, wherein the second single stranded nucleic acid is an oligonucleotide.

Embodiment 15. The method of embodiments 13 or 14, wherein the first single stranded nucleic acid is denatured dsDNA.

Embodiment 16. The method of any of embodiments 13-15, wherein the hybridizing is done by strand invasion.

Embodiment 17. The method of any of embodiments 13-16, wherein, in the duplex, the first and second nucleic acids comprise at least 8 nucleotides of perfectly complementarity on each side of a mismatch.

Embodiment 18. A method for identifying a mismatched nucleotide in a double-stranded nucleic acid, comprising:
(a) reacting a sample comprising the nucleic acid with EndoMS to produce a reaction product, wherein the EndoMS cleaves both strands of the nucleic acid only if it contains a mismatch;
(b) subjecting the reaction product of (a) to amplification under conditions that amplify the nucleic acid if it is uncleaved; and
(c) detecting the presence of an amplification product, wherein the presence of the product indicates that the double-stranded nucleic acid does not have a mismatched nucleotide and the absence of a product indicates that the double-stranded nucleic acid has a mismatched nucleotide.

Embodiment 19. The method of embodiment 17, wherein step (b) is done by PCR, using primers that flank the mismatch.

Embodiment 20. The method of any of embodiments 18-19, wherein mismatch is at a ligation junction.

Embodiment 21. The method of any of embodiments 18-20, wherein the nucleic acid is an adapter dimer.

Embodiment 22. The method of any of embodiments 18-21, wherein the double-stranded nucleic acid is genomic DNA.

Embodiment 23. The method of any of embodiments 18-22, wherein the mismatch is caused by DNA damage.

Embodiment 24. The method of any of embodiments 18-23, wherein the double-stranded nucleic acid comprises two strands that have been hybridized together.

Embodiment 25. The method of any of embodiments 18-24, wherein the detecting step (c) comprises quantifying the amount of the amplification product.

Embodiment 26. A method for identifying a mismatched nucleotide in a double-stranded nucleic acid in vivo, comprising:
(a) reacting a nucleic acid in a cell sample with EndoMS to produce a reaction product, wherein the EndoMS cleaves both strands of the nucleic acid only if it contains a mismatch; and wherein the EndoMS is (i) expressed by an extrachromosomal DNA introduced in the cell; or (ii) introduced into the cell by a liposome or transport agent;
(b) detecting cleavage of the nucleic acid in the cell.

EXAMPLES

Aspects of the present teachings can be further understood in light of the following examples, which should not be construed as limiting the scope of the present teachings in any way.

Example 1

EndoMS Treatment to Eliminate Oligonucleotides Having a Mismatch

To test the ability of EndoMS variants to cleave mismatched oligonucleotides, substrates were designed with perfect base pairing (T:A) or with a T:T mismatch (T:T) to model mismatch oligonucleotide assembly used in synthetic biology gene assembly.

An oligonucleotide was labeled by VIC at its 5' end (VIC-CGCCAGGGTTTTCCCAGTCACGAC) (SEQ ID NO:105). The labeled oligonucleotide was annealed to the following oligonucleotides to form double-stranded substrates having either a T:A match (GTCGTGACTGG-GAAAACCCTGGCG) (SEQ ID NO:106) or T:T mismatch (GTCGTGACTGGGTAAACCCTGGCG) (SEQ ID NO:107) (FIG. 1A). In 200 µl, EndoMS (1 pmol) was incubated with the T:A or T:T substrate (20 nM) at 37° C. for between 0 and 60 minutes in 1× NEBuffer 2 (50 mM NaCl, 10 mM Tris-HCl, 10 mM MgCl$_2$, 1 mM DTT, pH 7.9 at 25° C.). Aliquots (20 µl) were sampled and stopped with EDTA (50 mM final concentration) at various time points (0-60 minutes). Reaction products were separated by capillary electrophoresis using a 3730 xl Genetic Analyzer (Applied Biosystems, Foster City, Calif.), and fluorescent peaks were analyzed using Peak Scanner software version 1.0 (Applied Biosystems, Foster City, Calif.) (14). The concentration of product (9 nt) was graphed as a function of time. EndoMS lacked activity on matched oligonucleotide substrates but cleaved two bp 5' to the T:T mismatch on each strand leaving a 5' overhang (FIG. 1B). This data shows that EndoMS can cleave both strands of a substrate that contains a T:T mismatch.

Example 2

Adapters that Contain a 3' T or 3'U Overhang Can Ligate Together to Form Dimers

Synthetic Adapter oligonucleotide 1 pATCTGATCG-GAAGAGCACACGTCTGAACTCCAGTCTA-CACTCTTTCCCTACACGACGCTCTTCCGATCT-GATCGGA (SEQ ID NO:108) and Synthetic Adapter oligonucleotide 2 p-AGAGCACACGTCT-GAACTCCAGTCTACACTCTTTCCCTA-CACGACGCTCTTCCG (SEQ ID NO:109) are loop adapters. In each adapter, the 5' end of the adapter is complementary to the 3' end of the adapter, and the adapters form a stem-loop when they are annealed. The adapters, when they are in the hairpin structure, both contain a single nucleotide 3' T overhang. Molecules that contain a single nucleotide 3' T overhang should, in theory, only ligate to other molecules that contain a single nucleotide 3' A overhang, not molecules that contain a single nucleotide 3' T overhang.

The adapters were annealed and ligated to each other using T4 DNA ligase to produce a loop adapter dimer that contains a T:T mismatch at the adapter dimer junction (as shown in FIG. 2A). To demonstrate EndoMS cleavage of adapter dimers, in a 20 µl reaction, the loop adapter dimer (40 nM) was incubated with EndoMS (1 pmol) in 1× NEBNext Ultra™ II Q5® Master Mix (New England Biolabs, Ipswich, Mass.) for 1 hour at 37° C. Reaction products were analyzed by gel electrophoresis (FIG. 2B).

Intact adapter dimer runs at 130 nt by gel electrophoresis. Cleavage with EndoMS at the T:T mismatch will yield 65 nt products as resolved by gel electrophoresis.

Example 3

Removal of Adapter Dimers from NGS Library Preparation

To test if EndoMS cleaved and decreased adapter dimers formed during next generation sequencing library construction, a next generation sequencing library was prepared according to the manufacturer's protocol (NEBNext Ultra II DNA Library Prep Kit). Briefly, human DNA was sheared into 300 nt fragments by acoustic shearing. Then, sheared DNA fragments (10 ng) were end repaired, dA-tailed and ligated to NEBNext Adapter for Illumina (15 µM). Excess small DNAs (primers) were effectively removed from the reaction mix using SPRI select beads. Although adapters and adapter dimers are considered to be small DNA, removal of adapter dimers capable of binding primers intended for amplifying target DNA using any current separation method such as beads is generally incomplete.

Instead, residual adapter dimers were removed enzymatically as follows: NEBuffer 1 was added to the cleaned up libraries and split in half. Aliquots (20 µl) were treated with 0.3, 1.25 or 5 pmoles EndoMS or water and incubated for 1 hour at 37° C. Reactions were then PCR amplified for 10 cycles using Index Primer 1 and Universal Primer (as described by the manufacture's protocol (New England Biolabs, Ipswich, Mass.)). Reaction products were separated and analyzed using the Agilent Bioanalyzer. The data for the different reactions is shown in FIG. 3A (0.3 pmoles EndoMS), FIG. 3B (1.25 pmoles EndoMS) and FIG. 3C (5 pmols EndoMS). Results show that EndoMS treatment reduces adapter dimers.

Example 4

Mismatch Oligonucleotide Targeted dsDNA Cleavage Using EndoMS

Synthetic oligonucleotides can be designed to complement sequences in a target DNA such as genomic DNA or plasmid DNA where the design includes a single mismatch at a T to create a T:T mismatch. Alternatively, the design includes more than one mismatch at a T to create more than one T:T mismatch. EndoMS or thermostable EndoMS can then be used to cleave the duplex at the mismatch site using any of the cleavage methods described above. Briefly, the mismatch oligonucleotide (1 µM) is annealed to the target DNA (0.5 µM) in 1× NEBuffer 2 by heating to 95° C. for 5 minutes then cooling to 25° C. EndoMS is then added to cleave at mismatches. Alternatively, the mismatch oligonucleotide (1 µM) is annealed to the target DNA (0.5 µM) in 1× NEBuffer 2 and 1 pmol Thermostable EndoMS and cycled between 95° C. and 37° C. After annealing, a mismatch will form and EndoMS will cleave the heteroduplex DNA. The result of this method is a dsDNA break at a specific site directed by mismatch cleavage by EndoMS. This method provides a dsDNA cleavage reagent whose specificity is targeted by a mismatched oligonucleotide.

---

What is claimed is:

1. A method for cleaving adapter dimers produced in a ligation reaction, comprising:
   (a) ligating a T-tailed double-stranded adapter to A-tailed double-stranded fragments of nucleic acid to produce ligation products that comprise: (i) adapter-ligated double-stranded nucleic acid fragments and (ii) double-stranded adapter dimers that comprise a T:T mismatch at the ligation junction; and
   (b) cleaving both strands of the adapter dimers using EndoMS.

2. The method of claim 1, further comprising (c) amplifying the adapter-ligated double-stranded nucleic acid fragments.

3. The method of claim 2, wherein the amplifying is done using primers that hybridize to the ligated adapter, or complement thereof.

4. The method of claim 2, wherein the method is done without enriching for the adapter-ligated double-stranded nucleic acid fragments by size.

5. The method of claim 1, wherein the double-stranded nucleic acid fragments are genomic fragments.

6. The method of claim 1, wherein the T-tailed double-stranded adapter is a Y adapter or a pair of Y adapters.

7. The method of claim 1, wherein the T-tailed double-stranded adapter is a loop adapter.

8. The method of claim 1, wherein the method comprises incubating a reaction mix comprising the T-tailed double-stranded adapter, the A-tailed double-stranded fragments of nucleic acid, a ligase, and the EndoMS, to produce the ligation products and cleave both strands of the adapter dimers.

9. The method of claim 1, wherein the EndoMS is thermostable.

* * * * *